United States Patent [19]
Isaacs et al.

[11] Patent Number: 5,864,488
[45] Date of Patent: Jan. 26, 1999

[54] THREE DIMENSIONAL GLYCOPROTEIN HORMONE STRUCTURE REPRESENTATION USING A COMPUTER

[75] Inventors: Neil William Isaacs; Adrian Jonathan Lapthorn, both of Glasgow; Deborah Claire Harris, London, all of United Kingdom; Peter Diederik Jan Grootenhuis, Oss, Netherlands

[73] Assignee: University Court of the University of Glasgow, Glasgow, Scotland

[21] Appl. No.: 395,238

[22] Filed: Feb. 24, 1995

[30] Foreign Application Priority Data

Feb. 24, 1994 [GB] United Kingdom .................. 9403600

[51] Int. Cl.$^6$ .................................................. C07K 14/575
[52] U.S. Cl. .......................... 364/496; 364/499; 530/397; 530/399; 435/69.1
[58] Field of Search ...................................... 530/399, 397; 435/69.1; 364/496, 499; 395/919, 932

[56] References Cited

U.S. PATENT DOCUMENTS

| | | | |
|---|---|---|---|
| 4,704,692 | 11/1987 | Ladner ..................................... | 364/496 |
| 4,881,175 | 11/1989 | Ladner ..................................... | 364/496 |
| 5,177,193 | 1/1993 | Boime et al. ........................... | 530/397 |
| 5,331,573 | 7/1994 | Balaji et al. ............................. | 364/497 |
| 5,500,807 | 3/1996 | Lavin et al. ............................. | 364/496 |

OTHER PUBLICATIONS

Boyd, DB, Compendium of software for molecular modeling, Reviews in Computation Chemistry, vol. 3, Lipkowitz et al., Eds, VCH Publishers: New York, pp. 223–247, 1992.

Reichert et al., Structure–function relationships of the glycoprotein hormones and their receptors, Trends Pharmacol. Sci., 12(5): 199–203, May 1991.

Cohen et al., Molecular modeling software and methods for medicinal chemistry, J. Med. Chem., 33(3): 883–894, Mar. 1990.

J.W. Lustbader et al., "The Application of Chemical Studies of Human Chorionic Gonadotrpin to Visualize Its Three–Dimensional Structure," Endocrine Reviews 14:3:291–311, Jun. 1993.

K.P. Willey et al., "Functionally Distinct Agonist and Receptor–binding Regions in Human Chorionic Gonadotropin," The Journal of Biological Chemistry 264:33:19716–19721.

J.W. Lustbader, "Defining the Tertiary Structure of Human Gonadotropin", Serono Symposium: Symposium on Glycoprotein Hormones: Structure, Function and Clinical Implications, Santa Barbara California, Mar. 11–14, 1993.

P. Manjunath et al., "Biochemical, Biological, and Immunological Propoerties of Chemically Deglycoslyated Human Choriogonadotropin," J. Biol. Chem. 257, 7109–7115, (1982).

C. Oefner et al., "Crystal structure of human platelet–derived growth factor BB," The EMBO Journal, 11:11:3921–3926, 1992.

D.C. Harris et al., "Preliminary X–Ray Diffraction Analysis of Human Chorionic Gonadotropin," The Journal of Biological Chemistry, 264:12:6705–6707, 1989.

N. McDonald et al., "A Structural Superfamily of Growth Factors Containing a Cystine Knot Motif," Cell, 73:421–424, 1993.

R.J. Ryan et al., "Structure–Function Relationships of Gonadotropins," Recent Progress in Hormone Research, 43:383–428, 1987.

J. Murray–Rust et al.,, "Topological similarities in TGF- –beta2, PDGF–BB and NGF define a superfamily of polypeptide growth factors," Structure, 1:2:153–159.

M.P. Schlunegger, "Refined Crystal Structure of Human Transforming Growth Factor beta2 at 1.95 A Resolution," J. Mol. Biol., 231:445–448, 1993.

N.Q. McDonald et al., "new Protein fold revealed by a 2,3–A resolution crystal structure of nerve growth factor," Nature, 354;411–414, 1991.

J.W. Lustbader, "Crystallization and Characterization of Human Chorionic Gonadotropin in Chemically Deglycosylated and Enzymatically Desialylated States," Biochemistry, 28:24:9239–9243.

Primary Examiner—Stephen Walsh
Assistant Examiner—Claire M. Kaufman
Attorney, Agent, or Firm—Mary E. Gormley

[57] ABSTRACT

The three-dimensional structure of human chorionic gonadotrophin (hCG) has been determined by X-ray crystallography and the coordinates of the individual atoms are presented. Analogues of hCG and other glycoprotein hormones sharing a similar α-subunit structure are produced by inputting chemical changes to the structure into a computer loaded with three-dimensional molecular simulation software and representing visually on a computer display. The three-dimensional structures of the original glycoprotein and the chemically modified analogues are compared, and those analogues wherein the three-dimensional configuration and spatial arrangement of regions involved in receptor binding and signal transduction remain substantially preserved are selected for synthesis by molecular biology techniques and screening for biological activity. Glycoprotein analogues with additional glycosylation sites, and deletion of non-essential hairpins are disclosed.

9 Claims, 49 Drawing Sheets

```
CRYST1   88.680   88.680  177.240  90.00  90.00 120.00
SCALE1      0.011274  0.006508  0.000000        0.00000
SCALE2      0.000000  0.013018  0.000000        0.00000
SCALE3      0.000000  0.000000  0.005643        0.00000
ATOM      1  CB   GLN A   5      26.296   28.901   -1.992  1.00 41.04
ATOM      2  CG   GLN A   5      26.358   29.625   -3.343  1.00 44.78
ATOM      3  CD   GLN A   5      24.995   29.677   -4.050  1.00 58.76
ATOM      4  OE1  GLN A   5      24.445   30.758   -4.284  1.00 61.72
ATOM      5  NE2  GLN A   5      24.450   28.504   -4.402  1.00 60.80
ATOM      8  C    GLN A   5      25.959   26.641   -0.907  1.00 34.19
ATOM      9  O    GLN A   5      24.920   26.043   -1.196  1.00 34.91
ATOM     12  N    GLN A   5      26.366   26.770   -3.316  1.00 37.33
ATOM     14  CA   GLN A   5      26.708   27.416   -2.005  1.00 37.42
ATOM     15  N    ASP A   6      26.496   26.602    0.315  1.00 29.13
ATOM     17  CA   ASP A   6      25.859   25.868    1.409  1.00 27.08
ATOM     18  CB   ASP A   6      26.902   25.228    2.326  1.00 28.58
ATOM     19  CG   ASP A   6      26.460   23.870    2.871  1.00 39.81
ATOM     20  OD1  ASP A   6      25.260   23.695    3.173  1.00 37.76
ATOM     21  OD2  ASP A   6      27.316   22.962    2.987  1.00 43.81
ATOM     22  C    ASP A   6      24.968   26.794    2.206  1.00 27.85
ATOM     23  O    ASP A   6      25.111   28.008    2.145  1.00 34.48
ATOM     24  N    CYS A   7      24.037   26.223    2.944  1.00 26.83
ATOM     26  CA   CYS A   7      23.114   27.012    3.728  1.00 23.80
ATOM     27  C    CYS A   7      23.145   26.405    5.111  1.00 25.08
ATOM     28  O    CYS A   7      22.891   25.216    5.263  1.00 31.97
ATOM     29  CB   CYS A   7      21.732   26.874    3.128  1.00 23.85
ATOM     30  SG   CYS A   7      20.877   28.447    2.960  1.00 20.60
ATOM     31  N    PRO A   8      23.470   27.203    6.140  1.00 21.00
ATOM     32  CD   PRO A   8      23.759   28.639    6.059  1.00 16.13
ATOM     33  CA   PRO A   8      23.552   26.750    7.529  1.00 15.31
ATOM     34  CB   PRO A   8      23.939   28.018    8.275  1.00  9.58
ATOM     35  CG   PRO A   8      23.411   29.089    7.433  1.00 10.03
ATOM     36  C    PRO A   8      22.319   26.094    8.105  1.00 13.60
ATOM     37  O    PRO A   8      21.199   26.562    7.928  1.00 14.69
ATOM     38  N    GLU A   9      22.556   25.001    8.814  1.00 16.38
ATOM     40  CA   GLU A   9      21.504   24.213    9.442  1.00 15.91
ATOM     41  CB   GLU A   9      22.142   23.198   10.383  1.00 18.60
ATOM     42  CG   GLU A   9      21.186   22.216   11.014  1.00 26.18
ATOM     43  CD   GLU A   9      21.907   21.063   11.712  1.00 34.42
ATOM     44  OE1  GLU A   9      23.076   21.254   12.129  1.00 29.16
ATOM     45  OE2  GLU A   9      21.307   19.964   11.835  1.00 37.79
ATOM     46  C    GLU A   9      20.578   25.099   10.215  1.00 12.82
ATOM     47  O    GLU A   9      20.963   26.188   10.606  1.00 15.43
ATOM     48  N    CYS A  10      19.345   24.659   10.395  1.00 22.69
ATOM     50  CA   CYS A  10      18.381   25.432   11.167  1.00 27.79
ATOM     51  C    CYS A  10      18.597   25.020   12.620  1.00 26.29
ATOM     52  O    CYS A  10      18.304   23.880   12.961  1.00 31.48
ATOM     53  CB   CYS A  10      16.972   25.079   10.692  1.00 22.23
ATOM     54  SG   CYS A  10      15.579   25.553   11.754  1.00 13.97
```

FIG. 1A-1

| | | | | | | | | | |
|---|---|---|---|---|---|---|---|---|---|
| ATOM | 55  | N   | THR | A | 11 | 19.180 | 25.894 | 13.447 | 1.00 17.95 |
| ATOM | 57  | CA  | THR | A | 11 | 19.435 | 25.568 | 14.861 | 1.00 23.72 |
| ATOM | 58  | CB  | THR | A | 11 | 20.815 | 24.947 | 15.078 | 1.00 25.54 |
| ATOM | 59  | OG1 | THR | A | 11 | 21.804 | 25.722 | 14.389 | 1.00 31.82 |
| ATOM | 61  | CG2 | THR | A | 11 | 20.842 | 23.513 | 14.638 | 1.00 31.83 |
| ATOM | 62  | C   | THR | A | 11 | 19.370 | 26.724 | 15.860 | 1.00 29.43 |
| ATOM | 63  | O   | THR | A | 11 | 18.970 | 27.843 | 15.529 | 1.00 30.12 |
| ATOM | 64  | N   | LEU | A | 12 | 19.799 | 26.442 | 17.091 | 1.00 32.13 |
| ATOM | 66  | CA  | LEU | A | 12 | 19.812 | 27.428 | 18.162 | 1.00 24.59 |
| ATOM | 67  | CB  | LEU | A | 12 | 19.724 | 26.727 | 19.506 | 1.00 15.99 |
| ATOM | 68  | CG  | LEU | A | 12 | 18.361 | 26.134 | 19.786 | 1.00 15.80 |
| ATOM | 69  | CD1 | LEU | A | 12 | 18.460 | 25.081 | 20.811 | 1.00 16.53 |
| ATOM | 70  | CD2 | LEU | A | 12 | 17.454 | 27.230 | 20.255 | 1.00 23.40 |
| ATOM | 71  | C   | LEU | A | 12 | 21.065 | 28.262 | 18.150 | 1.00 22.60 |
| ATOM | 72  | O   | LEU | A | 12 | 22.164 | 27.735 | 18.129 | 1.00 20.32 |
| ATOM | 73  | N   | GLN | A | 13 | 20.891 | 29.572 | 18.172 | 1.00 21.12 |
| ATOM | 75  | CA  | GLN | A | 13 | 22.016 | 30.488 | 18.217 | 1.00 18.54 |
| ATOM | 76  | CB  | GLN | A | 13 | 22.118 | 31.270 | 16.922 | 1.00 11.43 |
| ATOM | 77  | CG  | GLN | A | 13 | 23.456 | 31.116 | 16.267 | 1.00 20.23 |
| ATOM | 78  | CD  | GLN | A | 13 | 23.737 | 29.687 | 15.916 | 1.00 21.45 |
| ATOM | 79  | OE1 | GLN | A | 13 | 23.760 | 29.315 | 14.745 | 1.00 30.73 |
| ATOM | 80  | NE2 | GLN | A | 13 | 23.950 | 28.869 | 16.925 | 1.00 26.88 |
| ATOM | 83  | C   | GLN | A | 13 | 21.848 | 31.438 | 19.398 | 1.00 20.90 |
| ATOM | 84  | O   | GLN | A | 13 | 20.770 | 31.541 | 19.978 | 1.00 27.52 |
| ATOM | 85  | N   | GLU | A | 14 | 22.913 | 32.115 | 19.788 | 1.00 18.16 |
| ATOM | 87  | CA  | GLU | A | 14 | 22.803 | 33.040 | 20.899 | 1.00 20.72 |
| ATOM | 88  | CB  | GLU | A | 14 | 24.142 | 33.173 | 21.602 | 1.00 30.14 |
| ATOM | 89  | CG  | GLU | A | 14 | 24.546 | 31.976 | 22.383 | 1.00 33.68 |
| ATOM | 90  | CD  | GLU | A | 14 | 25.306 | 32.359 | 23.617 | 1.00 34.63 |
| ATOM | 91  | OE1 | GLU | A | 14 | 26.200 | 31.589 | 24.030 | 1.00 42.36 |
| ATOM | 92  | OE2 | GLU | A | 14 | 24.999 | 33.433 | 24.176 | 1.00 35.26 |
| ATOM | 93  | C   | GLU | A | 14 | 22.387 | 34.422 | 20.443 | 1.00 19.04 |
| ATOM | 94  | O   | GLU | A | 14 | 23.120 | 35.041 | 19.694 | 1.00 19.45 |
| ATOM | 95  | N   | ASN | A | 15 | 21.224 | 34.907 | 20.858 | 1.00 20.72 |
| ATOM | 97  | CA  | ASN | A | 15 | 20.823 | 36.258 | 20.486 | 1.00 22.26 |
| ATOM | 98  | CB  | ASN | A | 15 | 19.367 | 36.502 | 20.848 | 1.00 19.80 |
| ATOM | 99  | CG  | ASN | A | 15 | 18.947 | 37.933 | 20.602 | 1.00 27.06 |
| ATOM | 100 | OD1 | ASN | A | 15 | 19.774 | 38.854 | 20.621 | 1.00 22.28 |
| ATOM | 101 | ND2 | ASN | A | 15 | 17.652 | 38.139 | 20.402 | 1.00 26.67 |
| ATOM | 104 | C   | ASN | A | 15 | 21.760 | 37.145 | 21.318 | 1.00 24.04 |
| ATOM | 105 | O   | ASN | A | 15 | 21.524 | 37.381 | 22.503 | 1.00 26.64 |
| ATOM | 106 | N   | PRO | A | 16 | 22.775 | 37.732 | 20.675 | 1.00 23.53 |
| ATOM | 107 | CD  | PRO | A | 16 | 22.651 | 37.939 | 19.225 | 1.00 24.53 |
| ATOM | 108 | CA  | PRO | A | 16 | 23.833 | 38.597 | 21.206 | 1.00 25.46 |
| ATOM | 109 | CB  | PRO | A | 16 | 24.635 | 38.909 | 19.970 | 1.00 25.57 |
| ATOM | 110 | CG  | PRO | A | 16 | 23.541 | 39.126 | 18.987 | 1.00 27.64 |
| ATOM | 111 | C   | PRO | A | 16 | 23.455 | 39.876 | 21.919 | 1.00 25.16 |
| ATOM | 112 | O   | PRO | A | 16 | 24.275 | 40.429 | 22.647 | 1.00 22.83 |
| ATOM | 113 | N   | PHE | A | 17 | 22.250 | 40.371 | 21.672 | 1.00 20.75 |

FIG. 1A-2

| ATOM | 115 | CA  | PHE | A | 17 | 21.787 | 41.602 | 22.296 | 1.00 | 21.34 |
|------|-----|-----|-----|---|----|--------|--------|--------|------|-------|
| ATOM | 116 | CB  | PHE | A | 17 | 20.954 | 42.395 | 21.275 | 1.00 | 22.54 |
| ATOM | 117 | CG  | PHE | A | 17 | 20.308 | 43.653 | 21.815 | 1.00 | 23.49 |
| ATOM | 118 | CD1 | PHE | A | 17 | 21.045 | 44.816 | 21.994 | 1.00 | 28.50 |
| ATOM | 119 | CD2 | PHE | A | 17 | 18.941 | 43.692 | 22.076 | 1.00 | 24.45 |
| ATOM | 120 | CE1 | PHE | A | 17 | 20.431 | 46.004 | 22.421 | 1.00 | 22.39 |
| ATOM | 121 | CE2 | PHE | A | 17 | 18.329 | 44.869 | 22.500 | 1.00 | 24.04 |
| ATOM | 122 | CZ  | PHE | A | 17 | 19.081 | 46.028 | 22.671 | 1.00 | 18.74 |
| ATOM | 123 | C   | PHE | A | 17 | 21.017 | 41.347 | 23.615 | 1.00 | 24.71 |
| ATOM | 124 | O   | PHE | A | 17 | 21.190 | 42.095 | 24.574 | 1.00 | 28.37 |
| ATOM | 125 | N   | PHE | A | 18 | 20.219 | 40.276 | 23.683 | 1.00 | 26.02 |
| ATOM | 127 | CA  | PHE | A | 18 | 19.433 | 39.961 | 24.885 | 1.00 | 24.30 |
| ATOM | 128 | CB  | PHE | A | 18 | 18.051 | 39.409 | 24.515 | 1.00 | 24.88 |
| ATOM | 129 | CG  | PHE | A | 18 | 17.189 | 40.375 | 23.767 | 1.00 | 30.30 |
| ATOM | 130 | CD1 | PHE | A | 18 | 16.546 | 41.411 | 24.429 | 1.00 | 35.29 |
| ATOM | 131 | CD2 | PHE | A | 18 | 17.038 | 40.268 | 22.398 | 1.00 | 27.01 |
| ATOM | 132 | CE1 | PHE | A | 18 | 15.771 | 42.330 | 23.736 | 1.00 | 27.98 |
| ATOM | 133 | CE2 | PHE | A | 18 | 16.266 | 41.181 | 21.702 | 1.00 | 32.65 |
| ATOM | 134 | CZ  | PHE | A | 18 | 15.630 | 42.217 | 22.375 | 1.00 | 22.63 |
| ATOM | 135 | C   | PHE | A | 18 | 20.107 | 38.962 | 25.808 | 1.00 | 26.89 |
| ATOM | 136 | O   | PHE | A | 18 | 19.484 | 38.427 | 26.724 | 1.00 | 27.29 |
| ATOM | 137 | N   | SER | A | 19 | 21.373 | 38.681 | 25.584 | 1.00 | 30.54 |
| ATOM | 139 | CA  | SER | A | 19 | 22.011 | 37.721 | 26.453 | 1.00 | 36.49 |
| ATOM | 140 | CB  | SER | A | 19 | 22.944 | 36.820 | 25.649 | 1.00 | 33.44 |
| ATOM | 141 | OG  | SER | A | 19 | 22.211 | 36.003 | 24.738 | 1.00 | 26.62 |
| ATOM | 143 | C   | SER | A | 19 | 22.738 | 38.339 | 27.640 | 1.00 | 44.85 |
| ATOM | 144 | O   | SER | A | 19 | 23.350 | 39.412 | 27.540 | 1.00 | 54.67 |
| ATOM | 145 | N   | GLN | A | 20 | 22.557 | 37.705 | 28.790 | 1.00 | 47.82 |
| ATOM | 147 | CA  | GLN | A | 20 | 23.218 | 38.095 | 30.030 | 1.00 | 42.57 |
| ATOM | 148 | CB  | GLN | A | 20 | 22.284 | 37.901 | 31.225 | 1.00 | 50.51 |
| ATOM | 149 | CG  | GLN | A | 20 | 20.909 | 38.520 | 31.077 | 1.00 | 59.36 |
| ATOM | 150 | CD  | GLN | A | 20 | 20.943 | 40.032 | 31.121 | 1.00 | 64.88 |
| ATOM | 151 | OE1 | GLN | A | 20 | 21.889 | 40.665 | 30.629 | 1.00 | 66.72 |
| ATOM | 152 | NE2 | GLN | A | 20 | 19.916 | 40.628 | 31.733 | 1.00 | 65.48 |
| ATOM | 155 | C   | GLN | A | 20 | 24.275 | 37.008 | 30.091 | 1.00 | 41.71 |
| ATOM | 156 | O   | GLN | A | 20 | 24.035 | 35.892 | 29.613 | 1.00 | 40.08 |
| ATOM | 157 | N   | PRO | A | 21 | 25.459 | 37.297 | 30.655 | 1.00 | 39.03 |
| ATOM | 158 | CD  | PRO | A | 21 | 26.035 | 38.581 | 31.077 | 1.00 | 38.14 |
| ATOM | 159 | CA  | PRO | A | 21 | 26.477 | 36.245 | 30.716 | 1.00 | 43.48 |
| ATOM | 160 | CB  | PRO | A | 21 | 27.632 | 36.950 | 31.417 | 1.00 | 37.64 |
| ATOM | 161 | CG  | PRO | A | 21 | 27.525 | 38.327 | 30.894 | 1.00 | 32.44 |
| ATOM | 162 | C   | PRO | A | 21 | 25.964 | 35.033 | 31.501 | 1.00 | 45.39 |
| ATOM | 163 | O   | PRO | A | 21 | 26.289 | 33.878 | 31.183 | 1.00 | 46.09 |
| ATOM | 164 | N   | GLY | A | 22 | 25.156 | 35.315 | 32.522 | 1.00 | 45.09 |
| ATOM | 166 | CA  | GLY | A | 22 | 24.567 | 34.256 | 33.323 | 1.00 | 49.52 |
| ATOM | 167 | C   | GLY | A | 22 | 23.487 | 33.503 | 32.551 | 1.00 | 50.71 |
| ATOM | 168 | O   | GLY | A | 22 | 23.620 | 32.286 | 32.319 | 1.00 | 50.54 |
| ATOM | 169 | N   | ALA | A | 23 | 22.447 | 34.229 | 32.119 | 1.00 | 49.51 |
| ATOM | 171 | CA  | ALA | A | 23 | 21.329 | 33.638 | 31.373 | 1.00 | 48.94 |

FIG. 1A-3

| ATOM | 172 | CB | ALA | A | 23 | 20.014 | 33.852 | 32.127 | 1.00 | 56.35 |
| ATOM | 173 | C | ALA | A | 23 | 21.217 | 34.177 | 29.952 | 1.00 | 43.45 |
| ATOM | 174 | O | ALA | A | 23 | 20.972 | 35.367 | 29.749 | 1.00 | 43.15 |
| ATOM | 175 | N | PRO | A | 24 | 21.373 | 33.296 | 28.951 | 1.00 | 38.40 |
| ATOM | 176 | CD | PRO | A | 24 | 21.829 | 31.901 | 29.092 | 1.00 | 30.48 |
| ATOM | 177 | CA | PRO | A | 24 | 21.299 | 33.664 | 27.540 | 1.00 | 36.88 |
| ATOM | 178 | CB | PRO | A | 24 | 22.242 | 32.655 | 26.901 | 1.00 | 30.85 |
| ATOM | 179 | CG | PRO | A | 24 | 21.912 | 31.427 | 27.652 | 1.00 | 27.35 |
| ATOM | 180 | C | PRO | A | 24 | 19.900 | 33.519 | 26.962 | 1.00 | 36.05 |
| ATOM | 181 | O | PRO | A | 24 | 19.011 | 32.944 | 27.612 | 1.00 | 36.53 |
| ATOM | 182 | N | ILE | A | 25 | 19.706 | 34.084 | 25.766 | 1.00 | 25.42 |
| ATOM | 184 | CA | ILE | A | 25 | 18.440 | 33.980 | 25.044 | 1.00 | 20.16 |
| ATOM | 185 | CB | ILE | A | 25 | 17.762 | 35.353 | 24.734 | 1.00 | 17.82 |
| ATOM | 186 | CG2 | ILE | A | 25 | 16.973 | 35.276 | 23.426 | 1.00 | 19.25 |
| ATOM | 187 | CG1 | ILE | A | 25 | 16.737 | 35.702 | 25.812 | 1.00 | 13.14 |
| ATOM | 188 | CD1 | ILE | A | 25 | 17.312 | 35.953 | 27.151 | 1.00 | 22.05 |
| ATOM | 189 | C | ILE | A | 25 | 18.814 | 33.296 | 23.745 | 1.00 | 17.10 |
| ATOM | 190 | O | ILE | A | 25 | 19.654 | 33.788 | 23.011 | 1.00 | 21.82 |
| ATOM | 191 | N | LEU | A | 26 | 18.224 | 32.140 | 23.490 | 1.00 | 16.39 |
| ATOM | 193 | CA | LEU | A | 26 | 18.510 | 31.397 | 22.277 | 1.00 | 19.80 |
| ATOM | 194 | CB | LEU | A | 26 | 18.627 | 29.896 | 22.599 | 1.00 | 18.81 |
| ATOM | 195 | CG | LEU | A | 26 | 19.558 | 29.550 | 23.772 | 1.00 | 21.71 |
| ATOM | 196 | CD1 | LEU | A | 26 | 19.473 | 28.081 | 24.147 | 1.00 | 15.13 |
| ATOM | 197 | CD2 | LEU | A | 26 | 20.980 | 29.926 | 23.429 | 1.00 | 22.65 |
| ATOM | 198 | C | LEU | A | 26 | 17.459 | 31.675 | 21.178 | 1.00 | 19.44 |
| ATOM | 199 | O | LEU | A | 26 | 16.237 | 31.649 | 21.395 | 1.00 | 15.22 |
| ATOM | 200 | N | GLN | A | 27 | 17.951 | 31.905 | 19.977 | 1.00 | 12.29 |
| ATOM | 202 | CA | GLN | A | 27 | 17.091 | 32.204 | 18.865 | 1.00 | 14.41 |
| ATOM | 203 | CB | GLN | A | 27 | 17.411 | 33.613 | 18.416 | 1.00 | 19.64 |
| ATOM | 204 | CG | GLN | A | 27 | 16.469 | 34.189 | 17.427 | 1.00 | 16.64 |
| ATOM | 205 | CD | GLN | A | 27 | 16.958 | 35.505 | 16.949 | 1.00 | 17.96 |
| ATOM | 206 | OE1 | GLN | A | 27 | 18.115 | 35.857 | 17.176 | 1.00 | 20.15 |
| ATOM | 207 | NE2 | GLN | A | 27 | 16.095 | 36.258 | 16.294 | 1.00 | 15.51 |
| ATOM | 210 | C | GLN | A | 27 | 17.325 | 31.222 | 17.725 | 1.00 | 17.95 |
| ATOM | 211 | O | GLN | A | 27 | 18.466 | 30.910 | 17.394 | 1.00 | 13.67 |
| ATOM | 212 | N | CYS | A | 28 | 16.240 | 30.727 | 17.136 | 1.00 | 16.95 |
| ATOM | 214 | CA | CYS | A | 28 | 16.340 | 29.792 | 16.029 | 1.00 | 10.49 |
| ATOM | 215 | C | CYS | A | 28 | 16.668 | 30.595 | 14.781 | 1.00 | 8.03 |
| ATOM | 216 | O | CYS | A | 28 | 15.987 | 31.561 | 14.466 | 1.00 | 11.90 |
| ATOM | 217 | CB | CYS | A | 28 | 15.023 | 29.050 | 15.790 | 1.00 | 14.60 |
| ATOM | 218 | SG | CYS | A | 28 | 14.464 | 27.793 | 16.988 | 1.00 | 23.01 |
| ATOM | 219 | N | MET | A | 29 | 17.713 | 30.183 | 14.080 | 1.00 | 2.00 |
| ATOM | 221 | CA | MET | A | 29 | 18.163 | 30.827 | 12.858 | 1.00 | 9.74 |
| ATOM | 222 | CB | MET | A | 29 | 19.309 | 31.792 | 13.158 | 1.00 | 15.89 |
| ATOM | 223 | CG | MET | A | 29 | 18.876 | 33.142 | 13.682 | 1.00 | 27.65 |
| ATOM | 224 | SD | MET | A | 29 | 20.173 | 33.889 | 14.637 | 1.00 | 32.32 |
| ATOM | 225 | CE | MET | A | 29 | 21.545 | 33.593 | 13.617 | 1.00 | 30.24 |
| ATOM | 226 | C | MET | A | 29 | 18.690 | 29.718 | 11.984 | 1.00 | 15.42 |
| ATOM | 227 | O | MET | A | 29 | 19.272 | 28.777 | 12.512 | 1.00 | 20.27 |

FIG. 1A-4

| ATOM | 228 | N   | GLY | A | 30 | 18.466 | 29.790 | 10.669 | 1.00 | 20.52 |
| ATOM | 230 | CA  | GLY | A | 30 | 18.980 | 28.755 | 9.777  | 1.00 | 22.85 |
| ATOM | 231 | C   | GLY | A | 30 | 18.286 | 28.629 | 8.432  | 1.00 | 25.32 |
| ATOM | 232 | O   | GLY | A | 30 | 17.351 | 29.388 | 8.151  | 1.00 | 27.97 |
| ATOM | 233 | N   | CYS | A | 31 | 18.716 | 27.664 | 7.614  | 1.00 | 24.28 |
| ATOM | 235 | CA  | CYS | A | 31 | 18.134 | 27.445 | 6.292  | 1.00 | 26.47 |
| ATOM | 236 | C   | CYS | A | 31 | 17.169 | 26.267 | 6.242  | 1.00 | 32.49 |
| ATOM | 237 | O   | CYS | A | 31 | 17.349 | 25.272 | 6.951  | 1.00 | 35.62 |
| ATOM | 238 | CB  | CYS | A | 31 | 19.228 | 27.252 | 5.240  | 1.00 | 25.11 |
| ATOM | 239 | SG  | CYS | A | 31 | 20.186 | 28.754 | 4.837  | 1.00 | 25.81 |
| ATOM | 240 | N   | CYS | A | 32 | 16.142 | 26.401 | 5.402  | 1.00 | 35.42 |
| ATOM | 242 | CA  | CYS | A | 32 | 15.124 | 25.369 | 5.203  | 1.00 | 33.00 |
| ATOM | 243 | C   | CYS | A | 32 | 14.749 | 25.252 | 3.720  | 1.00 | 34.75 |
| ATOM | 244 | O   | CYS | A | 32 | 14.791 | 26.245 | 2.976  | 1.00 | 36.41 |
| ATOM | 245 | CB  | CYS | A | 32 | 13.884 | 25.675 | 6.031  | 1.00 | 30.32 |
| ATOM | 246 | SG  | CYS | A | 32 | 14.187 | 25.615 | 7.812  | 1.00 | 18.65 |
| ATOM | 247 | N   | PHE | A | 33 | 14.357 | 24.047 | 3.308  | 1.00 | 30.28 |
| ATOM | 249 | CA  | PHE | A | 33 | 14.014 | 23.759 | 1.916  | 1.00 | 27.28 |
| ATOM | 250 | CB  | PHE | A | 33 | 13.924 | 22.249 | 1.691  | 1.00 | 25.55 |
| ATOM | 251 | CG  | PHE | A | 33 | 13.646 | 21.878 | 0.273  | 1.00 | 20.29 |
| ATOM | 252 | CD1 | PHE | A | 33 | 12.397 | 21.424 | -0.104 | 1.00 | 22.86 |
| ATOM | 253 | CD2 | PHE | A | 33 | 14.628 | 22.023 | -0.698 | 1.00 | 20.23 |
| ATOM | 254 | CE1 | PHE | A | 33 | 12.130 | 21.123 | -1.429 | 1.00 | 24.09 |
| ATOM | 255 | CE2 | PHE | A | 33 | 14.368 | 21.724 | -2.017 | 1.00 | 21.27 |
| ATOM | 256 | CZ  | PHE | A | 33 | 13.117 | 21.273 | -2.386 | 1.00 | 18.20 |
| ATOM | 257 | C   | PHE | A | 33 | 12.755 | 24.385 | 1.369  | 1.00 | 24.58 |
| ATOM | 258 | O   | PHE | A | 33 | 11.695 | 24.280 | 1.976  | 1.00 | 30.68 |
| ATOM | 259 | N   | SER | A | 34 | 12.859 | 24.948 | 0.173  | 1.00 | 20.47 |
| ATOM | 261 | CA  | SER | A | 34 | 11.715 | 25.562 | -0.495 | 1.00 | 22.27 |
| ATOM | 262 | CB  | SER | A | 34 | 11.564 | 27.032 | -0.105 | 1.00 | 19.74 |
| ATOM | 263 | OG  | SER | A | 34 | 12.783 | 27.736 | -0.228 | 1.00 | 23.46 |
| ATOM | 265 | C   | SER | A | 34 | 11.812 | 25.444 | -2.006 | 1.00 | 28.31 |
| ATOM | 266 | O   | SER | A | 34 | 12.860 | 25.079 | -2.555 | 1.00 | 34.96 |
| ATOM | 267 | N   | ARG | A | 35 | 10.712 | 25.719 | -2.688 | 1.00 | 31.41 |
| ATOM | 269 | CA  | ARG | A | 35 | 10.729 | 25.641 | -4.130 | 1.00 | 29.70 |
| ATOM | 270 | CB  | ARG | A | 35 | 10.805 | 24.187 | -4.619 | 1.00 | 24.55 |
| ATOM | 271 | CG  | ARG | A | 35 | 9.578  | 23.316 | -4.330 | 1.00 | 28.51 |
| ATOM | 272 | CD  | ARG | A | 35 | 9.688  | 21.965 | -5.052 | 1.00 | 27.27 |
| ATOM | 273 | NE  | ARG | A | 35 | 8.673  | 20.987 | -4.656 | 1.00 | 25.30 |
| ATOM | 275 | CZ  | ARG | A | 35 | 8.801  | 19.683 | -4.864 | 1.00 | 32.10 |
| ATOM | 276 | NH1 | ARG | A | 35 | 9.889  | 19.228 | -5.459 | 1.00 | 39.16 |
| ATOM | 279 | NH2 | ARG | A | 35 | 7.863  | 18.834 | -4.471 | 1.00 | 36.93 |
| ATOM | 282 | C   | ARG | A | 35 | 9.565  | 26.350 | -4.767 | 1.00 | 29.20 |
| ATOM | 283 | O   | ARG | A | 35 | 8.528  | 26.587 | -4.142 | 1.00 | 26.14 |
| ATOM | 284 | N   | ALA | A | 36 | 9.795  | 26.735 | -6.013 | 1.00 | 26.71 |
| ATOM | 286 | CA  | ALA | A | 36 | 8.813  | 27.417 | -6.831 | 1.00 | 25.41 |
| ATOM | 287 | CB  | ALA | A | 36 | 9.051  | 28.918 | -6.843 | 1.00 | 19.40 |
| ATOM | 288 | C   | ALA | A | 36 | 8.933  | 26.870 | -8.235 | 1.00 | 26.49 |
| ATOM | 289 | O   | ALA | A | 36 | 10.030 | 26.627 | -8.738 | 1.00 | 33.78 |

FIG. 1A-5

| | | | | | | | | | |
|---|---|---|---|---|---|---|---|---|---|
| ATOM | 290 | N | TYR | A | 37 | 7.786 | 26.628 | -8.836 | 1.00 23.68 |
| ATOM | 292 | CA | TYR | A | 37 | 7.699 | 26.127 | -10.174 | 1.00 22.39 |
| ATOM | 293 | CB | TYR | A | 37 | 7.609 | 24.610 | -10.145 | 1.00 27.50 |
| ATOM | 294 | CG | TYR | A | 37 | 6.560 | 24.114 | -9.206 | 1.00 24.55 |
| ATOM | 295 | CD1 | TYR | A | 37 | 6.904 | 23.587 | -7.977 | 1.00 23.39 |
| ATOM | 296 | CE1 | TYR | A | 37 | 5.932 | 23.208 | -7.059 | 1.00 22.44 |
| ATOM | 297 | CD2 | TYR | A | 37 | 5.217 | 24.246 | -9.511 | 1.00 25.93 |
| ATOM | 298 | CE2 | TYR | A | 37 | 4.240 | 23.877 | -8.610 | 1.00 32.94 |
| ATOM | 299 | CZ | TYR | A | 37 | 4.601 | 23.361 | -7.378 | 1.00 25.54 |
| ATOM | 300 | OH | TYR | A | 37 | 3.622 | 23.030 | -6.471 | 1.00 20.99 |
| ATOM | 302 | C | TYR | A | 37 | 6.384 | 26.733 | -10.580 | 1.00 24.02 |
| ATOM | 303 | O | TYR | A | 37 | 5.613 | 27.165 | -9.721 | 1.00 24.51 |
| ATOM | 304 | N | PRO | A | 38 | 6.096 | 26.775 | -11.882 | 1.00 25.33 |
| ATOM | 305 | CD | PRO | A | 38 | 6.874 | 26.213 | -13.000 | 1.00 18.04 |
| ATOM | 306 | CA | PRO | A | 38 | 4.838 | 27.350 | -12.360 | 1.00 20.80 |
| ATOM | 307 | CB | PRO | A | 38 | 4.957 | 27.192 | -13.868 | 1.00 22.18 |
| ATOM | 308 | CG | PRO | A | 38 | 5.804 | 25.954 | -14.004 | 1.00 20.17 |
| ATOM | 309 | C | PRO | A | 38 | 3.632 | 26.606 | -11.806 | 1.00 21.10 |
| ATOM | 310 | O | PRO | A | 38 | 3.647 | 25.381 | -11.692 | 1.00 21.78 |
| ATOM | 311 | N | THR | A | 39 | 2.599 | 27.355 | -11.445 | 1.00 14.53 |
| ATOM | 313 | CA | THR | A | 39 | 1.393 | 26.778 | -10.889 | 1.00 10.57 |
| ATOM | 314 | CB | THR | A | 39 | 0.353 | 27.865 | -10.543 | 1.00 14.28 |
| ATOM | 315 | OG1 | THR | A | 39 | 0.968 | 28.905 | -9.768 | 1.00 16.46 |
| ATOM | 317 | CG2 | THR | A | 39 | -0.788 | 27.273 | -9.723 | 1.00 10.64 |
| ATOM | 318 | C | THR | A | 39 | 0.802 | 25.852 | -11.920 | 1.00 13.60 |
| ATOM | 319 | O | THR | A | 39 | 0.422 | 26.282 | -12.995 | 1.00 20.24 |
| ATOM | 320 | N | PRO | A | 40 | 0.729 | 24.561 | -11.608 | 1.00 13.48 |
| ATOM | 321 | CD | PRO | A | 40 | 1.075 | 23.988 | -10.306 | 1.00 16.02 |
| ATOM | 322 | CA | PRO | A | 40 | 0.185 | 23.533 | -12.493 | 1.00 13.91 |
| ATOM | 323 | CB | PRO | A | 40 | 0.273 | 22.288 | -11.627 | 1.00 14.59 |
| ATOM | 324 | CG | PRO | A | 40 | 0.167 | 22.835 | -10.249 | 1.00 19.66 |
| ATOM | 325 | C | PRO | A | 40 | -1.256 | 23.829 | -12.919 | 1.00 18.33 |
| ATOM | 326 | O | PRO | A | 40 | -1.991 | 24.491 | -12.184 | 1.00 16.97 |
| ATOM | 327 | N | LEU | A | 41 | -1.672 | 23.290 | -14.066 | 1.00 18.85 |
| ATOM | 329 | CA | LEU | A | 41 | -3.017 | 23.525 | -14.595 | 1.00 21.83 |
| ATOM | 330 | CB | LEU | A | 41 | -3.306 | 22.646 | -15.799 | 1.00 18.53 |
| ATOM | 331 | CG | LEU | A | 41 | -4.733 | 22.955 | -16.286 | 1.00 12.50 |
| ATOM | 332 | CD1 | LEU | A | 41 | -4.704 | 24.297 | -16.992 | 1.00 10.95 |
| ATOM | 333 | CD2 | LEU | A | 41 | -5.297 | 21.865 | -17.177 | 1.00 5.70 |
| ATOM | 334 | C | LEU | A | 41 | -4.180 | 23.335 | -13.648 | 1.00 27.71 |
| ATOM | 335 | O | LEU | A | 41 | -5.029 | 24.216 | -13.515 | 1.00 24.56 |
| ATOM | 336 | N | ARG | A | 42 | -4.312 | 22.117 | -13.140 | 1.00 37.34 |
| ATOM | 338 | CA | ARG | A | 42 | -5.387 | 21.817 | -12.230 | 1.00 38.26 |
| ATOM | 339 | CB | ARG | A | 42 | -5.146 | 20.504 | -11.519 | 1.00 41.07 |
| ATOM | 340 | CG | ARG | A | 42 | -5.946 | 19.392 | -12.127 | 1.00 50.22 |
| ATOM | 341 | CD | ARG | A | 42 | -7.285 | 19.908 | -12.698 | 1.00 49.52 |
| ATOM | 342 | NE | ARG | A | 42 | -8.221 | 20.367 | -11.673 | 1.00 48.40 |
| ATOM | 344 | CZ | ARG | A | 42 | -9.294 | 21.125 | -11.906 | 1.00 52.90 |
| ATOM | 345 | NH1 | ARG | A | 42 | -9.591 | 21.538 | -13.135 | 1.00 49.93 |

FIG. 1A-6

| ATOM | 348 | NH2 | ARG | A | 42 | -10.103 | 21.444 | -10.902 | 1.00 | 53.99 |
| ATOM | 351 | C | ARG | A | 42 | -5.531 | 22.926 | -11.227 | 1.00 | 39.36 |
| ATOM | 352 | O | ARG | A | 42 | -6.608 | 23.489 | -11.080 | 1.00 | 45.54 |
| ATOM | 353 | N | SER | A | 43 | -4.409 | 23.310 | -10.632 | 1.00 | 34.19 |
| ATOM | 355 | CA | SER | A | 43 | -4.382 | 24.379 | -9.649 | 1.00 | 32.22 |
| ATOM | 356 | CB | SER | A | 43 | -2.931 | 24.687 | -9.226 | 1.00 | 39.41 |
| ATOM | 357 | OG | SER | A | 43 | -2.274 | 23.585 | -8.607 | 1.00 | 36.48 |
| ATOM | 359 | C | SER | A | 43 | -5.041 | 25.668 | -10.155 | 1.00 | 29.36 |
| ATOM | 360 | O | SER | A | 43 | -5.619 | 26.410 | -9.369 | 1.00 | 30.35 |
| ATOM | 361 | N | LYS | A | 44 | -4.944 | 25.950 | -11.448 | 1.00 | 23.57 |
| ATOM | 363 | CA | LYS | A | 44 | -5.535 | 27.165 | -11.983 | 1.00 | 25.23 |
| ATOM | 364 | CB | LYS | A | 44 | -4.966 | 27.452 | -13.360 | 1.00 | 28.88 |
| ATOM | 365 | CG | LYS | A | 44 | -3.476 | 27.661 | -13.338 | 1.00 | 27.61 |
| ATOM | 366 | CD | LYS | A | 44 | -3.100 | 28.994 | -13.968 | 1.00 | 29.41 |
| ATOM | 367 | CE | LYS | A | 44 | -2.691 | 28.849 | -15.419 | 1.00 | 25.06 |
| ATOM | 368 | NZ | LYS | A | 44 | -1.461 | 28.016 | -15.567 | 1.00 | 27.49 |
| ATOM | 372 | C | LYS | A | 44 | -7.063 | 27.159 | -12.023 | 1.00 | 27.91 |
| ATOM | 373 | O | LYS | A | 44 | -7.693 | 28.197 | -11.861 | 1.00 | 30.00 |
| ATOM | 374 | N | LYS | A | 45 | -7.660 | 25.988 | -12.194 | 1.00 | 23.62 |
| ATOM | 376 | CA | LYS | A | 45 | -9.106 | 25.860 | -12.243 | 1.00 | 21.77 |
| ATOM | 377 | CB | LYS | A | 45 | -9.451 | 24.582 | -12.987 | 1.00 | 25.25 |
| ATOM | 378 | CG | LYS | A | 45 | -8.735 | 24.472 | -14.304 | 1.00 | 28.98 |
| ATOM | 379 | CD | LYS | A | 45 | -9.088 | 25.679 | -15.151 | 1.00 | 30.98 |
| ATOM | 380 | CE | LYS | A | 45 | -8.477 | 25.664 | -16.525 | 1.00 | 29.09 |
| ATOM | 381 | NZ | LYS | A | 45 | -9.244 | 26.590 | -17.397 | 1.00 | 28.74 |
| ATOM | 385 | C | LYS | A | 45 | -9.585 | 25.762 | -10.815 | 1.00 | 23.82 |
| ATOM | 386 | O | LYS | A | 45 | -10.530 | 25.052 | -10.509 | 1.00 | 26.17 |
| ATOM | 387 | N | THR | A | 46 | -8.975 | 26.546 | -9.947 | 1.00 | 27.06 |
| ATOM | 389 | CA | THR | A | 46 | -9.272 | 26.506 | -8.523 | 1.00 | 25.11 |
| ATOM | 390 | CB | THR | A | 46 | -8.271 | 25.539 | -7.865 | 1.00 | 20.82 |
| ATOM | 391 | OG1 | THR | A | 46 | -8.675 | 24.194 | -8.131 | 1.00 | 29.58 |
| ATOM | 393 | CG2 | THR | A | 46 | -8.121 | 25.772 | -6.379 | 1.00 | 26.66 |
| ATOM | 394 | C | THR | A | 46 | -9.113 | 27.883 | -7.892 | 1.00 | 26.01 |
| ATOM | 395 | O | THR | A | 46 | -9.549 | 28.131 | -6.768 | 1.00 | 30.00 |
| ATOM | 396 | N | MET | A | 47 | -8.572 | 28.805 | -8.666 | 1.00 | 18.79 |
| ATOM | 398 | CA | MET | A | 47 | -8.305 | 30.116 | -8.169 | 1.00 | 13.12 |
| ATOM | 399 | CB | MET | A | 47 | -6.841 | 30.417 | -8.476 | 1.00 | 17.38 |
| ATOM | 400 | CG | MET | A | 47 | -5.883 | 29.382 | -7.896 | 1.00 | 18.84 |
| ATOM | 401 | SD | MET | A | 47 | -4.203 | 29.492 | -8.498 | 1.00 | 17.75 |
| ATOM | 402 | CE | MET | A | 47 | -3.499 | 28.237 | -7.593 | 1.00 | 21.14 |
| ATOM | 403 | C | MET | A | 47 | -9.212 | 31.184 | -8.751 | 1.00 | 13.41 |
| ATOM | 404 | O | MET | A | 47 | -9.549 | 31.128 | -9.923 | 1.00 | 15.10 |
| ATOM | 405 | N | LEU | A | 48 | -9.598 | 32.160 | -7.925 | 1.00 | 16.79 |
| ATOM | 407 | CA | LEU | A | 48 | -10.426 | 33.265 | -8.381 | 1.00 | 13.34 |
| ATOM | 408 | CB | LEU | A | 48 | -11.003 | 34.033 | -7.217 | 1.00 | 16.01 |
| ATOM | 409 | CG | LEU | A | 48 | -12.299 | 34.809 | -7.451 | 1.00 | 15.94 |
| ATOM | 410 | CD1 | LEU | A | 48 | -12.543 | 35.548 | -6.162 | 1.00 | 20.13 |
| ATOM | 411 | CD2 | LEU | A | 48 | -12.261 | 35.788 | -8.628 | 1.00 | 14.20 |
| ATOM | 412 | C | LEU | A | 48 | -9.515 | 34.170 | -9.168 | 1.00 | 14.23 |

FIG. 1A-7

| ATOM | 413 | O   | LEU | A | 48 | -9.967 | 34.932 | -10.003 | 1.00 | 25.01 |
| ATOM | 414 | N   | VAL | A | 49 | -8.240 | 34.180 | -8.808  | 1.00 | 19.84 |
| ATOM | 416 | CA  | VAL | A | 49 | -7.247 | 34.950 | -9.560  | 1.00 | 28.60 |
| ATOM | 417 | CB  | VAL | A | 49 | -6.859 | 36.302 | -8.920  | 1.00 | 26.33 |
| ATOM | 418 | CG1 | VAL | A | 49 | -6.486 | 36.156 | -7.463  | 1.00 | 19.34 |
| ATOM | 419 | CG2 | VAL | A | 49 | -5.691 | 36.880 | -9.698  | 1.00 | 36.09 |
| ATOM | 420 | C   | VAL | A | 49 | -6.019 | 34.061 | -9.734  | 1.00 | 30.45 |
| ATOM | 421 | O   | VAL | A | 49 | -5.269 | 33.828 | -8.787  | 1.00 | 22.31 |
| ATOM | 422 | N   | GLN | A | 50 | -5.858 | 33.517 | -10.936 | 1.00 | 33.69 |
| ATOM | 424 | CA  | GLN | A | 50 | -4.759 | 32.620 | -11.189 | 1.00 | 32.69 |
| ATOM | 425 | CB  | GLN | A | 50 | -4.728 | 32.176 | -12.654 | 1.00 | 41.59 |
| ATOM | 426 | CG  | GLN | A | 50 | -4.560 | 33.289 | -13.683 | 1.00 | 55.33 |
| ATOM | 427 | CD  | GLN | A | 50 | -3.102 | 33.746 | -13.882 | 1.00 | 64.69 |
| ATOM | 428 | OE1 | GLN | A | 50 | -2.313 | 33.097 | -14.600 | 1.00 | 63.91 |
| ATOM | 429 | NE2 | GLN | A | 50 | -2.744 | 34.874 | -13.257 | 1.00 | 72.41 |
| ATOM | 432 | C   | GLN | A | 50 | -3.448 | 33.211 | -10.732 | 1.00 | 28.79 |
| ATOM | 433 | O   | GLN | A | 50 | -3.241 | 34.424 | -10.772 | 1.00 | 28.46 |
| ATOM | 434 | N   | LYS | A | 51 | -2.651 | 32.346 | -10.132 | 1.00 | 25.72 |
| ATOM | 436 | CA  | LYS | A | 51 | -1.338 | 32.692 | -9.643  | 1.00 | 25.33 |
| ATOM | 437 | CB  | LYS | A | 51 | -1.108 | 32.094 | -8.262  | 1.00 | 30.55 |
| ATOM | 438 | CG  | LYS | A | 51 | -2.022 | 32.622 | -7.195  | 1.00 | 34.19 |
| ATOM | 439 | CD  | LYS | A | 51 | -1.763 | 34.086 | -6.937  | 1.00 | 30.35 |
| ATOM | 440 | CE  | LYS | A | 51 | -2.612 | 34.587 | -5.788  | 1.00 | 32.20 |
| ATOM | 441 | NZ  | LYS | A | 51 | -2.287 | 33.876 | -4.527  | 1.00 | 44.76 |
| ATOM | 445 | C   | LYS | A | 51 | -0.491 | 31.939 | -10.613 | 1.00 | 18.66 |
| ATOM | 446 | O   | LYS | A | 51 | -0.660 | 30.746 | -10.758 | 1.00 | 15.68 |
| ATOM | 447 | N   | ASN | A | 52 | 0.410  | 32.612 | -11.291 | 1.00 | 15.82 |
| ATOM | 449 | CA  | ASN | A | 52 | 1.226  | 31.901 | -12.236 | 1.00 | 19.73 |
| ATOM | 450 | CB  | ASN | A | 52 | 1.799  | 32.835 | -13.297 | 1.00 | 26.07 |
| ATOM | 451 | CG  | ASN | A | 52 | 2.682  | 33.926 | -12.723 | 1.00 | 25.87 |
| ATOM | 452 | OD1 | ASN | A | 52 | 2.247  | 34.702 | -11.872 | 1.00 | 25.63 |
| ATOM | 453 | ND2 | ASN | A | 52 | 3.906  | 34.022 | -13.242 | 1.00 | 29.03 |
| ATOM | 455 | C   | ASN | A | 52 | 2.311  | 31.049 | -11.628 | 1.00 | 18.71 |
| ATOM | 456 | O   | ASN | A | 52 | 2.840  | 30.186 | -12.302 | 1.00 | 25.46 |
| ATOM | 457 | N   | VAL | A | 53 | 2.630  | 31.248 | -10.358 | 1.00 | 16.10 |
| ATOM | 459 | CA  | VAL | A | 53 | 3.675  | 30.450 | -9.716  | 1.00 | 16.98 |
| ATOM | 460 | CB  | VAL | A | 53 | 4.968  | 31.277 | -9.468  | 1.00 | 16.91 |
| ATOM | 461 | CG1 | VAL | A | 53 | 5.956  | 30.460 | -8.643  | 1.00 | 12.97 |
| ATOM | 462 | CG2 | VAL | A | 53 | 5.608  | 31.723 | -10.785 | 1.00 | 2.00  |
| ATOM | 463 | C   | VAL | A | 53 | 3.215  | 29.903 | -8.371  | 1.00 | 17.55 |
| ATOM | 464 | O   | VAL | A | 53 | 2.448  | 30.560 | -7.660  | 1.00 | 20.96 |
| ATOM | 465 | N   | THR | A | 54 | 3.673  | 28.707 | -8.027  | 1.00 | 4.27  |
| ATOM | 467 | CA  | THR | A | 54 | 3.319  | 28.104 | -6.756  | 1.00 | 8.76  |
| ATOM | 468 | CB  | THR | A | 54 | 2.664  | 26.747 | -6.942  | 1.00 | 5.74  |
| ATOM | 469 | OG1 | THR | A | 54 | 1.458  | 26.917 | -7.677  | 1.00 | 18.06 |
| ATOM | 471 | CG2 | THR | A | 54 | 2.308  | 26.138 | -5.611  | 1.00 | 10.55 |
| ATOM | 472 | C   | THR | A | 54 | 4.605  | 27.919 | -5.975  | 1.00 | 16.13 |
| ATOM | 473 | O   | THR | A | 54 | 5.634  | 27.626 | -6.581  | 1.00 | 23.42 |
| ATOM | 474 | N   | SER | A | 55 | 4.561  | 28.132 | -4.654  | 1.00 | 15.98 |

FIG. 1A-8

| ATOM | 476 | CA  | SER | A | 55 | 5.731  | 27.974 | -3.792 | 1.00 | 15.29 |
| ATOM | 477 | CB  | SER | A | 55 | 6.151  | 29.304 | -3.157 | 1.00 | 24.32 |
| ATOM | 478 | OG  | SER | A | 55 | 7.275  | 29.153 | -2.295 | 1.00 | 22.37 |
| ATOM | 480 | C   | SER | A | 55 | 5.412  | 27.004 | -2.686 | 1.00 | 19.40 |
| ATOM | 481 | O   | SER | A | 55 | 4.278  | 26.927 | -2.211 | 1.00 | 21.48 |
| ATOM | 482 | N   | GLU | A | 56 | 6.433  | 26.269 | -2.280 | 1.00 | 21.87 |
| ATOM | 484 | CA  | GLU | A | 56 | 6.316  | 25.299 | -1.214 | 1.00 | 21.33 |
| ATOM | 485 | CB  | GLU | A | 56 | 6.486  | 23.912 | -1.787 | 1.00 | 21.15 |
| ATOM | 486 | CG  | GLU | A | 56 | 5.353  | 23.530 | -2.689 | 1.00 | 18.81 |
| ATOM | 487 | CD  | GLU | A | 56 | 5.428  | 22.102 | -3.112 | 1.00 | 22.39 |
| ATOM | 488 | OE1 | GLU | A | 56 | 4.774  | 21.767 | -4.109 | 1.00 | 36.82 |
| ATOM | 489 | OE2 | GLU | A | 56 | 6.133  | 21.304 | -2.461 | 1.00 | 31.19 |
| ATOM | 490 | C   | GLU | A | 56 | 7.426  | 25.609 | -0.236 | 1.00 | 22.35 |
| ATOM | 491 | O   | GLU | A | 56 | 8.588  | 25.515 | -0.612 | 1.00 | 25.55 |
| ATOM | 492 | N   | SER | A | 57 | 7.082  | 25.972 | 1.004  | 1.00 | 22.39 |
| ATOM | 494 | CA  | SER | A | 57 | 8.094  | 26.343 | 1.985  | 1.00 | 24.59 |
| ATOM | 495 | CB  | SER | A | 57 | 8.264  | 27.854 | 1.975  | 1.00 | 21.01 |
| ATOM | 496 | OG  | SER | A | 57 | 7.017  | 28.481 | 2.168  | 1.00 | 27.25 |
| ATOM | 498 | C   | SER | A | 57 | 7.950  | 25.893 | 3.432  | 1.00 | 29.26 |
| ATOM | 499 | O   | SER | A | 57 | 6.858  | 25.920 | 4.010  | 1.00 | 34.87 |
| ATOM | 500 | N   | THR | A | 58 | 9.095  | 25.520 | 4.004  | 1.00 | 23.95 |
| ATOM | 502 | CA  | THR | A | 58 | 9.236  | 25.085 | 5.387  | 1.00 | 22.79 |
| ATOM | 503 | CB  | THR | A | 58 | 10.005 | 23.771 | 5.462  | 1.00 | 28.43 |
| ATOM | 504 | OG1 | THR | A | 58 | 11.305 | 23.947 | 4.886  | 1.00 | 37.26 |
| ATOM | 506 | CG2 | THR | A | 58 | 9.285  | 22.689 | 4.695  | 1.00 | 41.95 |
| ATOM | 507 | C   | THR | A | 58 | 10.135 | 26.178 | 5.956  | 1.00 | 25.66 |
| ATOM | 508 | O   | THR | A | 58 | 10.833 | 26.833 | 5.182  | 1.00 | 22.54 |
| ATOM | 509 | N   | CYS | A | 59 | 10.192 | 26.353 | 7.277  | 1.00 | 28.29 |
| ATOM | 511 | CA  | CYS | A | 59 | 11.031 | 27.401 | 7.833  | 1.00 | 24.29 |
| ATOM | 512 | C   | CYS | A | 59 | 11.567 | 27.223 | 9.206  | 1.00 | 25.75 |
| ATOM | 513 | O   | CYS | A | 59 | 10.962 | 26.568 | 10.044 | 1.00 | 30.13 |
| ATOM | 514 | CB  | CYS | A | 59 | 10.327 | 28.714 | 7.750  | 1.00 | 30.03 |
| ATOM | 515 | SG  | CYS | A | 59 | 10.085 | 29.067 | 6.008  | 1.00 | 39.62 |
| ATOM | 516 | N   | CYS | A | 60 | 12.682 | 27.891 | 9.456  | 1.00 | 24.52 |
| ATOM | 518 | CA  | CYS | A | 60 | 13.347 | 27.772 | 10.727 | 1.00 | 18.19 |
| ATOM | 519 | C   | CYS | A | 60 | 12.592 | 28.503 | 11.781 | 1.00 | 19.81 |
| ATOM | 520 | O   | CYS | A | 60 | 12.572 | 29.734 | 11.814 | 1.00 | 19.32 |
| ATOM | 521 | CB  | CYS | A | 60 | 14.764 | 28.271 | 10.629 | 1.00 | 15.24 |
| ATOM | 522 | SG  | CYS | A | 60 | 15.815 | 27.542 | 11.906 | 1.00 | 14.37 |
| ATOM | 523 | N   | VAL | A | 61 | 11.919 | 27.721 | 12.611 | 1.00 | 19.62 |
| ATOM | 525 | CA  | VAL | A | 61 | 11.113 | 28.252 | 13.695 | 1.00 | 18.28 |
| ATOM | 526 | CB  | VAL | A | 61 | 9.613  | 28.188 | 13.344 | 1.00 | 7.16  |
| ATOM | 527 | CG1 | VAL | A | 61 | 9.319  | 29.091 | 12.183 | 1.00 | 2.00  |
| ATOM | 528 | CG2 | VAL | A | 61 | 9.209  | 26.772 | 13.006 | 1.00 | 4.45  |
| ATOM | 529 | C   | VAL | A | 61 | 11.344 | 27.529 | 15.023 | 1.00 | 19.42 |
| ATOM | 530 | O   | VAL | A | 61 | 11.987 | 26.472 | 15.074 | 1.00 | 18.97 |
| ATOM | 531 | N   | ALA | A | 62 | 10.834 | 28.120 | 16.097 | 1.00 | 11.94 |
| ATOM | 533 | CA  | ALA | A | 62 | 10.967 | 27.530 | 17.409 | 1.00 | 12.84 |
| ATOM | 534 | CB  | ALA | A | 62 | 10.635 | 28.546 | 18.474 | 1.00 | 11.51 |

FIG. 1A-9

| ATOM | 535 | C   | ALA | A | 62 | 10.030 | 26.340 | 17.512 | 1.00 | 13.44 |
|------|-----|-----|-----|---|----|--------|--------|--------|------|-------|
| ATOM | 536 | O   | ALA | A | 62 | 8.864  | 26.400 | 17.112 | 1.00 | 17.23 |
| ATOM | 537 | N   | LYS | A | 63 | 10.574 | 25.217 | 17.947 | 1.00 | 16.76 |
| ATOM | 539 | CA  | LYS | A | 63 | 9.764  | 24.031 | 18.132 | 1.00 | 18.12 |
| ATOM | 540 | CB  | LYS | A | 63 | 10.622 | 22.766 | 18.090 | 1.00 | 23.97 |
| ATOM | 541 | CG  | LYS | A | 63 | 9.794  | 21.490 | 18.062 | 1.00 | 31.17 |
| ATOM | 542 | CD  | LYS | A | 63 | 10.483 | 20.329 | 18.768 | 1.00 | 42.88 |
| ATOM | 543 | CE  | LYS | A | 63 | 9.619  | 19.048 | 18.764 | 1.00 | 48.08 |
| ATOM | 544 | NZ  | LYS | A | 63 | 9.622  | 18.285 | 17.453 | 1.00 | 55.04 |
| ATOM | 548 | C   | LYS | A | 63 | 9.157  | 24.217 | 19.535 | 1.00 | 26.00 |
| ATOM | 549 | O   | LYS | A | 63 | 8.022  | 23.792 | 19.807 | 1.00 | 27.36 |
| ATOM | 550 | N   | SER | A | 64 | 9.892  | 24.905 | 20.409 | 1.00 | 30.84 |
| ATOM | 552 | CA  | SER | A | 64 | 9.435  | 25.158 | 21.770 | 1.00 | 33.76 |
| ATOM | 553 | CB  | SER | A | 64 | 9.873  | 24.012 | 22.671 | 1.00 | 42.03 |
| ATOM | 554 | OG  | SER | A | 64 | 11.220 | 23.662 | 22.391 | 1.00 | 42.77 |
| ATOM | 556 | C   | SER | A | 64 | 10.093 | 26.434 | 22.224 | 1.00 | 34.00 |
| ATOM | 557 | O   | SER | A | 64 | 11.127 | 26.817 | 21.682 | 1.00 | 41.94 |
| ATOM | 558 | N   | TYR | A | 65 | 9.527  | 27.076 | 23.230 | 1.00 | 32.03 |
| ATOM | 560 | CA  | TYR | A | 65 | 10.094 | 28.312 | 23.727 | 1.00 | 34.19 |
| ATOM | 561 | CB  | TYR | A | 65 | 9.874  | 29.413 | 22.707 | 1.00 | 38.80 |
| ATOM | 562 | CG  | TYR | A | 65 | 8.420  | 29.666 | 22.396 | 1.00 | 41.45 |
| ATOM | 563 | CD1 | TYR | A | 65 | 7.871  | 29.249 | 21.191 | 1.00 | 46.25 |
| ATOM | 564 | CE1 | TYR | A | 65 | 6.541  | 29.513 | 20.881 | 1.00 | 49.86 |
| ATOM | 565 | CD2 | TYR | A | 65 | 7.600  | 30.352 | 23.296 | 1.00 | 41.04 |
| ATOM | 566 | CE2 | TYR | A | 65 | 6.274  | 30.620 | 23.003 | 1.00 | 45.10 |
| ATOM | 567 | CZ  | TYR | A | 65 | 5.748  | 30.200 | 21.790 | 1.00 | 49.23 |
| ATOM | 568 | OH  | TYR | A | 65 | 4.436  | 30.483 | 21.470 | 1.00 | 55.39 |
| ATOM | 570 | C   | TYR | A | 65 | 9.452  | 28.720 | 25.047 | 1.00 | 37.15 |
| ATOM | 571 | O   | TYR | A | 65 | 8.395  | 28.189 | 25.423 | 1.00 | 39.96 |
| ATOM | 572 | N   | ASN | A | 66 | 10.044 | 29.714 | 25.710 | 1.00 | 29.96 |
| ATOM | 574 | CA  | ASN | A | 66 | 9.517  | 30.197 | 26.982 | 1.00 | 30.30 |
| ATOM | 575 | CB  | ASN | A | 66 | 10.458 | 29.833 | 28.139 | 1.00 | 36.68 |
| ATOM | 576 | CG  | ASN | A | 66 | 11.275 | 28.576 | 27.879 | 1.00 | 43.79 |
| ATOM | 577 | OD1 | ASN | A | 66 | 10.731 | 27.529 | 27.514 | 1.00 | 44.90 |
| ATOM | 578 | ND2 | ASN | A | 66 | 12.591 | 28.666 | 28.102 | 1.00 | 45.49 |
| ATOM | 581 | C   | ASN | A | 66 | 9.442  | 31.714 | 26.943 | 1.00 | 33.59 |
| ATOM | 582 | O   | ASN | A | 66 | 10.402 | 32.350 | 26.512 | 1.00 | 36.69 |
| ATOM | 583 | N   | ARG | A | 67 | 8.327  | 32.312 | 27.367 | 1.00 | 36.30 |
| ATOM | 585 | CA  | ARG | A | 67 | 8.270  | 33.772 | 27.403 | 1.00 | 37.52 |
| ATOM | 586 | CB  | ARG | A | 67 | 6.861  | 34.272 | 27.682 | 1.00 | 40.45 |
| ATOM | 587 | CG  | ARG | A | 67 | 6.564  | 35.643 | 27.078 | 1.00 | 51.26 |
| ATOM | 588 | CD  | ARG | A | 67 | 5.936  | 35.465 | 25.698 | 1.00 | 61.22 |
| ATOM | 589 | NE  | ARG | A | 67 | 4.817  | 34.509 | 25.747 | 1.00 | 62.50 |
| ATOM | 591 | CZ  | ARG | A | 67 | 3.998  | 34.217 | 24.732 | 1.00 | 58.65 |
| ATOM | 592 | NH1 | ARG | A | 67 | 4.138  | 34.795 | 23.541 | 1.00 | 51.33 |
| ATOM | 595 | NH2 | ARG | A | 67 | 3.013  | 33.346 | 24.920 | 1.00 | 61.64 |
| ATOM | 598 | C   | ARG | A | 67 | 9.175  | 34.116 | 28.589 | 1.00 | 37.23 |
| ATOM | 599 | O   | ARG | A | 67 | 9.226  | 33.369 | 29.571 | 1.00 | 36.27 |
| ATOM | 600 | N   | VAL | A | 68 | 9.898  | 35.219 | 28.510 | 1.00 | 36.76 |

FIG. 1A-10

| | | | | | | | | | |
|---|---|---|---|---|---|---|---|---|---|
| ATOM | 602 | CA | VAL | A | 68 | 10.796 | 35.577 | 29.593 | 1.00 33.21 |
| ATOM | 603 | CB | VAL | A | 68 | 12.129 | 34.787 | 29.408 | 1.00 27.55 |
| ATOM | 604 | CG1 | VAL | A | 68 | 13.317 | 35.695 | 29.140 | 1.00 29.36 |
| ATOM | 605 | CG2 | VAL | A | 68 | 12.367 | 33.867 | 30.579 | 1.00 16.93 |
| ATOM | 606 | C | VAL | A | 68 | 10.924 | 37.103 | 29.551 | 1.00 37.74 |
| ATOM | 607 | O | VAL | A | 68 | 10.431 | 37.715 | 28.607 | 1.00 38.01 |
| ATOM | 608 | N | THR | A | 69 | 11.486 | 37.729 | 30.586 | 1.00 39.94 |
| ATOM | 610 | CA | THR | A | 69 | 11.615 | 39.195 | 30.612 | 1.00 37.84 |
| ATOM | 611 | CB | THR | A | 69 | 10.855 | 39.759 | 31.816 | 1.00 39.12 |
| ATOM | 612 | OG1 | THR | A | 69 | 9.525 | 39.232 | 31.790 | 1.00 34.92 |
| ATOM | 614 | CG2 | THR | A | 69 | 10.764 | 41.276 | 31.753 | 1.00 43.92 |
| ATOM | 615 | C | THR | A | 69 | 13.066 | 39.735 | 30.522 | 1.00 39.59 |
| ATOM | 616 | O | THR | A | 69 | 13.358 | 40.706 | 29.801 | 1.00 41.23 |
| ATOM | 617 | N | VAL | A | 70 | 13.963 | 39.119 | 31.279 | 1.00 38.41 |
| ATOM | 619 | CA | VAL | A | 70 | 15.400 | 39.434 | 31.272 | 1.00 40.65 |
| ATOM | 620 | CB | VAL | A | 70 | 16.088 | 38.708 | 30.071 | 1.00 33.48 |
| ATOM | 621 | CG1 | VAL | A | 70 | 15.682 | 39.326 | 28.725 | 1.00 20.28 |
| ATOM | 622 | CG2 | VAL | A | 70 | 17.598 | 38.670 | 30.274 | 1.00 38.62 |
| ATOM | 623 | C | VAL | A | 70 | 16.057 | 40.837 | 31.514 | 1.00 42.59 |
| ATOM | 624 | O | VAL | A | 70 | 16.556 | 41.094 | 32.626 | 1.00 48.83 |
| ATOM | 625 | N | MET | A | 71 | 16.103 | 41.722 | 30.515 | 1.00 36.63 |
| ATOM | 627 | CA | MET | A | 71 | 16.779 | 43.006 | 30.703 | 1.00 36.51 |
| ATOM | 628 | CB | MET | A | 71 | 17.531 | 43.420 | 29.448 | 1.00 39.34 |
| ATOM | 629 | CG | MET | A | 71 | 18.783 | 42.598 | 29.229 | 1.00 33.59 |
| ATOM | 630 | SD | MET | A | 71 | 19.582 | 42.884 | 27.642 | 1.00 41.36 |
| ATOM | 631 | CE | MET | A | 71 | 21.390 | 42.515 | 28.057 | 1.00 29.64 |
| ATOM | 632 | C | MET | A | 71 | 15.905 | 44.116 | 31.202 | 1.00 39.43 |
| ATOM | 633 | O | MET | A | 71 | 15.945 | 45.254 | 30.721 | 1.00 35.47 |
| ATOM | 634 | N | GLY | A | 72 | 15.189 | 43.772 | 32.259 | 1.00 46.98 |
| ATOM | 636 | CA | GLY | A | 72 | 14.278 | 44.689 | 32.900 | 1.00 50.28 |
| ATOM | 637 | C | GLY | A | 72 | 13.358 | 45.368 | 31.919 | 1.00 45.52 |
| ATOM | 638 | O | GLY | A | 72 | 13.622 | 46.512 | 31.573 | 1.00 50.48 |
| ATOM | 639 | N | GLY | A | 73 | 12.338 | 44.665 | 31.422 | 1.00 37.94 |
| ATOM | 641 | CA | GLY | A | 73 | 11.417 | 45.300 | 30.498 | 1.00 38.61 |
| ATOM | 642 | C | GLY | A | 73 | 11.052 | 44.592 | 29.214 | 1.00 41.40 |
| ATOM | 643 | O | GLY | A | 73 | 9.942 | 44.759 | 28.720 | 1.00 48.91 |
| ATOM | 644 | N | PHE | A | 74 | 11.986 | 43.870 | 28.618 | 1.00 44.40 |
| ATOM | 646 | CA | PHE | A | 74 | 11.673 | 43.163 | 27.388 | 1.00 41.28 |
| ATOM | 647 | CB | PHE | A | 74 | 12.944 | 42.795 | 26.650 | 1.00 28.20 |
| ATOM | 648 | CG | PHE | A | 74 | 13.753 | 43.968 | 26.259 | 1.00 26.05 |
| ATOM | 649 | CD1 | PHE | A | 74 | 14.876 | 44.321 | 26.980 | 1.00 26.24 |
| ATOM | 650 | CD2 | PHE | A | 74 | 13.407 | 44.721 | 25.153 | 1.00 20.63 |
| ATOM | 651 | CE1 | PHE | A | 74 | 15.651 | 45.415 | 26.593 | 1.00 29.58 |
| ATOM | 652 | CE2 | PHE | A | 74 | 14.179 | 45.815 | 24.763 | 1.00 20.99 |
| ATOM | 653 | CZ | PHE | A | 74 | 15.300 | 46.163 | 25.481 | 1.00 15.08 |
| ATOM | 654 | C | PHE | A | 74 | 10.931 | 41.906 | 27.776 | 1.00 44.38 |
| ATOM | 655 | O | PHE | A | 74 | 11.055 | 41.450 | 28.903 | 1.00 46.91 |
| ATOM | 656 | N | LYS | A | 75 | 10.114 | 41.382 | 26.871 | 1.00 44.00 |
| ATOM | 658 | CA | LYS | A | 75 | 9.369 | 40.152 | 27.131 | 1.00 39.77 |

FIG. 1A-11

| ATOM | 659 | CB  | LYS | A | 75 | 7.874  | 40.432 | 27.288 | 1.00 | 36.60 |
| ATOM | 660 | CG  | LYS | A | 75 | 7.532  | 41.506 | 28.303 | 1.00 | 34.05 |
| ATOM | 661 | CD  | LYS | A | 75 | 6.048  | 41.518 | 28.577 | 1.00 | 37.14 |
| ATOM | 662 | CE  | LYS | A | 75 | 5.252  | 41.768 | 27.300 | 1.00 | 42.35 |
| ATOM | 663 | NZ  | LYS | A | 75 | 5.380  | 43.173 | 26.809 | 1.00 | 41.85 |
| ATOM | 667 | C   | LYS | A | 75 | 9.628  | 39.209 | 25.962 | 1.00 | 38.77 |
| ATOM | 668 | O   | LYS | A | 75 | 8.726  | 38.878 | 25.191 | 1.00 | 45.84 |
| ATOM | 669 | N   | VAL | A | 76 | 10.890 | 38.802 | 25.849 | 1.00 | 30.76 |
| ATOM | 671 | CA  | VAL | A | 76 | 11.388 | 37.918 | 24.796 | 1.00 | 21.70 |
| ATOM | 672 | CB  | VAL | A | 76 | 12.917 | 38.101 | 24.648 | 1.00 | 14.00 |
| ATOM | 673 | CG1 | VAL | A | 76 | 13.245 | 39.563 | 24.450 | 1.00 | 18.42 |
| ATOM | 674 | CG2 | VAL | A | 76 | 13.642 | 37.571 | 25.857 | 1.00 | 8.63  |
| ATOM | 675 | C   | VAL | A | 76 | 11.077 | 36.407 | 24.908 | 1.00 | 22.72 |
| ATOM | 676 | O   | VAL | A | 76 | 10.864 | 35.866 | 26.006 | 1.00 | 24.60 |
| ATOM | 677 | N   | GLU | A | 77 | 11.038 | 35.741 | 23.755 | 1.00 | 21.72 |
| ATOM | 679 | CA  | GLU | A | 77 | 10.807 | 34.302 | 23.695 | 1.00 | 26.73 |
| ATOM | 680 | CB  | GLU | A | 77 | 10.075 | 33.924 | 22.430 | 1.00 | 23.21 |
| ATOM | 681 | CG  | GLU | A | 77 | 8.613  | 34.149 | 22.454 | 1.00 | 32.29 |
| ATOM | 682 | CD  | GLU | A | 77 | 7.953  | 33.521 | 21.256 | 1.00 | 40.31 |
| ATOM | 683 | OE1 | GLU | A | 77 | 8.672  | 33.037 | 20.352 | 1.00 | 36.05 |
| ATOM | 684 | OE2 | GLU | A | 77 | 6.709  | 33.495 | 21.220 | 1.00 | 44.96 |
| ATOM | 685 | C   | GLU | A | 77 | 12.141 | 33.573 | 23.673 | 1.00 | 29.47 |
| ATOM | 686 | O   | GLU | A | 77 | 12.951 | 33.791 | 22.776 | 1.00 | 36.59 |
| ATOM | 687 | N   | ASN | A | 78 | 12.352 | 32.684 | 24.633 | 1.00 | 31.44 |
| ATOM | 689 | CA  | ASN | A | 78 | 13.579 | 31.910 | 24.722 | 1.00 | 31.62 |
| ATOM | 690 | CB  | ASN | A | 78 | 13.936 | 31.700 | 26.181 | 1.00 | 26.54 |
| ATOM | 691 | CG  | ASN | A | 78 | 15.376 | 31.346 | 26.377 | 1.00 | 29.20 |
| ATOM | 692 | OD1 | ASN | A | 78 | 16.144 | 31.341 | 25.425 | 1.00 | 29.50 |
| ATOM | 693 | ND2 | ASN | A | 78 | 15.760 | 31.090 | 27.625 | 1.00 | 33.60 |
| ATOM | 695 | C   | ASN | A | 78 | 13.317 | 30.560 | 24.078 | 1.00 | 36.96 |
| ATOM | 696 | O   | ASN | A | 78 | 12.584 | 29.743 | 24.637 | 1.00 | 39.49 |
| ATOM | 697 | N   | HIS | A | 79 | 13.871 | 30.343 | 22.886 | 1.00 | 35.89 |
| ATOM | 699 | CA  | HIS | A | 79 | 13.675 | 29.080 | 22.176 | 1.00 | 29.39 |
| ATOM | 700 | CB  | HIS | A | 79 | 14.108 | 29.175 | 20.719 | 1.00 | 25.45 |
| ATOM | 701 | CG  | HIS | A | 79 | 13.437 | 30.277 | 19.963 | 1.00 | 26.51 |
| ATOM | 702 | CD2 | HIS | A | 79 | 12.421 | 31.102 | 20.305 | 1.00 | 25.94 |
| ATOM | 703 | ND1 | HIS | A | 79 | 13.811 | 30.639 | 18.689 | 1.00 | 31.83 |
| ATOM | 705 | CE1 | HIS | A | 79 | 13.056 | 31.643 | 18.276 | 1.00 | 29.61 |
| ATOM | 706 | NE2 | HIS | A | 79 | 12.204 | 31.941 | 19.238 | 1.00 | 27.71 |
| ATOM | 708 | C   | HIS | A | 79 | 14.484 | 28.019 | 22.858 | 1.00 | 28.63 |
| ATOM | 709 | O   | HIS | A | 79 | 15.487 | 28.310 | 23.504 | 1.00 | 20.47 |
| ATOM | 710 | N   | THR | A | 80 | 14.041 | 26.783 | 22.696 | 1.00 | 28.16 |
| ATOM | 712 | CA  | THR | A | 80 | 14.701 | 25.646 | 23.312 | 1.00 | 29.45 |
| ATOM | 713 | CB  | THR | A | 80 | 13.960 | 25.216 | 24.596 | 1.00 | 25.65 |
| ATOM | 714 | OG1 | THR | A | 80 | 12.552 | 25.099 | 24.330 | 1.00 | 23.23 |
| ATOM | 716 | CG2 | THR | A | 80 | 14.169 | 26.235 | 25.702 | 1.00 | 20.75 |
| ATOM | 717 | C   | THR | A | 80 | 14.733 | 24.467 | 22.360 | 1.00 | 32.84 |
| ATOM | 718 | O   | THR | A | 80 | 15.125 | 23.364 | 22.746 | 1.00 | 40.07 |
| ATOM | 719 | N   | ALA | A | 81 | 14.289 | 24.699 | 21.130 | 1.00 | 33.52 |

FIG. 1A-12

| | | | | | | | | | |
|---|---|---|---|---|---|---|---|---|---|
| ATOM | 721 | CA | ALA | A | 81 | 14.253 | 23.664 | 20.102 | 1.00 30.39 |
| ATOM | 722 | CB | ALA | A | 81 | 13.194 | 22.623 | 20.429 | 1.00 26.74 |
| ATOM | 723 | C | ALA | A | 81 | 13.925 | 24.326 | 18.782 | 1.00 30.20 |
| ATOM | 724 | O | ALA | A | 81 | 13.230 | 25.338 | 18.741 | 1.00 34.98 |
| ATOM | 725 | N | CYS | A | 82 | 14.400 | 23.749 | 17.699 | 1.00 27.62 |
| ATOM | 727 | CA | CYS | A | 82 | 14.130 | 24.332 | 16.420 | 1.00 25.93 |
| ATOM | 728 | C | CYS | A | 82 | 13.783 | 23.253 | 15.440 | 1.00 26.25 |
| ATOM | 729 | O | CYS | A | 82 | 13.900 | 22.062 | 15.750 | 1.00 23.59 |
| ATOM | 730 | CB | CYS | A | 82 | 15.341 | 25.094 | 15.925 | 1.00 20.38 |
| ATOM | 731 | SG | CYS | A | 82 | 15.917 | 26.382 | 17.052 | 1.00 21.87 |
| ATOM | 732 | N | HIS | A | 83 | 13.283 | 23.702 | 14.289 | 1.00 17.07 |
| ATOM | 734 | CA | HIS | A | 83 | 12.897 | 22.861 | 13.171 | 1.00 16.60 |
| ATOM | 735 | CB | HIS | A | 83 | 11.962 | 21.723 | 13.610 | 1.00 11.35 |
| ATOM | 736 | CG | HIS | A | 83 | 10.576 | 22.159 | 13.948 | 1.00 15.21 |
| ATOM | 737 | CD2 | HIS | A | 83 | 9.421 | 21.455 | 14.029 | 1.00 17.00 |
| ATOM | 738 | ND1 | HIS | A | 83 | 10.247 | 23.468 | 14.226 | 1.00 22.86 |
| ATOM | 740 | CE1 | HIS | A | 83 | 8.948 | 23.555 | 14.460 | 1.00 21.76 |
| ATOM | 741 | NE2 | HIS | A | 83 | 8.424 | 22.348 | 14.345 | 1.00 19.89 |
| ATOM | 743 | C | HIS | A | 83 | 12.263 | 23.684 | 12.050 | 1.00 21.21 |
| ATOM | 744 | O | HIS | A | 83 | 11.864 | 24.832 | 12.258 | 1.00 22.75 |
| ATOM | 745 | N | CYS | A | 84 | 12.195 | 23.101 | 10.860 | 1.00 23.63 |
| ATOM | 747 | CA | CYS | A | 84 | 11.601 | 23.772 | 9.721 | 1.00 21.99 |
| ATOM | 748 | C | CYS | A | 84 | 10.110 | 23.428 | 9.670 | 1.00 21.95 |
| ATOM | 749 | O | CYS | A | 84 | 9.745 | 22.272 | 9.523 | 1.00 21.96 |
| ATOM | 750 | CB | CYS | A | 84 | 12.286 | 23.328 | 8.426 | 1.00 18.76 |
| ATOM | 751 | SG | CYS | A | 84 | 14.073 | 23.645 | 8.280 | 1.00 20.05 |
| ATOM | 752 | N | SER | A | 85 | 9.251 | 24.427 | 9.800 | 1.00 22.50 |
| ATOM | 754 | CA | SER | A | 85 | 7.816 | 24.203 | 9.780 | 1.00 25.38 |
| ATOM | 755 | CB | SER | A | 85 | 7.218 | 24.509 | 11.152 | 1.00 30.76 |
| ATOM | 756 | OG | SER | A | 85 | 5.800 | 24.497 | 11.125 | 1.00 37.66 |
| ATOM | 758 | C | SER | A | 85 | 7.225 | 25.137 | 8.773 | 1.00 27.85 |
| ATOM | 759 | O | SER | A | 85 | 7.954 | 25.861 | 8.116 | 1.00 23.91 |
| ATOM | 760 | N | THR | A | 86 | 5.902 | 25.132 | 8.658 | 1.00 33.17 |
| ATOM | 762 | CA | THR | A | 86 | 5.235 | 26.013 | 7.719 | 1.00 36.47 |
| ATOM | 763 | CB | THR | A | 86 | 3.719 | 26.023 | 7.874 | 1.00 40.14 |
| ATOM | 764 | OG1 | THR | A | 86 | 3.168 | 27.046 | 7.026 | 1.00 37.97 |
| ATOM | 766 | CG2 | THR | A | 86 | 3.331 | 26.289 | 9.330 | 1.00 31.72 |
| ATOM | 767 | C | THR | A | 86 | 5.727 | 27.404 | 8.009 | 1.00 36.05 |
| ATOM | 768 | O | THR | A | 86 | 5.738 | 27.858 | 9.156 | 1.00 32.02 |
| ATOM | 769 | N | CYS | A | 87 | 6.147 | 28.072 | 6.952 | 1.00 35.26 |
| ATOM | 771 | CA | CYS | A | 87 | 6.659 | 29.411 | 7.083 | 1.00 35.46 |
| ATOM | 772 | C | CYS | A | 87 | 5.596 | 30.384 | 7.569 | 1.00 39.88 |
| ATOM | 773 | O | CYS | A | 87 | 5.904 | 31.483 | 8.050 | 1.00 37.79 |
| ATOM | 774 | CB | CYS | A | 87 | 7.236 | 29.865 | 5.760 | 1.00 26.24 |
| ATOM | 775 | SG | CYS | A | 87 | 8.839 | 30.646 | 6.061 | 1.00 21.95 |
| ATOM | 776 | N | TYR | A | 88 | 4.347 | 29.950 | 7.431 | 1.00 46.44 |
| ATOM | 778 | CA | TYR | A | 88 | 3.162 | 30.693 | 7.830 | 1.00 51.37 |
| ATOM | 779 | CB | TYR | A | 88 | 2.777 | 30.392 | 9.276 | 1.00 59.02 |
| ATOM | 780 | CG | TYR | A | 88 | 1.297 | 30.529 | 9.431 | 1.00 63.62 |

FIG. 1A-13

| | | | | | | | | | |
|---|---|---|---|---|---|---|---|---|---|
| ATOM | 781 | CD1 | TYR | A | 88 | 0.742 | 31.191 | 10.519 | 1.00 66.17 |
| ATOM | 782 | CE1 | TYR | A | 88 | -0.637 | 31.376 | 10.608 | 1.00 71.54 |
| ATOM | 783 | CD2 | TYR | A | 88 | 0.445 | 30.042 | 8.428 | 1.00 67.55 |
| ATOM | 784 | CE2 | TYR | A | 88 | -0.921 | 30.216 | 8.498 | 1.00 72.23 |
| ATOM | 785 | CZ | TYR | A | 88 | -1.467 | 30.885 | 9.591 | 1.00 73.06 |
| ATOM | 786 | OH | TYR | A | 88 | -2.841 | 31.055 | 9.656 | 1.00 72.73 |
| ATOM | 788 | C | TYR | A | 88 | 3.063 | 32.195 | 7.574 | 1.00 50.99 |
| ATOM | 789 | O | TYR | A | 88 | 3.923 | 32.994 | 7.977 | 1.00 53.34 |
| ATOM | 790 | N | TYR | A | 89 | 1.929 | 32.560 | 6.978 | 1.00 52.53 |
| ATOM | 792 | CA | TYR | A | 89 | 1.601 | 33.940 | 6.610 | 1.00 54.07 |
| ATOM | 793 | CB | TYR | A | 89 | 2.343 | 34.354 | 5.310 | 1.00 54.22 |
| ATOM | 794 | CG | TYR | A | 89 | 2.916 | 33.194 | 4.482 | 1.00 54.03 |
| ATOM | 795 | CD1 | TYR | A | 89 | 2.161 | 32.034 | 4.241 | 1.00 51.63 |
| ATOM | 796 | CE1 | TYR | A | 89 | 2.691 | 30.972 | 3.555 | 1.00 51.09 |
| ATOM | 797 | CD2 | TYR | A | 89 | 4.228 | 33.243 | 3.990 | 1.00 48.21 |
| ATOM | 798 | CE2 | TYR | A | 89 | 4.766 | 32.183 | 3.297 | 1.00 43.17 |
| ATOM | 799 | CZ | TYR | A | 89 | 3.994 | 31.047 | 3.084 | 1.00 50.93 |
| ATOM | 800 | OH | TYR | A | 89 | 4.515 | 29.961 | 2.412 | 1.00 59.29 |
| ATOM | 802 | C | TYR | A | 89 | 0.074 | 34.078 | 6.436 | 1.00 55.32 |
| ATOM | 803 | O | TYR | A | 89 | -0.610 | 33.028 | 6.312 | 1.00 53.18 |
| ATOM | 804 | OT | TYR | A | 89 | -0.422 | 35.230 | 6.454 | 1.00 59.94 |
| ATOM | 805 | CB | GLU | B | 103 | 27.498 | 18.677 | -3.431 | 1.00 50.56 |
| ATOM | 806 | CG | GLU | B | 103 | 28.089 | 17.782 | -4.516 | 1.00 58.98 |
| ATOM | 807 | CD | GLU | B | 103 | 28.947 | 16.651 | -3.933 | 1.00 64.39 |
| ATOM | 808 | OE1 | GLU | B | 103 | 28.447 | 15.922 | -3.033 | 1.00 69.40 |
| ATOM | 809 | OE2 | GLU | B | 103 | 30.127 | 16.510 | -4.357 | 1.00 66.81 |
| ATOM | 810 | C | GLU | B | 103 | 27.985 | 19.842 | -1.290 | 1.00 42.13 |
| ATOM | 811 | O | GLU | B | 103 | 28.267 | 19.082 | -0.355 | 1.00 46.85 |
| ATOM | 814 | N | GLU | B | 103 | 29.832 | 18.923 | -2.532 | 1.00 45.28 |
| ATOM | 816 | CA | GLU | B | 103 | 28.502 | 19.577 | -2.691 | 1.00 46.73 |
| ATOM | 817 | N | PRO | B | 104 | 27.244 | 20.940 | -1.122 | 1.00 33.49 |
| ATOM | 818 | CD | PRO | B | 104 | 26.892 | 21.893 | -2.182 | 1.00 29.71 |
| ATOM | 819 | CA | PRO | B | 104 | 26.666 | 21.355 | 0.154 | 1.00 31.18 |
| ATOM | 820 | CB | PRO | B | 104 | 25.961 | 22.662 | -0.208 | 1.00 26.69 |
| ATOM | 821 | CG | PRO | B | 104 | 26.699 | 23.148 | -1.395 | 1.00 23.79 |
| ATOM | 822 | C | PRO | B | 104 | 25.656 | 20.323 | 0.594 | 1.00 29.73 |
| ATOM | 823 | O | PRO | B | 104 | 25.222 | 19.498 | -0.207 | 1.00 25.48 |
| ATOM | 824 | N | LEU | B | 105 | 25.275 | 20.368 | 1.860 | 1.00 28.82 |
| ATOM | 826 | CA | LEU | B | 105 | 24.290 | 19.421 | 2.349 | 1.00 33.61 |
| ATOM | 827 | CB | LEU | B | 105 | 24.594 | 19.024 | 3.798 | 1.00 39.64 |
| ATOM | 828 | CG | LEU | B | 105 | 25.915 | 18.332 | 4.176 | 1.00 35.60 |
| ATOM | 829 | CD1 | LEU | B | 105 | 26.043 | 16.964 | 3.481 | 1.00 36.38 |
| ATOM | 830 | CD2 | LEU | B | 105 | 27.103 | 19.247 | 3.861 | 1.00 39.51 |
| ATOM | 831 | C | LEU | B | 105 | 22.926 | 20.090 | 2.245 | 1.00 35.67 |
| ATOM | 832 | O | LEU | B | 105 | 21.897 | 19.424 | 2.089 | 1.00 37.18 |
| ATOM | 833 | N | ARG | B | 106 | 22.955 | 21.423 | 2.293 | 1.00 35.43 |
| ATOM | 835 | CA | ARG | B | 106 | 21.769 | 22.276 | 2.221 | 1.00 27.80 |
| ATOM | 836 | CB | ARG | B | 106 | 21.492 | 22.878 | 3.609 | 1.00 19.80 |
| ATOM | 837 | CG | ARG | B | 106 | 21.571 | 21.857 | 4.741 | 1.00 11.51 |

FIG. 1A-14

| | | | | | | | | | |
|---|---|---|---|---|---|---|---|---|---|
| ATOM | 838 | CD | ARG | B | 106 | 21.932 | 22.459 | 6.082 | 1.00 11.12 |
| ATOM | 839 | NE | ARG | B | 106 | 22.223 | 21.428 | 7.081 | 1.00 21.69 |
| ATOM | 841 | CZ | ARG | B | 106 | 21.353 | 20.492 | 7.478 | 1.00 35.25 |
| ATOM | 842 | NH1 | ARG | B | 106 | 21.695 | 19.592 | 8.402 | 1.00 33.82 |
| ATOM | 845 | NH2 | ARG | B | 106 | 20.124 | 20.452 | 6.957 | 1.00 36.80 |
| ATOM | 848 | C | ARG | B | 106 | 22.138 | 23.389 | 1.251 | 1.00 21.15 |
| ATOM | 849 | O | ARG | B | 106 | 22.466 | 24.482 | 1.674 | 1.00 27.94 |
| ATOM | 850 | N | PRO | B | 107 | 22.093 | 23.119 | -0.062 | 1.00 11.75 |
| ATOM | 851 | CD | PRO | B | 107 | 21.561 | 21.875 | -0.644 | 1.00 6.37 |
| ATOM | 852 | CA | PRO | B | 107 | 22.432 | 24.078 | -1.126 | 1.00 14.33 |
| ATOM | 853 | CB | PRO | B | 107 | 22.297 | 23.231 | -2.391 | 1.00 8.93 |
| ATOM | 854 | CG | PRO | B | 107 | 21.206 | 22.297 | -2.043 | 1.00 3.73 |
| ATOM | 855 | C | PRO | B | 107 | 21.583 | 25.351 | -1.208 | 1.00 16.68 |
| ATOM | 856 | O | PRO | B | 107 | 20.365 | 25.287 | -1.147 | 1.00 17.07 |
| ATOM | 857 | N | ARG | B | 108 | 22.216 | 26.511 | -1.331 | 1.00 18.85 |
| ATOM | 859 | CA | ARG | B | 108 | 21.450 | 27.735 | -1.421 | 1.00 19.32 |
| ATOM | 860 | CB | ARG | B | 108 | 22.316 | 28.981 | -1.299 | 1.00 16.26 |
| ATOM | 861 | CG | ARG | B | 108 | 22.212 | 29.634 | 0.055 | 1.00 33.74 |
| ATOM | 862 | CD | ARG | B | 108 | 22.609 | 31.108 | 0.013 | 1.00 46.95 |
| ATOM | 863 | NE | ARG | B | 108 | 22.502 | 31.784 | 1.320 | 1.00 56.68 |
| ATOM | 865 | CZ | ARG | B | 108 | 23.412 | 31.718 | 2.300 | 1.00 58.16 |
| ATOM | 866 | NH1 | ARG | B | 108 | 24.518 | 30.994 | 2.154 | 1.00 60.30 |
| ATOM | 869 | NH2 | ARG | B | 108 | 23.246 | 32.431 | 3.412 | 1.00 57.65 |
| ATOM | 872 | C | ARG | B | 108 | 20.688 | 27.749 | -2.723 | 1.00 21.18 |
| ATOM | 873 | O | ARG | B | 108 | 21.152 | 27.209 | -3.728 | 1.00 18.56 |
| ATOM | 874 | N | CYS | B | 109 | 19.495 | 28.338 | -2.647 | 1.00 23.97 |
| ATOM | 876 | CA | CYS | B | 109 | 18.527 | 28.497 | -3.732 | 1.00 18.05 |
| ATOM | 877 | C | CYS | B | 109 | 19.188 | 28.765 | -5.051 | 1.00 19.62 |
| ATOM | 878 | O | CYS | B | 109 | 19.816 | 29.803 | -5.218 | 1.00 23.92 |
| ATOM | 879 | CB | CYS | B | 109 | 17.585 | 29.667 | -3.393 | 1.00 14.77 |
| ATOM | 880 | SG | CYS | B | 109 | 16.198 | 30.073 | -4.507 | 1.00 8.48 |
| ATOM | 881 | N | ARG | B | 110 | 19.054 | 27.814 | -5.971 | 1.00 16.37 |
| ATOM | 883 | CA | ARG | B | 110 | 19.584 | 27.909 | -7.326 | 1.00 14.76 |
| ATOM | 884 | CB | ARG | B | 110 | 20.971 | 27.276 | -7.423 | 1.00 12.39 |
| ATOM | 885 | CG | ARG | B | 110 | 21.153 | 26.017 | -6.611 | 1.00 17.27 |
| ATOM | 886 | CD | ARG | B | 110 | 20.436 | 24.840 | -7.199 | 1.00 9.36 |
| ATOM | 887 | NE | ARG | B | 110 | 19.549 | 24.198 | -6.230 | 1.00 22.99 |
| ATOM | 889 | CZ | ARG | B | 110 | 19.888 | 23.184 | -5.429 | 1.00 23.82 |
| ATOM | 890 | NH1 | ARG | B | 110 | 21.116 | 22.685 | -5.468 | 1.00 17.42 |
| ATOM | 893 | NH2 | ARG | B | 110 | 18.978 | 22.628 | -4.625 | 1.00 20.55 |
| ATOM | 896 | C | ARG | B | 110 | 18.619 | 27.176 | -8.238 | 1.00 20.49 |
| ATOM | 897 | O | ARG | B | 110 | 17.677 | 26.541 | -7.771 | 1.00 20.41 |
| ATOM | 898 | N | PRO | B | 111 | 18.788 | 27.310 | -9.551 | 1.00 23.29 |
| ATOM | 899 | CD | PRO | B | 111 | 19.604 | 28.279 | -10.296 | 1.00 23.21 |
| ATOM | 900 | CA | PRO | B | 111 | 17.878 | 26.607 | -10.444 | 1.00 20.42 |
| ATOM | 901 | CB | PRO | B | 111 | 18.063 | 27.363 | -11.745 | 1.00 22.17 |
| ATOM | 902 | CG | PRO | B | 111 | 19.487 | 27.771 | -11.682 | 1.00 21.31 |
| ATOM | 903 | C | PRO | B | 111 | 18.265 | 25.140 | -10.589 | 1.00 20.51 |
| ATOM | 904 | O | PRO | B | 111 | 19.444 | 24.827 | -10.719 | 1.00 18.95 |

FIG. 1A-15

| ATOM | 905 | N | ILE | B | 112 | 17.278 | 24.253 | -10.496 | 1.00 | 22.68 |
|------|-----|-----|-----|---|-----|--------|--------|---------|------|-------|
| ATOM | 907 | CA | ILE | B | 112 | 17.469 | 22.806 | -10.656 | 1.00 | 25.31 |
| ATOM | 908 | CB | ILE | B | 112 | 17.092 | 22.006 | -9.407 | 1.00 | 22.36 |
| ATOM | 909 | CG2 | ILE | B | 112 | 18.153 | 22.135 | -8.372 | 1.00 | 17.32 |
| ATOM | 910 | CG1 | ILE | B | 112 | 15.707 | 22.417 | -8.901 | 1.00 | 20.47 |
| ATOM | 911 | CD1 | ILE | B | 112 | 14.811 | 21.261 | -8.543 | 1.00 | 15.04 |
| ATOM | 912 | C | ILE | B | 112 | 16.509 | 22.337 | -11.730 | 1.00 | 31.84 |
| ATOM | 913 | O | ILE | B | 112 | 15.310 | 22.618 | -11.658 | 1.00 | 42.41 |
| ATOM | 914 | N | ASN | B | 113 | 16.997 | 21.595 | -12.709 | 1.00 | 30.77 |
| ATOM | 916 | CA | ASN | B | 113 | 16.088 | 21.152 | -13.748 | 1.00 | 37.57 |
| ATOM | 917 | CB | ASN | B | 113 | 16.800 | 20.838 | -15.073 | 1.00 | 37.34 |
| ATOM | 918 | CG | ASN | B | 113 | 17.983 | 19.942 | -14.890 | 1.00 | 45.16 |
| ATOM | 919 | OD1 | ASN | B | 113 | 18.075 | 19.270 | -13.868 | 1.00 | 59.13 |
| ATOM | 920 | ND2 | ASN | B | 113 | 18.924 | 19.949 | -15.835 | 1.00 | 51.23 |
| ATOM | 922 | C | ASN | B | 113 | 15.220 | 19.998 | -13.280 | 1.00 | 38.29 |
| ATOM | 923 | O | ASN | B | 113 | 15.587 | 19.226 | -12.389 | 1.00 | 37.48 |
| ATOM | 924 | N | ALA | B | 114 | 14.032 | 19.940 | -13.860 | 1.00 | 37.65 |
| ATOM | 926 | CA | ALA | B | 114 | 13.055 | 18.930 | -13.537 | 1.00 | 33.83 |
| ATOM | 927 | CB | ALA | B | 114 | 12.342 | 19.331 | -12.283 | 1.00 | 26.89 |
| ATOM | 928 | C | ALA | B | 114 | 12.070 | 18.832 | -14.703 | 1.00 | 32.38 |
| ATOM | 929 | O | ALA | B | 114 | 12.102 | 19.657 | -15.627 | 1.00 | 36.57 |
| ATOM | 930 | N | THR | B | 115 | 11.260 | 17.778 | -14.707 | 1.00 | 24.88 |
| ATOM | 932 | CA | THR | B | 115 | 10.270 | 17.601 | -15.750 | 1.00 | 22.38 |
| ATOM | 933 | CB | THR | B | 115 | 9.891 | 16.126 | -15.973 | 1.00 | 22.23 |
| ATOM | 934 | OG1 | THR | B | 115 | 8.937 | 15.713 | -14.987 | 1.00 | 27.57 |
| ATOM | 936 | CG2 | THR | B | 115 | 11.107 | 15.235 | -15.895 | 1.00 | 19.62 |
| ATOM | 937 | C | THR | B | 115 | 9.053 | 18.339 | -15.238 | 1.00 | 21.91 |
| ATOM | 938 | O | THR | B | 115 | 8.888 | 18.518 | -14.036 | 1.00 | 21.73 |
| ATOM | 939 | N | LEU | B | 116 | 8.165 | 18.687 | -16.146 | 1.00 | 23.00 |
| ATOM | 941 | CA | LEU | B | 116 | 6.969 | 19.423 | -15.810 | 1.00 | 21.50 |
| ATOM | 942 | CB | LEU | B | 116 | 7.270 | 20.923 | -15.934 | 1.00 | 32.34 |
| ATOM | 943 | CG | LEU | B | 116 | 6.246 | 21.986 | -16.348 | 1.00 | 43.46 |
| ATOM | 944 | CD1 | LEU | B | 116 | 5.153 | 22.168 | -15.301 | 1.00 | 53.15 |
| ATOM | 945 | CD2 | LEU | B | 116 | 6.973 | 23.306 | -16.562 | 1.00 | 43.93 |
| ATOM | 946 | C | LEU | B | 116 | 5.876 | 18.997 | -16.778 | 1.00 | 20.37 |
| ATOM | 947 | O | LEU | B | 116 | 6.128 | 18.806 | -17.985 | 1.00 | 24.92 |
| ATOM | 948 | N | ALA | B | 117 | 4.690 | 18.766 | -16.227 | 1.00 | 12.99 |
| ATOM | 950 | CA | ALA | B | 117 | 3.533 | 18.366 | -17.012 | 1.00 | 13.35 |
| ATOM | 951 | CB | ALA | B | 117 | 2.422 | 17.895 | -16.099 | 1.00 | 13.26 |
| ATOM | 952 | C | ALA | B | 117 | 3.056 | 19.554 | -17.825 | 1.00 | 12.84 |
| ATOM | 953 | O | ALA | B | 117 | 2.949 | 20.678 | -17.310 | 1.00 | 11.98 |
| ATOM | 954 | N | VAL | B | 118 | 2.824 | 19.322 | -19.103 | 1.00 | 9.50 |
| ATOM | 956 | CA | VAL | B | 118 | 2.330 | 20.356 | -19.969 | 1.00 | 11.75 |
| ATOM | 957 | CB | VAL | B | 118 | 3.308 | 20.707 | -21.069 | 1.00 | 7.44 |
| ATOM | 958 | CG1 | VAL | B | 118 | 2.715 | 21.742 | -21.933 | 1.00 | 6.12 |
| ATOM | 959 | CG2 | VAL | B | 118 | 4.583 | 21.238 | -20.496 | 1.00 | 20.96 |
| ATOM | 960 | C | VAL | B | 118 | 1.148 | 19.663 | -20.575 | 1.00 | 20.05 |
| ATOM | 961 | O | VAL | B | 118 | 1.288 | 18.557 | -21.073 | 1.00 | 30.64 |
| ATOM | 962 | N | GLU | B | 119 | -0.029 | 20.263 | -20.446 | 1.00 | 19.27 |

FIG. 1A-16

| | | | | | | | | | |
|---|---|---|---|---|---|---|---|---|---|
| ATOM | 964 | CA | GLU | B | 119 | -1.257 | 19.697 | -20.988 | 1.00 24.72 |
| ATOM | 965 | CB | GLU | B | 119 | -1.871 | 18.726 | -19.998 | 1.00 26.69 |
| ATOM | 966 | CG | GLU | B | 119 | -2.235 | 19.381 | -18.693 | 1.00 37.05 |
| ATOM | 967 | CD | GLU | B | 119 | -2.791 | 18.410 | -17.671 | 1.00 47.20 |
| ATOM | 968 | OE1 | GLU | B | 119 | -3.560 | 17.499 | -18.071 | 1.00 48.15 |
| ATOM | 969 | OE2 | GLU | B | 119 | -2.459 | 18.576 | -16.467 | 1.00 51.44 |
| ATOM | 970 | C | GLU | B | 119 | -2.237 | 20.826 | -21.251 | 1.00 29.69 |
| ATOM | 971 | O | GLU | B | 119 | -2.141 | 21.905 | -20.653 | 1.00 29.20 |
| ATOM | 972 | N | LYS | B | 120 | -3.174 | 20.601 | -22.158 | 1.00 31.84 |
| ATOM | 974 | CA | LYS | B | 120 | -4.130 | 21.641 | -22.447 | 1.00 26.75 |
| ATOM | 975 | CB | LYS | B | 120 | -3.805 | 22.361 | -23.756 | 1.00 27.14 |
| ATOM | 976 | CG | LYS | B | 120 | -4.693 | 23.556 | -24.034 | 1.00 28.96 |
| ATOM | 977 | CD | LYS | B | 120 | -4.285 | 24.280 | -25.286 | 1.00 30.85 |
| ATOM | 978 | CE | LYS | B | 120 | -5.040 | 25.586 | -25.399 | 1.00 38.08 |
| ATOM | 979 | NZ | LYS | B | 120 | -4.352 | 26.582 | -26.276 | 1.00 38.80 |
| ATOM | 983 | C | LYS | B | 120 | -5.532 | 21.118 | -22.475 | 1.00 20.82 |
| ATOM | 984 | O | LYS | B | 120 | -5.795 | 19.966 | -22.793 | 1.00 23.41 |
| ATOM | 985 | N | GLU | B | 121 | -6.423 | 22.009 | -22.098 | 1.00 21.29 |
| ATOM | 987 | CA | GLU | B | 121 | -7.854 | 21.775 | -22.033 | 1.00 28.21 |
| ATOM | 988 | CB | GLU | B | 121 | -8.493 | 22.999 | -21.299 | 1.00 31.99 |
| ATOM | 989 | CG | GLU | B | 121 | -8.082 | 24.419 | -21.867 | 1.00 23.14 |
| ATOM | 990 | CD | GLU | B | 121 | -7.492 | 25.375 | -20.836 | 1.00 14.15 |
| ATOM | 991 | OE1 | GLU | B | 121 | -6.314 | 25.248 | -20.492 | 1.00 15.83 |
| ATOM | 992 | OE2 | GLU | B | 121 | -8.187 | 26.310 | -20.420 | 1.00 16.80 |
| ATOM | 993 | C | GLU | B | 121 | -8.434 | 21.553 | -23.468 | 1.00 31.08 |
| ATOM | 994 | O | GLU | B | 121 | -8.856 | 22.509 | -24.149 | 1.00 35.26 |
| ATOM | 995 | N | GLY | B | 122 | -8.414 | 20.305 | -23.944 | 1.00 28.46 |
| ATOM | 997 | CA | GLY | B | 122 | -8.929 | 20.029 | -25.284 | 1.00 23.40 |
| ATOM | 998 | C | GLY | B | 122 | -8.040 | 19.180 | -26.188 | 1.00 25.90 |
| ATOM | 999 | O | GLY | B | 122 | -8.430 | 18.857 | -27.308 | 1.00 25.97 |
| ATOM | 1000 | N | CYS | B | 123 | -6.832 | 18.859 | -25.724 | 1.00 24.63 |
| ATOM | 1002 | CA | CYS | B | 123 | -5.883 | 18.025 | -26.456 | 1.00 22.55 |
| ATOM | 1003 | C | CYS | B | 123 | -5.880 | 16.669 | -25.792 | 1.00 27.96 |
| ATOM | 1004 | O | CYS | B | 123 | -5.891 | 16.575 | -24.565 | 1.00 31.34 |
| ATOM | 1005 | CB | CYS | B | 123 | -4.512 | 18.610 | -26.358 | 1.00 20.04 |
| ATOM | 1006 | SG | CYS | B | 123 | -4.511 | 20.224 | -27.141 | 1.00 18.46 |
| ATOM | 1007 | N | PRO | B | 124 | -5.845 | 15.596 | -26.589 | 1.00 29.54 |
| ATOM | 1008 | CD | PRO | B | 124 | -5.910 | 15.657 | -28.059 | 1.00 40.04 |
| ATOM | 1009 | CA | PRO | B | 124 | -5.849 | 14.205 | -26.133 | 1.00 26.53 |
| ATOM | 1010 | CB | PRO | B | 124 | -5.753 | 13.428 | -27.443 | 1.00 31.94 |
| ATOM | 1011 | CG | PRO | B | 124 | -6.497 | 14.308 | -28.402 | 1.00 42.71 |
| ATOM | 1012 | C | PRO | B | 124 | -4.789 | 13.743 | -25.136 | 1.00 29.66 |
| ATOM | 1013 | O | PRO | B | 124 | -5.090 | 12.943 | -24.239 | 1.00 26.44 |
| ATOM | 1014 | N | VAL | B | 125 | -3.565 | 14.246 | -25.259 | 1.00 32.88 |
| ATOM | 1016 | CA | VAL | B | 125 | -2.514 | 13.773 | -24.378 | 1.00 31.48 |
| ATOM | 1017 | CB | VAL | B | 125 | -1.590 | 12.769 | -25.135 | 1.00 29.43 |
| ATOM | 1018 | CG1 | VAL | B | 125 | -0.984 | 13.406 | -26.373 | 1.00 27.92 |
| ATOM | 1019 | CG2 | VAL | B | 125 | -0.522 | 12.212 | -24.214 | 1.00 30.97 |
| ATOM | 1020 | C | VAL | B | 125 | -1.707 | 14.817 | -23.627 | 1.00 35.58 |

FIG. 1A-17

| ATOM | 1021 | O | VAL | B | 125 | -1.609 | 15.981 | -24.042 | 1.00 | 37.55 |
| ATOM | 1022 | N | CYS | B | 126 | -1.220 | 14.389 | -22.462 | 1.00 | 37.36 |
| ATOM | 1024 | CA | CYS | B | 126 | -0.410 | 15.209 | -21.581 | 1.00 | 34.35 |
| ATOM | 1025 | C | CYS | B | 126 | 1.010 | 14.829 | -21.841 | 1.00 | 33.24 |
| ATOM | 1026 | O | CYS | B | 126 | 1.286 | 13.666 | -22.128 | 1.00 | 36.75 |
| ATOM | 1027 | CB | CYS | B | 126 | -0.692 | 14.891 | -20.123 | 1.00 | 32.19 |
| ATOM | 1028 | SG | CYS | B | 126 | 0.236 | 16.006 | -19.032 | 1.00 | 43.66 |
| ATOM | 1029 | N | ILE | B | 127 | 1.915 | 15.792 | -21.734 | 1.00 | 31.89 |
| ATOM | 1031 | CA | ILE | B | 127 | 3.322 | 15.508 | -21.952 | 1.00 | 30.58 |
| ATOM | 1032 | CB | ILE | B | 127 | 3.777 | 15.868 | -23.408 | 1.00 | 23.17 |
| ATOM | 1033 | CG2 | ILE | B | 127 | 2.634 | 15.677 | -24.382 | 1.00 | 17.40 |
| ATOM | 1034 | CG1 | ILE | B | 127 | 4.311 | 17.296 | -23.506 | 1.00 | 24.26 |
| ATOM | 1035 | CD1 | ILE | B | 127 | 3.283 | 18.354 | -23.343 | 1.00 | 27.44 |
| ATOM | 1036 | C | ILE | B | 127 | 4.176 | 16.192 | -20.881 | 1.00 | 30.37 |
| ATOM | 1037 | O | ILE | B | 127 | 3.645 | 16.852 | -19.989 | 1.00 | 33.43 |
| ATOM | 1038 | N | THR | B | 128 | 5.486 | 15.982 | -20.935 | 1.00 | 27.15 |
| ATOM | 1040 | CA | THR | B | 128 | 6.405 | 16.572 | -19.974 | 1.00 | 25.34 |
| ATOM | 1041 | CB | THR | B | 128 | 6.893 | 15.525 | -18.994 | 1.00 | 24.03 |
| ATOM | 1042 | OG1 | THR | B | 128 | 7.406 | 14.413 | -19.733 | 1.00 | 29.95 |
| ATOM | 1044 | CG2 | THR | B | 128 | 5.766 | 15.061 | -18.103 | 1.00 | 24.74 |
| ATOM | 1045 | C | THR | B | 128 | 7.634 | 17.128 | -20.691 | 1.00 | 29.59 |
| ATOM | 1046 | O | THR | B | 128 | 8.125 | 16.544 | -21.660 | 1.00 | 25.66 |
| ATOM | 1047 | N | VAL | B | 129 | 8.138 | 18.253 | -20.213 | 1.00 | 30.98 |
| ATOM | 1049 | CA | VAL | B | 129 | 9.314 | 18.826 | -20.827 | 1.00 | 34.42 |
| ATOM | 1050 | CB | VAL | B | 129 | 9.005 | 20.188 | -21.461 | 1.00 | 31.39 |
| ATOM | 1051 | CG1 | VAL | B | 129 | 7.965 | 20.006 | -22.529 | 1.00 | 37.00 |
| ATOM | 1052 | CG2 | VAL | B | 129 | 8.518 | 21.178 | -20.416 | 1.00 | 25.59 |
| ATOM | 1053 | C | VAL | B | 129 | 10.379 | 18.987 | -19.769 | 1.00 | 35.83 |
| ATOM | 1054 | O | VAL | B | 129 | 10.137 | 18.679 | -18.602 | 1.00 | 36.28 |
| ATOM | 1055 | N | ASN | B | 130 | 11.573 | 19.401 | -20.192 | 1.00 | 31.63 |
| ATOM | 1057 | CA | ASN | B | 130 | 12.684 | 19.649 | -19.280 | 1.00 | 25.18 |
| ATOM | 1058 | CB | ASN | B | 130 | 14.024 | 19.163 | -19.878 | 1.00 | 36.73 |
| ATOM | 1059 | CG | ASN | B | 130 | 15.266 | 19.923 | -19.319 | 1.00 | 46.41 |
| ATOM | 1060 | OD1 | ASN | B | 130 | 15.878 | 19.506 | -18.329 | 1.00 | 47.83 |
| ATOM | 1061 | ND2 | ASN | B | 130 | 15.649 | 21.020 | -19.977 | 1.00 | 53.67 |
| ATOM | 1063 | C | ASN | B | 130 | 12.729 | 21.148 | -19.098 | 1.00 | 20.98 |
| ATOM | 1064 | O | ASN | B | 130 | 12.536 | 21.899 | -20.057 | 1.00 | 16.24 |
| ATOM | 1065 | N | THR | B | 131 | 12.837 | 21.578 | -17.852 | 1.00 | 19.47 |
| ATOM | 1067 | CA | THR | B | 131 | 12.976 | 22.992 | -17.571 | 1.00 | 21.19 |
| ATOM | 1068 | CB | THR | B | 131 | 11.701 | 23.698 | -17.171 | 1.00 | 15.26 |
| ATOM | 1069 | OG1 | THR | B | 131 | 10.714 | 22.737 | -16.807 | 1.00 | 13.28 |
| ATOM | 1071 | CG2 | THR | B | 131 | 11.241 | 24.611 | -18.256 | 1.00 | 10.57 |
| ATOM | 1072 | C | THR | B | 131 | 13.823 | 23.072 | -16.368 | 1.00 | 23.10 |
| ATOM | 1073 | O | THR | B | 131 | 14.342 | 22.082 | -15.873 | 1.00 | 24.11 |
| ATOM | 1074 | N | THR | B | 132 | 13.840 | 24.263 | -15.833 | 1.00 | 20.99 |
| ATOM | 1076 | CA | THR | B | 132 | 14.584 | 24.551 | -14.667 | 1.00 | 20.17 |
| ATOM | 1077 | CB | THR | B | 132 | 15.654 | 25.532 | -15.061 | 1.00 | 16.22 |
| ATOM | 1078 | OG1 | THR | B | 132 | 15.090 | 26.459 | -15.989 | 1.00 | 15.64 |
| ATOM | 1080 | CG2 | THR | B | 132 | 16.778 | 24.820 | -15.752 | 1.00 | 12.45 |

FIG. 1A-18

| ATOM | 1081 | C   | THR | B | 132 | 13.568 | 25.198 | -13.742 | 1.00 | 21.42 |
|------|------|-----|-----|---|-----|--------|--------|---------|------|-------|
| ATOM | 1082 | O   | THR | B | 132 | 12.674 | 25.898 | -14.208 | 1.00 | 26.13 |
| ATOM | 1083 | N   | ILE | B | 133 | 13.607 | 24.838 | -12.467 | 1.00 | 18.71 |
| ATOM | 1085 | CA  | ILE | B | 133 | 12.725 | 25.437 | -11.474 | 1.00 | 17.14 |
| ATOM | 1086 | CB  | ILE | B | 133 | 11.681 | 24.442 | -10.903 | 1.00 | 4.36  |
| ATOM | 1087 | CG2 | ILE | B | 133 | 10.771 | 23.972 | -11.976 | 1.00 | 2.10  |
| ATOM | 1088 | CG1 | ILE | B | 133 | 12.352 | 23.232 | -10.291 | 1.00 | 3.76  |
| ATOM | 1089 | CD1 | ILE | B | 133 | 11.353 | 22.266 | -9.750  | 1.00 | 6.63  |
| ATOM | 1090 | C   | ILE | B | 133 | 13.664 | 25.909 | -10.372 | 1.00 | 20.93 |
| ATOM | 1091 | O   | ILE | B | 133 | 14.883 | 25.763 | -10.500 | 1.00 | 21.81 |
| ATOM | 1092 | N   | CYS | B | 134 | 13.126 | 26.539 | -9.335  | 1.00 | 20.11 |
| ATOM | 1094 | CA  | CYS | B | 134 | 13.959 | 26.981 | -8.224  | 1.00 | 19.94 |
| ATOM | 1095 | C   | CYS | B | 134 | 13.718 | 26.101 | -6.997  | 1.00 | 25.21 |
| ATOM | 1096 | O   | CYS | B | 134 | 12.577 | 25.928 | -6.548  | 1.00 | 26.36 |
| ATOM | 1097 | CB  | CYS | B | 134 | 13.685 | 28.432 | -7.888  | 1.00 | 13.18 |
| ATOM | 1098 | SG  | CYS | B | 134 | 14.024 | 29.515 | -9.283  | 1.00 | 16.71 |
| ATOM | 1099 | N   | ALA | B | 135 | 14.783 | 25.483 | -6.510  | 1.00 | 26.07 |
| ATOM | 1101 | CA  | ALA | B | 135 | 14.715 | 24.636 | -5.334  | 1.00 | 27.60 |
| ATOM | 1102 | CB  | ALA | B | 135 | 14.678 | 23.185 | -5.727  | 1.00 | 23.04 |
| ATOM | 1103 | C   | ALA | B | 135 | 15.999 | 24.958 | -4.599  | 1.00 | 29.91 |
| ATOM | 1104 | O   | ALA | B | 135 | 17.015 | 25.249 | -5.223  | 1.00 | 33.60 |
| ATOM | 1105 | N   | GLY | B | 136 | 15.951 | 24.994 | -3.283  | 1.00 | 27.27 |
| ATOM | 1107 | CA  | GLY | B | 136 | 17.158 | 25.313 | -2.570  | 1.00 | 23.61 |
| ATOM | 1108 | C   | GLY | B | 136 | 16.801 | 25.648 | -1.162  | 1.00 | 20.13 |
| ATOM | 1109 | O   | GLY | B | 136 | 15.628 | 25.600 | -0.796  | 1.00 | 26.00 |
| ATOM | 1110 | N   | TYR | B | 137 | 17.822 | 25.928 | -0.364  | 1.00 | 15.37 |
| ATOM | 1112 | CA  | TYR | B | 137 | 17.651 | 26.274 | 1.038   | 1.00 | 14.03 |
| ATOM | 1113 | CB  | TYR | B | 137 | 18.676 | 25.539 | 1.911   | 1.00 | 11.33 |
| ATOM | 1114 | CG  | TYR | B | 137 | 18.401 | 24.064 | 2.094   | 1.00 | 10.79 |
| ATOM | 1115 | CD1 | TYR | B | 137 | 18.863 | 23.115 | 1.177   | 1.00 | 16.61 |
| ATOM | 1116 | CE1 | TYR | B | 137 | 18.643 | 21.733 | 1.373   | 1.00 | 14.58 |
| ATOM | 1117 | CD2 | TYR | B | 137 | 17.709 | 23.606 | 3.204   | 1.00 | 14.25 |
| ATOM | 1118 | CE2 | TYR | B | 137 | 17.478 | 22.229 | 3.411   | 1.00 | 18.22 |
| ATOM | 1119 | CZ  | TYR | B | 137 | 17.949 | 21.308 | 2.496   | 1.00 | 19.21 |
| ATOM | 1120 | OH  | TYR | B | 137 | 17.722 | 19.978 | 2.735   | 1.00 | 22.13 |
| ATOM | 1122 | C   | TYR | B | 137 | 17.823 | 27.783 | 1.151   | 1.00 | 13.27 |
| ATOM | 1123 | O   | TYR | B | 137 | 18.504 | 28.395 | 0.327   | 1.00 | 7.12  |
| ATOM | 1124 | N   | CYS | B | 138 | 17.190 | 28.386 | 2.149   | 1.00 | 14.68 |
| ATOM | 1126 | CA  | CYS | B | 138 | 17.296 | 29.821 | 2.325   | 1.00 | 16.18 |
| ATOM | 1127 | C   | CYS | B | 138 | 17.247 | 30.276 | 3.781   | 1.00 | 17.96 |
| ATOM | 1128 | O   | CYS | B | 138 | 16.620 | 29.619 | 4.621   | 1.00 | 23.79 |
| ATOM | 1129 | CB  | CYS | B | 138 | 16.226 | 30.494 | 1.491   | 1.00 | 17.42 |
| ATOM | 1130 | SG  | CYS | B | 138 | 16.902 | 31.120 | -0.069  | 1.00 | 16.08 |
| ATOM | 1131 | N   | PRO | B | 139 | 17.943 | 31.382 | 4.108   | 1.00 | 16.30 |
| ATOM | 1132 | CD  | PRO | B | 139 | 18.724 | 32.215 | 3.179   | 1.00 | 25.48 |
| ATOM | 1133 | CA  | PRO | B | 139 | 18.010 | 31.948 | 5.453   | 1.00 | 17.30 |
| ATOM | 1134 | CB  | PRO | B | 139 | 19.059 | 33.042 | 5.295   | 1.00 | 12.59 |
| ATOM | 1135 | CG  | PRO | B | 139 | 18.829 | 33.527 | 3.926   | 1.00 | 19.29 |
| ATOM | 1136 | C   | PRO | B | 139 | 16.704 | 32.514 | 5.996   | 1.00 | 19.96 |

FIG. 1A-19

| ATOM | 1137 | O   | PRO B 139 | 16.249 | 33.560 | 5.556  | 1.00 | 24.72 |
|------|------|-----|-----------|--------|--------|--------|------|-------|
| ATOM | 1138 | N   | THR B 140 | 16.106 | 31.823 | 6.957  | 1.00 | 24.45 |
| ATOM | 1140 | CA  | THR B 140 | 14.871 | 32.284 | 7.571  | 1.00 | 29.39 |
| ATOM | 1141 | CB  | THR B 140 | 13.737 | 31.227 | 7.463  | 1.00 | 34.99 |
| ATOM | 1142 | OG1 | THR B 140 | 14.129 | 30.016 | 8.126  | 1.00 | 36.07 |
| ATOM | 1144 | CG2 | THR B 140 | 13.422 | 30.913 | 6.017  | 1.00 | 39.31 |
| ATOM | 1145 | C   | THR B 140 | 15.214 | 32.476 | 9.037  | 1.00 | 28.45 |
| ATOM | 1146 | O   | THR B 140 | 16.350 | 32.246 | 9.443  | 1.00 | 27.88 |
| ATOM | 1147 | N   | MET B 141 | 14.252 | 32.960 | 9.808  | 1.00 | 27.86 |
| ATOM | 1149 | CA  | MET B 141 | 14.409 | 33.137 | 11.245 | 1.00 | 31.23 |
| ATOM | 1150 | CB  | MET B 141 | 15.569 | 34.067 | 11.602 | 1.00 | 33.59 |
| ATOM | 1151 | CG  | MET B 141 | 15.301 | 35.541 | 11.462 | 1.00 | 40.05 |
| ATOM | 1152 | SD  | MET B 141 | 16.761 | 36.453 | 11.984 | 1.00 | 38.29 |
| ATOM | 1153 | CE  | MET B 141 | 18.059 | 35.588 | 11.064 | 1.00 | 42.51 |
| ATOM | 1154 | C   | MET B 141 | 13.117 | 33.666 | 11.835 | 1.00 | 36.98 |
| ATOM | 1155 | O   | MET B 141 | 12.106 | 33.808 | 11.140 | 1.00 | 40.03 |
| ATOM | 1156 | N   | THR B 142 | 13.137 | 33.931 | 13.128 | 1.00 | 41.34 |
| ATOM | 1158 | CA  | THR B 142 | 11.963 | 34.450 | 13.797 | 1.00 | 43.27 |
| ATOM | 1159 | CB  | THR B 142 | 11.207 | 33.346 | 14.563 | 1.00 | 43.90 |
| ATOM | 1160 | OG1 | THR B 142 | 11.602 | 32.062 | 14.063 | 1.00 | 51.91 |
| ATOM | 1162 | CG2 | THR B 142 | 9.698  | 33.516 | 14.399 | 1.00 | 46.01 |
| ATOM | 1163 | C   | THR B 142 | 12.494 | 35.463 | 14.787 | 1.00 | 42.89 |
| ATOM | 1164 | O   | THR B 142 | 13.618 | 35.328 | 15.284 | 1.00 | 44.53 |
| ATOM | 1165 | N   | ARG B 143 | 11.706 | 36.503 | 15.023 | 1.00 | 35.68 |
| ATOM | 1167 | CA  | ARG B 143 | 12.058 | 37.563 | 15.952 | 1.00 | 34.38 |
| ATOM | 1168 | CB  | ARG B 143 | 11.237 | 38.791 | 15.570 | 1.00 | 35.88 |
| ATOM | 1169 | CG  | ARG B 143 | 11.250 | 39.931 | 16.538 | 1.00 | 43.89 |
| ATOM | 1170 | CD  | ARG B 143 | 10.318 | 40.997 | 16.014 | 1.00 | 46.95 |
| ATOM | 1171 | NE  | ARG B 143 | 10.821 | 41.612 | 14.784 | 1.00 | 48.40 |
| ATOM | 1173 | CZ  | ARG B 143 | 10.104 | 41.816 | 13.677 | 1.00 | 51.42 |
| ATOM | 1174 | NH1 | ARG B 143 | 8.825  | 41.447 | 13.614 | 1.00 | 54.50 |
| ATOM | 1177 | NH2 | ARG B 143 | 10.667 | 42.419 | 12.633 | 1.00 | 48.25 |
| ATOM | 1180 | C   | ARG B 143 | 11.740 | 37.077 | 17.378 | 1.00 | 29.39 |
| ATOM | 1181 | O   | ARG B 143 | 10.738 | 36.392 | 17.583 | 1.00 | 30.44 |
| ATOM | 1182 | N   | VAL B 144 | 12.629 | 37.343 | 18.336 | 1.00 | 25.03 |
| ATOM | 1184 | CA  | VAL B 144 | 12.386 | 36.911 | 19.720 | 1.00 | 19.03 |
| ATOM | 1185 | CB  | VAL B 144 | 13.692 | 36.554 | 20.507 | 1.00 | 13.55 |
| ATOM | 1186 | CG1 | VAL B 144 | 14.198 | 35.204 | 20.127 | 1.00 | 5.05  |
| ATOM | 1187 | CG2 | VAL B 144 | 14.768 | 37.611 | 20.294 | 1.00 | 14.80 |
| ATOM | 1188 | C   | VAL B 144 | 11.648 | 37.968 | 20.528 | 1.00 | 23.62 |
| ATOM | 1189 | O   | VAL B 144 | 10.797 | 37.647 | 21.359 | 1.00 | 20.12 |
| ATOM | 1190 | N   | LEU B 145 | 12.005 | 39.227 | 20.300 | 1.00 | 27.60 |
| ATOM | 1192 | CA  | LEU B 145 | 11.416 | 40.328 | 21.030 | 1.00 | 24.30 |
| ATOM | 1193 | CB  | LEU B 145 | 11.850 | 41.658 | 20.443 | 1.00 | 21.25 |
| ATOM | 1194 | CG  | LEU B 145 | 11.334 | 42.867 | 21.218 | 1.00 | 23.75 |
| ATOM | 1195 | CD1 | LEU B 145 | 12.084 | 42.940 | 22.533 | 1.00 | 27.76 |
| ATOM | 1196 | CD2 | LEU B 145 | 11.508 | 44.150 | 20.433 | 1.00 | 26.69 |
| ATOM | 1197 | C   | LEU B 145 | 9.916  | 40.264 | 21.014 | 1.00 | 33.13 |
| ATOM | 1198 | O   | LEU B 145 | 9.319  | 40.215 | 19.942 | 1.00 | 34.66 |

FIG. 1A-20

| ATOM | 1199 | N   | GLN | B | 146 | 9.347  | 40.233 | 22.222 | 1.00 | 42.08 |
| ATOM | 1201 | CA  | GLN | B | 146 | 7.905  | 40.215 | 22.507 | 1.00 | 47.23 |
| ATOM | 1202 | CB  | GLN | B | 146 | 7.461  | 41.578 | 23.089 | 1.00 | 51.70 |
| ATOM | 1203 | CG  | GLN | B | 146 | 7.976  | 41.865 | 24.524 | 1.00 | 51.85 |
| ATOM | 1204 | CD  | GLN | B | 146 | 8.012  | 43.356 | 24.938 | 1.00 | 48.75 |
| ATOM | 1205 | OE1 | GLN | B | 146 | 8.717  | 43.730 | 25.888 | 1.00 | 37.59 |
| ATOM | 1206 | NE2 | GLN | B | 146 | 7.260  | 44.197 | 24.233 | 1.00 | 51.72 |
| ATOM | 1209 | C   | GLN | B | 146 | 7.029  | 39.893 | 21.325 | 1.00 | 52.31 |
| ATOM | 1210 | O   | GLN | B | 146 | 6.342  | 38.872 | 21.315 | 1.00 | 56.97 |
| ATOM | 1211 | N   | GLY | B | 147 | 7.040  | 40.822 | 20.365 | 1.00 | 59.70 |
| ATOM | 1213 | CA  | GLY | B | 147 | 6.266  | 40.721 | 19.135 | 1.00 | 63.15 |
| ATOM | 1214 | C   | GLY | B | 147 | 5.769  | 42.110 | 18.754 | 1.00 | 61.21 |
| ATOM | 1215 | O   | GLY | B | 147 | 5.421  | 42.373 | 17.588 | 1.00 | 57.69 |
| ATOM | 1216 | N   | ALA | B | 148 | 5.773  | 42.999 | 19.756 | 1.00 | 56.64 |
| ATOM | 1218 | CA  | ALA | B | 148 | 5.325  | 44.382 | 19.609 | 1.00 | 55.85 |
| ATOM | 1219 | CB  | ALA | B | 148 | 5.247  | 45.042 | 20.985 | 1.00 | 56.27 |
| ATOM | 1220 | C   | ALA | B | 148 | 6.203  | 45.211 | 18.648 | 1.00 | 56.07 |
| ATOM | 1221 | O   | ALA | B | 148 | 7.016  | 46.044 | 19.083 | 1.00 | 55.42 |
| ATOM | 1222 | N   | LEU | B | 149 | 6.056  | 44.922 | 17.352 | 1.00 | 56.37 |
| ATOM | 1224 | CA  | LEU | B | 149 | 6.774  | 45.568 | 16.246 | 1.00 | 55.06 |
| ATOM | 1225 | CB  | LEU | B | 149 | 8.299  | 45.523 | 16.462 | 1.00 | 47.85 |
| ATOM | 1226 | CG  | LEU | B | 149 | 9.120  | 44.231 | 16.691 | 1.00 | 41.97 |
| ATOM | 1227 | CD1 | LEU | B | 149 | 10.539 | 44.624 | 17.065 | 1.00 | 35.47 |
| ATOM | 1228 | CD2 | LEU | B | 149 | 8.563  | 43.337 | 17.783 | 1.00 | 35.66 |
| ATOM | 1229 | C   | LEU | B | 149 | 6.363  | 44.750 | 15.019 | 1.00 | 60.06 |
| ATOM | 1230 | O   | LEU | B | 149 | 6.837  | 43.633 | 14.825 | 1.00 | 63.79 |
| ATOM | 1231 | N   | PRO | B | 150 | 5.404  | 45.266 | 14.223 | 1.00 | 62.15 |
| ATOM | 1232 | CD  | PRO | B | 150 | 4.881  | 46.626 | 14.415 | 1.00 | 63.27 |
| ATOM | 1233 | CA  | PRO | B | 150 | 4.826  | 44.679 | 12.999 | 1.00 | 58.05 |
| ATOM | 1234 | CB  | PRO | B | 150 | 3.869  | 45.771 | 12.518 | 1.00 | 58.74 |
| ATOM | 1235 | CG  | PRO | B | 150 | 4.545  | 47.026 | 12.989 | 1.00 | 62.27 |
| ATOM | 1236 | C   | PRO | B | 150 | 5.800  | 44.336 | 11.896 | 1.00 | 53.04 |
| ATOM | 1237 | O   | PRO | B | 150 | 6.257  | 45.224 | 11.182 | 1.00 | 53.55 |
| ATOM | 1238 | N   | ALA | B | 151 | 6.050  | 43.047 | 11.712 | 1.00 | 48.30 |
| ATOM | 1240 | CA  | ALA | B | 151 | 6.962  | 42.598 | 10.679 | 1.00 | 48.30 |
| ATOM | 1241 | CB  | ALA | B | 151 | 8.323  | 43.285 | 10.839 | 1.00 | 49.51 |
| ATOM | 1242 | C   | ALA | B | 151 | 7.096  | 41.085 | 10.772 | 1.00 | 46.52 |
| ATOM | 1243 | O   | ALA | B | 151 | 6.098  | 40.397 | 10.969 | 1.00 | 44.69 |
| ATOM | 1244 | N   | LEU | B | 152 | 8.331  | 40.589 | 10.638 | 1.00 | 47.30 |
| ATOM | 1246 | CA  | LEU | B | 152 | 8.669  | 39.157 | 10.693 | 1.00 | 47.57 |
| ATOM | 1247 | CB  | LEU | B | 152 | 7.949  | 38.522 | 11.913 | 1.00 | 53.73 |
| ATOM | 1248 | CG  | LEU | B | 152 | 8.370  | 37.328 | 12.787 | 1.00 | 53.92 |
| ATOM | 1249 | CD1 | LEU | B | 152 | 7.441  | 37.284 | 13.994 | 1.00 | 55.86 |
| ATOM | 1250 | CD2 | LEU | B | 152 | 8.297  | 36.006 | 12.041 | 1.00 | 53.50 |
| ATOM | 1251 | C   | LEU | B | 152 | 8.343  | 38.398 | 9.367  | 1.00 | 41.11 |
| ATOM | 1252 | O   | LEU | B | 152 | 8.086  | 37.197 | 9.392  | 1.00 | 42.60 |
| ATOM | 1253 | N   | PRO | B | 153 | 8.399  | 39.078 | 8.193  | 1.00 | 33.80 |
| ATOM | 1254 | CD  | PRO | B | 153 | 8.751  | 40.488 | 7.955  | 1.00 | 37.83 |
| ATOM | 1255 | CA  | PRO | B | 153 | 8.096  | 38.426 | 6.903  | 1.00 | 30.10 |

FIG. 1A-21

| | | | | | | | | | |
|---|---|---|---|---|---|---|---|---|---|
| ATOM | 1256 | CB | PRO | B | 153 | 8.087 | 39.600 | 5.913 | 1.00 32.49 |
| ATOM | 1257 | CG | PRO | B | 153 | 7.879 | 40.813 | 6.782 | 1.00 38.95 |
| ATOM | 1258 | C | PRO | B | 153 | 9.111 | 37.375 | 6.454 | 1.00 28.35 |
| ATOM | 1259 | O | PRO | B | 153 | 10.325 | 37.593 | 6.516 | 1.00 29.89 |
| ATOM | 1260 | N | GLN | B | 154 | 8.612 | 36.278 | 5.897 | 1.00 31.98 |
| ATOM | 1262 | CA | GLN | B | 154 | 9.496 | 35.218 | 5.457 | 1.00 28.36 |
| ATOM | 1263 | CB | GLN | B | 154 | 8.971 | 33.871 | 5.909 | 1.00 25.85 |
| ATOM | 1264 | CG | GLN | B | 154 | 8.788 | 33.799 | 7.411 | 1.00 22.58 |
| ATOM | 1265 | CD | GLN | B | 154 | 10.040 | 34.183 | 8.203 | 1.00 28.96 |
| ATOM | 1266 | OE1 | GLN | B | 154 | 10.995 | 34.772 | 7.678 | 1.00 29.64 |
| ATOM | 1267 | NE2 | GLN | B | 154 | 10.037 | 33.840 | 9.486 | 1.00 42.73 |
| ATOM | 1270 | C | GLN | B | 154 | 9.878 | 35.183 | 4.001 | 1.00 26.34 |
| ATOM | 1271 | O | GLN | B | 154 | 9.080 | 35.447 | 3.113 | 1.00 33.22 |
| ATOM | 1272 | N | VAL | B | 155 | 11.126 | 34.825 | 3.792 | 1.00 20.14 |
| ATOM | 1274 | CA | VAL | B | 155 | 11.731 | 34.732 | 2.495 | 1.00 14.01 |
| ATOM | 1275 | CB | VAL | B | 155 | 13.196 | 35.156 | 2.643 | 1.00 9.16 |
| ATOM | 1276 | CG1 | VAL | B | 155 | 13.939 | 34.158 | 3.480 | 1.00 6.37 |
| ATOM | 1277 | CG2 | VAL | B | 155 | 13.859 | 35.314 | 1.321 | 1.00 18.28 |
| ATOM | 1278 | C | VAL | B | 155 | 11.621 | 33.272 | 2.018 | 1.00 21.19 |
| ATOM | 1279 | O | VAL | B | 155 | 11.585 | 32.354 | 2.839 | 1.00 22.39 |
| ATOM | 1280 | N | VAL | B | 156 | 11.537 | 33.065 | 0.701 | 1.00 16.70 |
| ATOM | 1282 | CA | VAL | B | 156 | 11.440 | 31.729 | 0.106 | 1.00 7.88 |
| ATOM | 1283 | CB | VAL | B | 156 | 10.018 | 31.408 | -0.283 | 1.00 4.45 |
| ATOM | 1284 | CG1 | VAL | B | 156 | 9.148 | 31.417 | 0.935 | 1.00 4.94 |
| ATOM | 1285 | CG2 | VAL | B | 156 | 9.521 | 32.402 | -1.289 | 1.00 2.00 |
| ATOM | 1286 | C | VAL | B | 156 | 12.279 | 31.676 | -1.152 | 1.00 12.98 |
| ATOM | 1287 | O | VAL | B | 156 | 12.686 | 32.707 | -1.657 | 1.00 21.99 |
| ATOM | 1288 | N | CYS | B | 157 | 12.545 | 30.483 | -1.659 | 1.00 16.20 |
| ATOM | 1290 | CA | CYS | B | 157 | 13.342 | 30.342 | -2.875 | 1.00 18.85 |
| ATOM | 1291 | C | CYS | B | 157 | 12.410 | 30.660 | -4.042 | 1.00 21.56 |
| ATOM | 1292 | O | CYS | B | 157 | 11.388 | 30.007 | -4.193 | 1.00 24.43 |
| ATOM | 1293 | CB | CYS | B | 157 | 13.874 | 28.921 | -2.941 | 1.00 6.07 |
| ATOM | 1294 | SG | CYS | B | 157 | 14.947 | 28.507 | -4.330 | 1.00 7.40 |
| ATOM | 1295 | N | ASN | B | 158 | 12.756 | 31.649 | -4.866 | 1.00 20.86 |
| ATOM | 1297 | CA | ASN | B | 158 | 11.883 | 32.076 | -5.966 | 1.00 21.41 |
| ATOM | 1298 | CB | ASN | B | 158 | 11.200 | 33.375 | -5.536 | 1.00 27.77 |
| ATOM | 1299 | CG | ASN | B | 158 | 9.826 | 33.568 | -6.156 | 1.00 38.59 |
| ATOM | 1300 | OD1 | ASN | B | 158 | 9.551 | 33.112 | -7.266 | 1.00 43.80 |
| ATOM | 1301 | ND2 | ASN | B | 158 | 8.953 | 34.272 | -5.437 | 1.00 45.21 |
| ATOM | 1304 | C | ASN | B | 158 | 12.592 | 32.311 | -7.301 | 1.00 20.43 |
| ATOM | 1305 | O | ASN | B | 158 | 13.797 | 32.208 | -7.387 | 1.00 15.86 |
| ATOM | 1306 | N | TYR | B | 159 | 11.831 | 32.582 | -8.356 | 1.00 25.92 |
| ATOM | 1308 | CA | TYR | B | 159 | 12.399 | 32.863 | -9.670 | 1.00 28.86 |
| ATOM | 1309 | CB | TYR | B | 159 | 11.304 | 32.951 | -10.737 | 1.00 24.06 |
| ATOM | 1310 | CG | TYR | B | 159 | 10.740 | 31.644 | -11.180 | 1.00 14.45 |
| ATOM | 1311 | CD1 | TYR | B | 159 | 9.594 | 31.141 | -10.606 | 1.00 14.24 |
| ATOM | 1312 | CE1 | TYR | B | 159 | 9.091 | 29.915 | -10.973 | 1.00 13.31 |
| ATOM | 1313 | CD2 | TYR | B | 159 | 11.372 | 30.893 | -12.144 | 1.00 10.71 |
| ATOM | 1314 | CE2 | TYR | B | 159 | 10.879 | 29.663 | -12.519 | 1.00 10.02 |

FIG. 1A-22

| ATOM | 1315 | CZ | TYR B 159 | 9.740 | 29.174 | -11.925 | 1.00 | 12.96 |
|------|------|------|-----------|--------|--------|---------|------|-------|
| ATOM | 1316 | OH | TYR B 159 | 9.277 | 27.918 | -12.235 | 1.00 | 16.01 |
| ATOM | 1318 | C | TYR B 159 | 13.055 | 34.227 | -9.604 | 1.00 | 31.08 |
| ATOM | 1319 | O | TYR B 159 | 12.817 | 34.994 | -8.679 | 1.00 | 31.89 |
| ATOM | 1320 | N | ARG B 160 | 13.842 | 34.546 | -10.621 | 1.00 | 29.81 |
| ATOM | 1322 | CA | ARG B 160 | 14.493 | 35.838 | -10.697 | 1.00 | 24.83 |
| ATOM | 1323 | CB | ARG B 160 | 15.867 | 35.761 | -10.094 | 1.00 | 16.94 |
| ATOM | 1324 | CG | ARG B 160 | 16.464 | 37.076 | -9.853 | 1.00 | 16.41 |
| ATOM | 1325 | CD | ARG B 160 | 17.841 | 36.898 | -9.271 | 1.00 | 23.77 |
| ATOM | 1326 | NE | ARG B 160 | 18.847 | 37.649 | -10.003 | 1.00 | 29.96 |
| ATOM | 1328 | CZ | ARG B 160 | 18.695 | 38.904 | -10.432 | 1.00 | 38.25 |
| ATOM | 1329 | NH1 | ARG B 160 | 17.561 | 39.579 | -10.210 | 1.00 | 40.44 |
| ATOM | 1332 | NH2 | ARG B 160 | 19.701 | 39.510 | -11.065 | 1.00 | 40.69 |
| ATOM | 1335 | C | ARG B 160 | 14.559 | 36.264 | -12.160 | 1.00 | 27.78 |
| ATOM | 1336 | O | ARG B 160 | 14.246 | 37.403 | -12.493 | 1.00 | 28.93 |
| ATOM | 1337 | N | ASP B 161 | 14.976 | 35.365 | -13.040 | 1.00 | 27.45 |
| ATOM | 1339 | CA | ASP B 161 | 14.998 | 35.681 | -14.461 | 1.00 | 28.72 |
| ATOM | 1340 | CB | ASP B 161 | 16.391 | 36.037 | -14.952 | 1.00 | 34.54 |
| ATOM | 1341 | CG | ASP B 161 | 16.711 | 37.498 | -14.751 | 1.00 | 42.20 |
| ATOM | 1342 | OD1 | ASP B 161 | 17.792 | 37.789 | -14.179 | 1.00 | 40.96 |
| ATOM | 1343 | OD2 | ASP B 161 | 15.875 | 38.349 | -15.158 | 1.00 | 46.07 |
| ATOM | 1344 | C | ASP B 161 | 14.469 | 34.505 | -15.229 | 1.00 | 34.72 |
| ATOM | 1345 | O | ASP B 161 | 15.172 | 33.519 | -15.400 | 1.00 | 34.32 |
| ATOM | 1346 | N | VAL B 162 | 13.207 | 34.588 | -15.644 | 1.00 | 37.81 |
| ATOM | 1348 | CA | VAL B 162 | 12.572 | 33.501 | -16.385 | 1.00 | 38.49 |
| ATOM | 1349 | CB | VAL B 162 | 11.105 | 33.220 | -15.886 | 1.00 | 34.01 |
| ATOM | 1350 | CG1 | VAL B 162 | 10.147 | 34.306 | -16.321 | 1.00 | 28.95 |
| ATOM | 1351 | CG2 | VAL B 162 | 10.614 | 31.901 | -16.399 | 1.00 | 31.65 |
| ATOM | 1352 | C | VAL B 162 | 12.535 | 33.785 | -17.879 | 1.00 | 43.61 |
| ATOM | 1353 | O | VAL B 162 | 12.695 | 34.926 | -18.329 | 1.00 | 45.17 |
| ATOM | 1354 | N | ARG B 163 | 12.379 | 32.717 | -18.638 | 1.00 | 44.16 |
| ATOM | 1356 | CA | ARG B 163 | 12.260 | 32.787 | -20.069 | 1.00 | 41.79 |
| ATOM | 1357 | CB | ARG B 163 | 13.479 | 32.207 | -20.739 | 1.00 | 36.45 |
| ATOM | 1358 | CG | ARG B 163 | 14.266 | 33.228 | -21.518 | 1.00 | 47.07 |
| ATOM | 1359 | CD | ARG B 163 | 15.589 | 32.656 | -22.083 | 1.00 | 43.87 |
| ATOM | 1360 | NE | ARG B 163 | 15.390 | 31.574 | -23.054 | 1.00 | 41.71 |
| ATOM | 1362 | CZ | ARG B 163 | 15.201 | 30.297 | -22.730 | 1.00 | 37.15 |
| ATOM | 1363 | NH1 | ARG B 163 | 15.178 | 29.928 | -21.457 | 1.00 | 37.51 |
| ATOM | 1366 | NH2 | ARG B 163 | 15.063 | 29.383 | -23.680 | 1.00 | 41.43 |
| ATOM | 1369 | C | ARG B 163 | 11.130 | 31.835 | -20.264 | 1.00 | 43.94 |
| ATOM | 1370 | O | ARG B 163 | 10.718 | 31.137 | -19.333 | 1.00 | 45.85 |
| ATOM | 1371 | N | PHE B 164 | 10.626 | 31.772 | -21.475 | 1.00 | 42.66 |
| ATOM | 1373 | CA | PHE B 164 | 9.545 | 30.857 | -21.724 | 1.00 | 36.54 |
| ATOM | 1374 | CB | PHE B 164 | 8.251 | 31.634 | -21.936 | 1.00 | 38.77 |
| ATOM | 1375 | CG | PHE B 164 | 7.829 | 32.421 | -20.730 | 1.00 | 35.87 |
| ATOM | 1376 | CD1 | PHE B 164 | 8.062 | 33.788 | -20.663 | 1.00 | 34.40 |
| ATOM | 1377 | CD2 | PHE B 164 | 7.254 | 31.779 | -19.634 | 1.00 | 38.33 |
| ATOM | 1378 | CE1 | PHE B 164 | 7.736 | 34.506 | -19.519 | 1.00 | 40.74 |
| ATOM | 1379 | CE2 | PHE B 164 | 6.922 | 32.481 | -18.486 | 1.00 | 44.04 |

FIG. 1A-23

| ATOM | 1380 | CZ  | PHE | B | 164 | 7.165  | 33.850 | -18.425 | 1.00 | 45.18 |
| ATOM | 1381 | C   | PHE | B | 164 | 9.932  | 30.061 | -22.931 | 1.00 | 31.44 |
| ATOM | 1382 | O   | PHE | B | 164 | 10.714 | 30.531 | -23.750 | 1.00 | 29.43 |
| ATOM | 1383 | N   | GLU | B | 165 | 9.530  | 28.803 | -22.952 | 1.00 | 30.68 |
| ATOM | 1385 | CA  | GLU | B | 165 | 9.814  | 27.957 | -24.088 | 1.00 | 37.09 |
| ATOM | 1386 | CB  | GLU | B | 165 | 10.964 | 26.996 | -23.793 | 1.00 | 38.00 |
| ATOM | 1387 | CG  | GLU | B | 165 | 12.314 | 27.570 | -24.211 | 1.00 | 45.98 |
| ATOM | 1388 | CD  | GLU | B | 165 | 13.501 | 26.781 | -23.675 | 1.00 | 54.04 |
| ATOM | 1389 | OE1 | GLU | B | 165 | 14.484 | 26.591 | -24.436 | 1.00 | 58.89 |
| ATOM | 1390 | OE2 | GLU | B | 165 | 13.475 | 26.381 | -22.487 | 1.00 | 47.24 |
| ATOM | 1391 | C   | GLU | B | 165 | 8.531  | 27.244 | -24.479 | 1.00 | 40.35 |
| ATOM | 1392 | O   | GLU | B | 165 | 7.830  | 26.707 | -23.619 | 1.00 | 47.17 |
| ATOM | 1393 | N   | SER | B | 166 | 8.169  | 27.373 | -25.759 | 1.00 | 39.33 |
| ATOM | 1395 | CA  | SER | B | 166 | 6.956  | 26.779 | -26.309 | 1.00 | 34.75 |
| ATOM | 1396 | CB  | SER | B | 166 | 6.498  | 27.538 | -27.563 | 1.00 | 38.72 |
| ATOM | 1397 | OG  | SER | B | 166 | 6.014  | 28.840 | -27.263 | 1.00 | 49.12 |
| ATOM | 1399 | C   | SER | B | 166 | 7.094  | 25.312 | -26.655 | 1.00 | 31.24 |
| ATOM | 1400 | O   | SER | B | 166 | 8.188  | 24.750 | -26.735 | 1.00 | 26.32 |
| ATOM | 1401 | N   | ILE | B | 167 | 5.956  | 24.719 | -26.939 | 1.00 | 29.79 |
| ATOM | 1403 | CA  | ILE | B | 167 | 5.919  | 23.332 | -27.290 | 1.00 | 32.42 |
| ATOM | 1404 | CB  | ILE | B | 167 | 6.044  | 22.492 | -26.024 | 1.00 | 21.29 |
| ATOM | 1405 | CG2 | ILE | B | 167 | 4.917  | 22.810 | -25.092 | 1.00 | 23.13 |
| ATOM | 1406 | CG1 | ILE | B | 167 | 6.080  | 21.013 | -26.360 | 1.00 | 19.45 |
| ATOM | 1407 | CD1 | ILE | B | 167 | 5.858  | 20.145 | -25.166 | 1.00 | 22.65 |
| ATOM | 1408 | C   | ILE | B | 167 | 4.570  | 23.147 | -27.968 | 1.00 | 34.87 |
| ATOM | 1409 | O   | ILE | B | 167 | 3.591  | 23.808 | -27.613 | 1.00 | 39.54 |
| ATOM | 1410 | N   | ARG | B | 168 | 4.546  | 22.326 | -29.005 | 1.00 | 29.12 |
| ATOM | 1412 | CA  | ARG | B | 168 | 3.318  | 22.089 | -29.731 | 1.00 | 26.85 |
| ATOM | 1413 | CB  | ARG | B | 168 | 3.615  | 22.030 | -31.217 | 1.00 | 38.31 |
| ATOM | 1414 | CG  | ARG | B | 168 | 2.442  | 22.407 | -32.084 | 1.00 | 41.70 |
| ATOM | 1415 | CD  | ARG | B | 168 | 2.184  | 21.363 | -33.154 | 1.00 | 45.62 |
| ATOM | 1416 | NE  | ARG | B | 168 | 1.669  | 21.985 | -34.371 | 1.00 | 54.88 |
| ATOM | 1418 | CZ  | ARG | B | 168 | 0.790  | 21.420 | -35.194 | 1.00 | 58.34 |
| ATOM | 1419 | NH1 | ARG | B | 168 | 0.307  | 20.204 | -34.928 | 1.00 | 57.86 |
| ATOM | 1422 | NH2 | ARG | B | 168 | 0.422  | 22.065 | -36.304 | 1.00 | 65.90 |
| ATOM | 1425 | C   | ARG | B | 168 | 2.732  | 20.777 | -29.275 | 1.00 | 22.19 |
| ATOM | 1426 | O   | ARG | B | 168 | 3.332  | 19.725 | -29.450 | 1.00 | 26.95 |
| ATOM | 1427 | N   | LEU | B | 169 | 1.551  | 20.841 | -28.697 | 1.00 | 18.94 |
| ATOM | 1429 | CA  | LEU | B | 169 | 0.899  | 19.669 | -28.194 | 1.00 | 16.56 |
| ATOM | 1430 | CB  | LEU | B | 169 | -0.279 | 20.086 | -27.331 | 1.00 | 12.93 |
| ATOM | 1431 | CG  | LEU | B | 169 | 0.110  | 20.667 | -25.977 | 1.00 | 14.54 |
| ATOM | 1432 | CD1 | LEU | B | 169 | -1.103 | 21.148 | -25.261 | 1.00 | 10.37 |
| ATOM | 1433 | CD2 | LEU | B | 169 | 0.785  | 19.614 | -25.153 | 1.00 | 14.48 |
| ATOM | 1434 | C   | LEU | B | 169 | 0.449  | 18.756 | -29.310 | 1.00 | 22.34 |
| ATOM | 1435 | O   | LEU | B | 169 | -0.002 | 19.205 | -30.357 | 1.00 | 25.19 |
| ATOM | 1436 | N   | PRO | B | 170 | 0.565  | 17.443 | -29.097 | 1.00 | 24.27 |
| ATOM | 1437 | CD  | PRO | B | 170 | 1.235  | 16.825 | -27.939 | 1.00 | 22.49 |
| ATOM | 1438 | CA  | PRO | B | 170 | 0.178  | 16.418 | -30.066 | 1.00 | 23.01 |
| ATOM | 1439 | CB  | PRO | B | 170 | 1.128  | 15.278 | -29.720 | 1.00 | 16.55 |

FIG. 1A-24

| ATOM | 1440 | CG | PRO | B | 170 | 1.130 | 15.322 | -28.249 | 1.00 | 19.51 |
| --- | --- | --- | --- | --- | --- | --- | --- | --- | --- | --- |
| ATOM | 1441 | C | PRO | B | 170 | -1.272 | 15.952 | -29.926 | 1.00 | 25.26 |
| ATOM | 1442 | O | PRO | B | 170 | -1.760 | 15.688 | -28.823 | 1.00 | 29.89 |
| ATOM | 1443 | N | GLY | B | 171 | -1.962 | 15.850 | -31.050 | 1.00 | 31.43 |
| ATOM | 1445 | CA | GLY | B | 171 | -3.327 | 15.355 | -31.015 | 1.00 | 34.61 |
| ATOM | 1446 | C | GLY | B | 171 | -4.433 | 16.378 | -30.934 | 1.00 | 34.44 |
| ATOM | 1447 | O | GLY | B | 171 | -5.598 | 16.065 | -31.195 | 1.00 | 35.10 |
| ATOM | 1448 | N | CYS | B | 172 | -4.096 | 17.592 | -30.544 | 1.00 | 32.82 |
| ATOM | 1450 | CA | CYS | B | 172 | -5.112 | 18.609 | -30.453 | 1.00 | 32.03 |
| ATOM | 1451 | C | CYS | B | 172 | -5.904 | 18.677 | -31.752 | 1.00 | 32.57 |
| ATOM | 1452 | O | CYS | B | 172 | -5.329 | 18.591 | -32.851 | 1.00 | 33.55 |
| ATOM | 1453 | CB | CYS | B | 172 | -4.478 | 19.951 | -30.166 | 1.00 | 26.15 |
| ATOM | 1454 | SG | CYS | B | 172 | -3.349 | 19.856 | -28.762 | 1.00 | 35.29 |
| ATOM | 1455 | N | PRO | B | 173 | -7.245 | 18.760 | -31.632 | 1.00 | 27.71 |
| ATOM | 1456 | CD | PRO | B | 173 | -7.947 | 18.744 | -30.338 | 1.00 | 30.58 |
| ATOM | 1457 | CA | PRO | B | 173 | -8.207 | 18.840 | -32.721 | 1.00 | 23.81 |
| ATOM | 1458 | CB | PRO | B | 173 | -9.518 | 19.030 | -31.983 | 1.00 | 30.85 |
| ATOM | 1459 | CG | PRO | B | 173 | -9.301 | 18.275 | -30.726 | 1.00 | 34.94 |
| ATOM | 1460 | C | PRO | B | 173 | -7.901 | 20.037 | -33.597 | 1.00 | 26.25 |
| ATOM | 1461 | O | PRO | B | 173 | -7.000 | 20.824 | -33.315 | 1.00 | 24.40 |
| ATOM | 1462 | N | ARG | B | 174 | -8.672 | 20.205 | -34.655 | 1.00 | 28.71 |
| ATOM | 1464 | CA | ARG | B | 174 | -8.409 | 21.315 | -35.536 | 1.00 | 37.26 |
| ATOM | 1465 | CB | ARG | B | 174 | -8.971 | 21.012 | -36.939 | 1.00 | 49.13 |
| ATOM | 1466 | CG | ARG | B | 174 | -8.070 | 20.043 | -37.771 | 1.00 | 51.77 |
| ATOM | 1467 | CD | ARG | B | 174 | -8.399 | 20.011 | -39.294 | 1.00 | 59.03 |
| ATOM | 1468 | NE | ARG | B | 174 | -7.256 | 19.620 | -40.148 | 1.00 | 62.16 |
| ATOM | 1470 | CZ | ARG | B | 174 | -6.915 | 18.362 | -40.485 | 1.00 | 64.83 |
| ATOM | 1471 | NH1 | ARG | B | 174 | -7.621 | 17.309 | -40.059 | 1.00 | 62.99 |
| ATOM | 1474 | NH2 | ARG | B | 174 | -5.831 | 18.152 | -41.233 | 1.00 | 60.99 |
| ATOM | 1477 | C | ARG | B | 174 | -8.905 | 22.647 | -34.954 | 1.00 | 37.03 |
| ATOM | 1478 | O | ARG | B | 174 | -9.974 | 22.708 | -34.367 | 1.00 | 40.90 |
| ATOM | 1479 | N | GLY | B | 175 | -8.065 | 23.676 | -35.036 | 1.00 | 39.08 |
| ATOM | 1481 | CA | GLY | B | 175 | -8.409 | 25.003 | -34.543 | 1.00 | 34.11 |
| ATOM | 1482 | C | GLY | B | 175 | -8.493 | 25.068 | -33.043 | 1.00 | 32.89 |
| ATOM | 1483 | O | GLY | B | 175 | -9.497 | 25.485 | -32.499 | 1.00 | 37.04 |
| ATOM | 1484 | N | VAL | B | 176 | -7.427 | 24.668 | -32.369 | 1.00 | 32.05 |
| ATOM | 1486 | CA | VAL | B | 176 | -7.399 | 24.670 | -30.906 | 1.00 | 31.34 |
| ATOM | 1487 | CB | VAL | B | 176 | -7.206 | 23.224 | -30.354 | 1.00 | 18.83 |
| ATOM | 1488 | CG1 | VAL | B | 176 | -6.773 | 23.249 | -28.895 | 1.00 | 13.94 |
| ATOM | 1489 | CG2 | VAL | B | 176 | -8.478 | 22.419 | -30.510 | 1.00 | 21.98 |
| ATOM | 1490 | C | VAL | B | 176 | -6.249 | 25.524 | -30.367 | 1.00 | 38.05 |
| ATOM | 1491 | O | VAL | B | 176 | -6.404 | 26.312 | -29.411 | 1.00 | 40.83 |
| ATOM | 1492 | N | ASN | B | 177 | -5.105 | 25.347 | -31.015 | 1.00 | 38.01 |
| ATOM | 1494 | CA | ASN | B | 177 | -3.856 | 25.993 | -30.673 | 1.00 | 32.69 |
| ATOM | 1495 | CB | ASN | B | 177 | -4.009 | 27.403 | -30.148 | 1.00 | 19.96 |
| ATOM | 1496 | CG | ASN | B | 177 | -2.711 | 28.147 | -30.207 | 1.00 | 23.51 |
| ATOM | 1497 | OD1 | ASN | B | 177 | -1.641 | 27.526 | -30.310 | 1.00 | 21.41 |
| ATOM | 1498 | ND2 | ASN | B | 177 | -2.778 | 29.474 | -30.217 | 1.00 | 24.32 |
| ATOM | 1501 | C | ASN | B | 177 | -3.206 | 25.145 | -29.628 | 1.00 | 31.12 |

FIG. 1A-25

```
ATOM   1502  O    ASN B 177      -3.608  25.127 -28.481  1.00 40.11
ATOM   1503  N    PRO B 178      -2.227  24.364 -30.045  1.00 29.84
ATOM   1504  CD   PRO B 178      -1.906  24.127 -31.462  1.00 23.27
ATOM   1505  CA   PRO B 178      -1.487  23.468 -29.175  1.00 30.67
ATOM   1506  CB   PRO B 178      -1.363  22.243 -30.048  1.00 32.88
ATOM   1507  CG   PRO B 178      -1.097  22.865 -31.417  1.00 26.67
ATOM   1508  C    PRO B 178      -0.130  24.034 -28.797  1.00 32.51
ATOM   1509  O    PRO B 178       0.777  23.309 -28.411  1.00 32.54
ATOM   1510  N    THR B 179       0.041  25.327 -28.969  1.00 32.17
ATOM   1512  CA   THR B 179       1.307  25.908 -28.606  1.00 33.12
ATOM   1513  CB   THR B 179       1.672  27.079 -29.483  1.00 32.23
ATOM   1514  OG1  THR B 179       1.661  26.659 -30.849  1.00 39.76
ATOM   1516  CG2  THR B 179       3.063  27.595 -29.108  1.00 39.34
ATOM   1517  C    THR B 179       1.154  26.408 -27.204  1.00 34.20
ATOM   1518  O    THR B 179       0.422  27.356 -26.949  1.00 39.35
ATOM   1519  N    THR B 180       1.840  25.768 -26.283  1.00 27.84
ATOM   1521  CA   THR B 180       1.745  26.179 -24.911  1.00 20.69
ATOM   1522  CB   THR B 180       1.033  25.134 -24.132  1.00 20.71
ATOM   1523  OG1  THR B 180       1.628  23.869 -24.423  1.00 18.43
ATOM   1525  CG2  THR B 180      -0.403  25.099 -24.562  1.00 13.10
ATOM   1526  C    THR B 180       3.123  26.404 -24.376  1.00 22.25
ATOM   1527  O    THR B 180       3.969  25.525 -24.400  1.00 14.49
ATOM   1528  N    SER B 181       3.349  27.635 -23.971  1.00 25.38
ATOM   1530  CA   SER B 181       4.618  28.068 -23.448  1.00 27.56
ATOM   1531  CB   SER B 181       4.665  29.575 -23.555  1.00 22.33
ATOM   1532  OG   SER B 181       3.349  30.077 -23.368  1.00 22.82
ATOM   1534  C    SER B 181       4.786  27.647 -22.006  1.00 32.19
ATOM   1535  O    SER B 181       3.802  27.546 -21.249  1.00 34.04
ATOM   1536  N    TYR B 182       6.040  27.409 -21.629  1.00 28.04
ATOM   1538  CA   TYR B 182       6.353  27.008 -20.279  1.00 28.64
ATOM   1539  CB   TYR B 182       6.551  25.490 -20.202  1.00 28.97
ATOM   1540  CG   TYR B 182       7.642  24.936 -21.046  1.00 15.09
ATOM   1541  CD1  TYR B 182       7.367  24.333 -22.248  1.00 17.88
ATOM   1542  CE1  TYR B 182       8.384  23.864 -23.048  1.00 25.41
ATOM   1543  CD2  TYR B 182       8.952  25.045 -20.654  1.00 21.82
ATOM   1544  CE2  TYR B 182       9.971  24.580 -21.441  1.00 30.15
ATOM   1545  CZ   TYR B 182       9.691  23.999 -22.639  1.00 23.65
ATOM   1546  OH   TYR B 182      10.730  23.622 -23.450  1.00 22.92
ATOM   1548  C    TYR B 182       7.543  27.780 -19.733  1.00 32.15
ATOM   1549  O    TYR B 182       8.540  27.973 -20.432  1.00 40.12
ATOM   1550  N    ALA B 183       7.409  28.255 -18.496  1.00 32.75
ATOM   1552  CA   ALA B 183       8.444  29.041 -17.832  1.00 29.65
ATOM   1553  CB   ALA B 183       7.857  29.740 -16.619  1.00 25.82
ATOM   1554  C    ALA B 183       9.718  28.295 -17.434  1.00 29.60
ATOM   1555  O    ALA B 183       9.710  27.439 -16.547  1.00 33.60
ATOM   1556  N    VAL B 184      10.812  28.635 -18.098  1.00 24.54
ATOM   1558  CA   VAL B 184      12.106  28.049 -17.791  1.00 25.29
ATOM   1559  CB   VAL B 184      12.830  27.582 -19.074  1.00 22.53
ATOM   1560  CG1  VAL B 184      12.206  28.221 -20.281  1.00 19.02
```

FIG. 1A-26

| ATOM | 1561 | CG2 | VAL | B | 184 | 14.326 | 27.867 | -19.002 | 1.00 | 16.40 |
| ATOM | 1562 | C | VAL | B | 184 | 12.895 | 29.118 | -17.015 | 1.00 | 27.63 |
| ATOM | 1563 | O | VAL | B | 184 | 12.953 | 30.275 | -17.441 | 1.00 | 30.60 |
| ATOM | 1564 | N | ALA | B | 185 | 13.447 | 28.734 | -15.859 | 1.00 | 28.65 |
| ATOM | 1566 | CA | ALA | B | 185 | 14.190 | 29.631 | -14.965 | 1.00 | 25.14 |
| ATOM | 1567 | CB | ALA | B | 185 | 14.016 | 29.189 | -13.550 | 1.00 | 17.94 |
| ATOM | 1568 | C | ALA | B | 185 | 15.664 | 29.769 | -15.233 | 1.00 | 27.32 |
| ATOM | 1569 | O | ALA | B | 185 | 16.391 | 28.781 | -15.209 | 1.00 | 27.39 |
| ATOM | 1570 | N | LEU | B | 186 | 16.109 | 31.011 | -15.408 | 1.00 | 29.32 |
| ATOM | 1572 | CA | LEU | B | 186 | 17.520 | 31.331 | -15.657 | 1.00 | 26.71 |
| ATOM | 1573 | CB | LEU | B | 186 | 17.656 | 32.510 | -16.628 | 1.00 | 23.45 |
| ATOM | 1574 | CG | LEU | B | 186 | 16.853 | 32.430 | -17.925 | 1.00 | 22.68 |
| ATOM | 1575 | CD1 | LEU | B | 186 | 16.949 | 33.742 | -18.688 | 1.00 | 32.16 |
| ATOM | 1576 | CD2 | LEU | B | 186 | 17.352 | 31.274 | -18.757 | 1.00 | 29.35 |
| ATOM | 1577 | C | LEU | B | 186 | 18.190 | 31.667 | -14.326 | 1.00 | 25.56 |
| ATOM | 1578 | O | LEU | B | 186 | 19.228 | 31.113 | -13.981 | 1.00 | 21.55 |
| ATOM | 1579 | N | SER | B | 187 | 17.629 | 32.611 | -13.594 | 1.00 | 24.65 |
| ATOM | 1581 | CA | SER | B | 187 | 18.206 | 32.914 | -12.312 | 1.00 | 28.09 |
| ATOM | 1582 | CB | SER | B | 187 | 18.942 | 34.251 | -12.312 | 1.00 | 30.51 |
| ATOM | 1583 | OG | SER | B | 187 | 18.104 | 35.305 | -12.719 | 1.00 | 37.47 |
| ATOM | 1585 | C | SER | B | 187 | 17.124 | 32.858 | -11.264 | 1.00 | 30.09 |
| ATOM | 1586 | O | SER | B | 187 | 15.975 | 33.224 | -11.511 | 1.00 | 28.81 |
| ATOM | 1587 | N | CYS | B | 188 | 17.476 | 32.223 | -10.158 | 1.00 | 29.89 |
| ATOM | 1589 | CA | CYS | B | 188 | 16.611 | 32.073 | -9.009 | 1.00 | 27.30 |
| ATOM | 1590 | C | CYS | B | 188 | 17.169 | 33.050 | -7.965 | 1.00 | 31.99 |
| ATOM | 1591 | O | CYS | B | 188 | 18.372 | 33.355 | -7.974 | 1.00 | 37.93 |
| ATOM | 1592 | CB | CYS | B | 188 | 16.690 | 30.649 | -8.468 | 1.00 | 28.78 |
| ATOM | 1593 | SG | CYS | B | 188 | 16.019 | 29.351 | -9.543 | 1.00 | 32.17 |
| ATOM | 1594 | N | GLN | B | 189 | 16.311 | 33.507 | -7.056 | 1.00 | 29.96 |
| ATOM | 1596 | CA | GLN | B | 189 | 16.687 | 34.466 | -6.032 | 1.00 | 24.25 |
| ATOM | 1597 | CB | GLN | B | 189 | 16.193 | 35.853 | -6.449 | 1.00 | 34.03 |
| ATOM | 1598 | CG | GLN | B | 189 | 16.592 | 37.010 | -5.543 | 1.00 | 45.49 |
| ATOM | 1599 | CD | GLN | B | 189 | 15.690 | 38.224 | -5.733 | 1.00 | 48.18 |
| ATOM | 1600 | OE1 | GLN | B | 189 | 14.650 | 38.144 | -6.399 | 1.00 | 44.04 |
| ATOM | 1601 | NE2 | GLN | B | 189 | 16.074 | 39.350 | -5.130 | 1.00 | 48.14 |
| ATOM | 1604 | C | GLN | B | 189 | 15.994 | 34.071 | -4.756 | 1.0C | 19.05 |
| ATOM | 1605 | O | GLN | B | 189 | 14.996 | 33.362 | -4.767 | 1.00 | 22.44 |
| ATOM | 1606 | N | CYS | B | 190 | 16.501 | 34.584 | -3.655 | 1.00 | 16.88 |
| ATOM | 1608 | CA | CYS | B | 190 | 15.936 | 34.303 | -2.356 | 1.00 | 17.53 |
| ATOM | 1609 | C | CYS | B | 190 | 15.331 | 35.606 | -1.800 | 1.00 | 14.70 |
| ATOM | 1610 | O | CYS | B | 190 | 16.025 | 36.429 | -1.219 | 1.00 | 14.66 |
| ATOM | 1611 | CB | CYS | B | 190 | 17.056 | 33.767 | -1.480 | 1.00 | 16.56 |
| ATOM | 1612 | SG | CYS | B | 190 | 16.497 | 33.080 | 0.088 | 1.00 | 19.12 |
| ATOM | 1613 | N | ALA | B | 191 | 14.049 | 35.818 | -2.062 | 1.00 | 13.55 |
| ATOM | 1615 | CA | ALA | B | 191 | 13.343 | 37.018 | -1.636 | 1.00 | 15.58 |
| ATOM | 1616 | CB | ALA | B | 191 | 13.158 | 37.943 | -2.794 | 1.00 | 23.60 |
| ATOM | 1617 | C | ALA | B | 191 | 12.002 | 36.583 | -1.116 | 1.00 | 16.43 |
| ATOM | 1618 | O | ALA | B | 191 | 11.756 | 35.391 | -0.984 | 1.00 | 15.88 |
| ATOM | 1619 | N | LEU | B | 192 | 11.121 | 37.525 | -0.822 | 1.00 | 14 64 |

FIG. 1A-27

| ATOM | 1621 | CA | LEU B 192 | 9.825 | 37.133 | -0.296 | 1.00 | 17.60 |
| --- | --- | --- | --- | --- | --- | --- | --- | --- |
| ATOM | 1622 | CB | LEU B 192 | 9.220 | 38.237 | 0.550 | 1.00 | 21.59 |
| ATOM | 1623 | CG | LEU B 192 | 9.454 | 39.670 | 0.096 | 1.00 | 28.40 |
| ATOM | 1624 | CD1 | LEU B 192 | 8.687 | 39.969 | -1.197 | 1.00 | 31.24 |
| ATOM | 1625 | CD2 | LEU B 192 | 8.998 | 40.577 | 1.220 | 1.00 | 32.37 |
| ATOM | 1626 | C | LEU B 192 | 8.805 | 36.595 | -1.283 | 1.00 | 20.36 |
| ATOM | 1627 | O | LEU B 192 | 8.910 | 36.741 | -2.499 | 1.00 | 26.17 |
| ATOM | 1628 | N | CYS B 193 | 7.794 | 35.960 | -0.738 | 1.00 | 22.72 |
| ATOM | 1630 | CA | CYS B 193 | 6.763 | 35.370 | -1.552 | 1.00 | 22.36 |
| ATOM | 1631 | C | CYS B 193 | 5.642 | 36.382 | -1.682 | 1.00 | 27.10 |
| ATOM | 1632 | O | CYS B 193 | 4.881 | 36.555 | -0.737 | 1.00 | 29.62 |
| ATOM | 1633 | CB | CYS B 193 | 6.268 | 34.128 | -0.830 | 1.00 | 13.41 |
| ATOM | 1634 | SG | CYS B 193 | 5.482 | 32.912 | -1.891 | 1.00 | 17.20 |
| ATOM | 1635 | N | ARG B 194 | 5.567 | 37.095 | -2.809 | 1.00 | 34.16 |
| ATOM | 1637 | CA | ARG B 194 | 4.504 | 38.093 | -3.002 | 1.00 | 35.48 |
| ATOM | 1638 | CB | ARG B 194 | 4.905 | 39.137 | -4.047 | 1.00 | 35.45 |
| ATOM | 1639 | CG | ARG B 194 | 5.458 | 40.449 | -3.453 | 1.00 | 43.44 |
| ATOM | 1640 | CD | ARG B 194 | 4.526 | 41.084 | -2.385 | 1.00 | 47.86 |
| ATOM | 1641 | NE | ARG B 194 | 3.136 | 41.276 | -2.832 | 1.00 | 53.59 |
| ATOM | 1643 | CZ | ARG B 194 | 2.097 | 41.499 | -2.021 | 1.00 | 49.96 |
| ATOM | 1644 | NH1 | ARG B 194 | 2.268 | 41.571 | -0.709 | 1.00 | 48.35 |
| ATOM | 1647 | NH2 | ARG B 194 | 0.874 | 41.615 | -2.519 | 1.00 | 49.83 |
| ATOM | 1650 | C | ARG B 194 | 3.148 | 37.467 | -3.348 | 1.00 | 35.66 |
| ATOM | 1651 | O | ARG B 194 | 2.954 | 36.967 | -4.456 | 1.00 | 35.06 |
| ATOM | 1652 | N | ARG B 195 | 2.212 | 37.544 | -2.399 | 1.00 | 36.15 |
| ATOM | 1654 | CA | ARG B 195 | 0.865 | 36.970 | -2.523 | 1.00 | 37.91 |
| ATOM | 1655 | CB | ARG B 195 | 0.003 | 37.391 | -1.337 | 1.00 | 37.30 |
| ATOM | 1656 | CG | ARG B 195 | 0.480 | 36.868 | -0.012 | 1.00 | 44.94 |
| ATOM | 1657 | CD | ARG B 195 | 0.753 | 35.370 | -0.085 | 1.00 | 57.41 |
| ATOM | 1658 | NE | ARG B 195 | -0.422 | 34.554 | -0.428 | 1.00 | 60.57 |
| ATOM | 1660 | CZ | ARG B 195 | -1.145 | 33.864 | 0.459 | 1.00 | 59.16 |
| ATOM | 1661 | NH1 | ARG B 195 | -0.826 | 33.890 | 1.761 | 1.00 | 61.28 |
| ATOM | 1664 | NH2 | ARG B 195 | -2.157 | 33.105 | 0.038 | 1.00 | 52.23 |
| ATOM | 1667 | C | ARG B 195 | 0.097 | 37.307 | -3.784 | 1.00 | 39.60 |
| ATOM | 1668 | O | ARG B 195 | -0.689 | 36.506 | -4.276 | 1.00 | 37.20 |
| ATOM | 1669 | N | SER B 196 | 0.297 | 38.522 | -4.270 | 1.00 | 38.67 |
| ATOM | 1671 | CA | SER B 196 | -0.380 | 39.031 | -5.451 | 1.00 | 36.35 |
| ATOM | 1672 | CB | SER B 196 | -0.011 | 40.498 | -5.617 | 1.00 | 42.47 |
| ATOM | 1673 | OG | SER B 196 | 1.372 | 40.692 | -5.343 | 1.00 | 47.27 |
| ATOM | 1675 | C | SER B 196 | -0.144 | 38.298 | -6.763 | 1.00 | 37.69 |
| ATOM | 1676 | O | SER B 196 | -0.830 | 38.550 | -7.745 | 1.00 | 41.10 |
| ATOM | 1677 | N | THR B 197 | 0.878 | 37.462 | -6.820 | 1.00 | 39.99 |
| ATOM | 1679 | CA | THR B 197 | 1.157 | 36.733 | -8.045 | 1.00 | 40.50 |
| ATOM | 1680 | CB | THR B 197 | 2.342 | 37.371 | -8.860 | 1.00 | 47.37 |
| ATOM | 1681 | OG1 | THR B 197 | 3.613 | 36.920 | -8.360 | 1.00 | 52.70 |
| ATOM | 1683 | CG2 | THR B 197 | 2.301 | 38.895 | -8.773 | 1.00 | 47.75 |
| ATOM | 1684 | C | THR B 197 | 1.463 | 35.277 | -7.718 | 1.00 | 36.65 |
| ATOM | 1685 | O | THR B 197 | 1.060 | 34.376 | -8.448 | 1.00 | 40.36 |
| ATOM | 1686 | N | THR B 198 | 2.106 | 35.052 | -6.575 | 1.00 | 29.87 |

FIG. 1A-28

| | | | | | | | | | |
|---|---|---|---|---|---|---|---|---|---|
| ATOM | 1688 | CA | THR | B | 198 | 2.492 | 33.721 | -6.144 | 1.00 21.97 |
| ATOM | 1689 | CB | THR | B | 198 | 3.897 | 33.763 | -5.547 | 1.00 25.87 |
| ATOM | 1690 | OG1 | THR | B | 198 | 4.655 | 34.797 | -6.196 | 1.00 27.89 |
| ATOM | 1692 | CG2 | THR | B | 198 | 4.601 | 32.418 | -5.729 | 1.00 28.71 |
| ATOM | 1693 | C | THR | B | 198 | 1.550 | 33.103 | -5.113 | 1.00 22.76 |
| ATOM | 1694 | O | THR | B | 198 | 1.073 | 33.777 | -4.183 | 1.00 25.98 |
| ATOM | 1695 | N | ASP | B | 199 | 1.254 | 31.823 | -5.304 | 1.00 18.91 |
| ATOM | 1697 | CA | ASP | B | 199 | 0.419 | 31.112 | -4.374 | 1.00 12.99 |
| ATOM | 1698 | CB | ASP | B | 199 | -0.182 | 29.916 | -5.043 | 1.00 18.29 |
| ATOM | 1699 | CG | ASP | B | 199 | -0.908 | 29.040 | -4.075 | 1.00 22.42 |
| ATOM | 1700 | OD1 | ASP | B | 199 | -0.727 | 27.800 | -4.133 | 1.00 15.98 |
| ATOM | 1701 | OD2 | ASP | B | 199 | -1.658 | 29.609 | -3.250 | 1.00 26.70 |
| ATOM | 1702 | C | ASP | B | 199 | 1.385 | 30.629 | -3.324 | 1.00 16.14 |
| ATOM | 1703 | O | ASP | B | 199 | 1.974 | 29.570 | -3.458 | 1.00 11.29 |
| ATOM | 1704 | N | CYS | B | 200 | 1.571 | 31.426 | -2.290 | 1.00 19.06 |
| ATOM | 1706 | CA | CYS | B | 200 | 2.506 | 31.107 | -1.229 | 1.00 17.34 |
| ATOM | 1707 | C | CYS | B | 200 | 2.008 | 30.121 | -0.200 | 1.00 19.43 |
| ATOM | 1708 | O | CYS | B | 200 | 1.402 | 30.499 | 0.803 | 1.00 20.41 |
| ATOM | 1709 | CB | CYS | B | 200 | 2.906 | 32.392 | -0.569 | 1.00 13.99 |
| ATOM | 1710 | SG | CYS | B | 200 | 3.578 | 33.505 | -1.821 | 1.00 13.97 |
| ATOM | 1711 | N | GLY | B | 201 | 2.334 | 28.855 | -0.415 | 1.00 20.77 |
| ATOM | 1713 | CA | GLY | B | 201 | 1.875 | 27.827 | 0.487 | 1.00 15.85 |
| ATOM | 1714 | C | GLY | B | 201 | 2.992 | 26.952 | 0.975 | 1.00 18.69 |
| ATOM | 1715 | O | GLY | B | 201 | 4.166 | 27.301 | 0.875 | 1.00 23.85 |
| ATOM | 1716 | N | GLY | B | 202 | 2.601 | 25.806 | 1.511 | 1.00 18.09 |
| ATOM | 1718 | CA | GLY | B | 202 | 3.538 | 24.859 | 2.059 | 1.00 11.78 |
| ATOM | 1719 | C | GLY | B | 202 | 3.756 | 23.768 | 1.061 | 1.00 11.32 |
| ATOM | 1720 | O | GLY | B | 202 | 3.282 | 23.873 | -0.058 | 1.00 23.31 |
| ATOM | 1721 | N | PRO | B | 203 | 4.441 | 22.694 | 1.456 | 1.00 8.30 |
| ATOM | 1722 | CD | PRO | B | 203 | 5.000 | 22.668 | 2.806 | 1.00 8.58 |
| ATOM | 1723 | CA | PRO | B | 203 | 4.832 | 21.481 | 0.744 | 1.00 8.13 |
| ATOM | 1724 | CB | PRO | B | 203 | 5.765 | 20.797 | 1.726 | 1.00 12.24 |
| ATOM | 1725 | CG | PRO | B | 203 | 6.238 | 21.895 | 2.587 | 1.00 12.71 |
| ATOM | 1726 | C | PRO | B | 203 | 3.745 | 20.517 | 0.355 | 1.00 18.94 |
| ATOM | 1727 | O | PRO | B | 203 | 3.053 | 19.950 | 1.215 | 1.00 22.55 |
| ATOM | 1728 | N | LYS | B | 204 | 3.675 | 20.272 | -0.951 | 1.00 27.78 |
| ATOM | 1730 | CA | LYS | B | 204 | 2.731 | 19.339 | -1.549 | 1.00 31.30 |
| ATOM | 1731 | CB | LYS | B | 204 | 1.948 | 20.006 | -2.673 | 1.00 30.50 |
| ATOM | 1732 | CG | LYS | B | 204 | 1.436 | 21.397 | -2.370 | 1.00 34.77 |
| ATOM | 1733 | CD | LYS | B | 204 | 0.617 | 21.897 | -3.532 | 1.00 43.60 |
| ATOM | 1734 | CE | LYS | B | 204 | 1.314 | 21.579 | -4.874 | 1.00 48.86 |
| ATOM | 1735 | NZ | LYS | B | 204 | 0.404 | 21.660 | -6.097 | 1.00 58.63 |
| ATOM | 1739 | C | LYS | B | 204 | 3.630 | 18.264 | -2.144 | 1.00 32.65 |
| ATOM | 1740 | O | LYS | B | 204 | 4.794 | 18.521 | -2.453 | 1.00 27.38 |
| ATOM | 1741 | N | ASP | B | 205 | 3.100 | 17.065 | -2.328 | 1.00 41.15 |
| ATOM | 1743 | CA | ASP | B | 205 | 3.913 | 15.989 | -2.881 | 1.00 47.54 |
| ATOM | 1744 | CB | ASP | B | 205 | 3.459 | 14.636 | -2.326 | 1.00 49.81 |
| ATOM | 1745 | CG | ASP | B | 205 | 4.293 | 14.186 | -1.128 | 1.00 54.27 |
| ATOM | 1746 | OD1 | ASP | B | 205 | 5.127 | 14.987 | -0.618 | 1.00 57.52 |

FIG. 1A-29

```
ATOM   1747  OD2 ASP B 205       4.128  13.015  -0.709  1.00 57.70
ATOM   1748  C   ASP B 205       4.104  15.938  -4.409  1.00 48.51
ATOM   1749  O   ASP B 205       3.261  15.410  -5.152  1.00 47.49
ATOM   1750  N   HIS B 206       5.232  16.502  -4.851  1.00 52.05
ATOM   1752  CA  HIS B 206       5.626  16.554  -6.264  1.00 54.56
ATOM   1753  CB  HIS B 206       6.574  15.396  -6.587  1.00 59.18
ATOM   1754  CG  HIS B 206       8.027  15.751  -6.445  1.00 58.82
ATOM   1755  CD2 HIS B 206       8.687  16.907  -6.696  1.00 55.12
ATOM   1756  ND1 HIS B 206       8.990  14.834  -6.076  1.00 57.78
ATOM   1758  CE1 HIS B 206      10.180  15.409  -6.116  1.00 58.39
ATOM   1759  NE2 HIS B 206      10.023  16.666  -6.491  1.00 56.04
ATOM   1761  C   HIS B 206       4.462  16.656  -7.262  1.00 51.68
ATOM   1762  O   HIS B 206       4.094  15.696  -7.939  1.00 54.39
ATOM   1763  N   PRO B 207       3.940  17.875  -7.419  1.00 49.95
ATOM   1764  CD  PRO B 207       4.538  19.058  -6.764  1.00 46.65
ATOM   1765  CA  PRO B 207       2.824  18.265  -8.282  1.00 48.87
ATOM   1766  CB  PRO B 207       2.482  19.645  -7.751  1.00 50.04
ATOM   1767  CG  PRO B 207       3.858  20.199  -7.458  1.00 49.38
ATOM   1768  C   PRO B 207       3.120  18.337  -9.764  1.00 47.44
ATOM   1769  O   PRO B 207       2.206  18.486 -10.573  1.00 50.88
ATOM   1770  N   LEU B 208       4.393  18.269 -10.117  1.00 41.76
ATOM   1772  CA  LEU B 208       4.783  18.363 -11.507  1.00 40.03
ATOM   1773  CB  LEU B 208       6.208  18.887 -11.621  1.00 38.46
ATOM   1774  CG  LEU B 208       7.246  18.608 -10.540  1.00 37.69
ATOM   1775  CD1 LEU B 208       7.266  19.814  -9.617  1.00 34.74
ATOM   1776  CD2 LEU B 208       6.998  17.261  -9.816  1.00 27.80
ATOM   1777  C   LEU B 208       4.563  17.143 -12.420  1.00 45.35
ATOM   1778  O   LEU B 208       4.938  17.161 -13.601  1.00 50.37
ATOM   1779  N   THR B 209       3.991  16.070 -11.891  1.00 45.67
ATOM   1781  CA  THR B 209       3.705  14.907 -12.731  1.00 44.04
ATOM   1782  CB  THR B 209       3.340  13.679 -11.886  1.00 40.15
ATOM   1783  OG1 THR B 209       2.803  12.660 -12.743  1.00 47.62
ATOM   1785  CG2 THR B 209       2.308  14.043 -10.799  1.00 39.80
ATOM   1786  C   THR B 209       2.472  15.289 -13.551  1.00 47.91
ATOM   1787  O   THR B 209       1.830  16.305 -13.251  1.00 44.79
ATOM   1788  N   CYS B 210       2.136  14.520 -14.588  1.00 49.62
ATOM   1790  CA  CYS B 210       0.935  14.860 -15.347  1.00 51.66
ATOM   1791  C   CYS B 210      -0.250  14.622 -14.405  1.00 55.61
ATOM   1792  O   CYS B 210      -0.782  13.503 -14.284  1.00 55.52
ATOM   1793  CB  CYS B 210       0.822  14.088 -16.674  1.00 49.10
ATOM   1794  SG  CYS B 210       1.658  14.874 -18.121  1.00 46.60
ATOM   1795  N   ASP B 211      -0.527  15.689 -13.644  1.00 61.20
ATOM   1797  CA  ASP B 211      -1.583  15.790 -12.621  1.00 65.23
ATOM   1798  CB  ASP B 211      -1.286  16.987 -11.683  1.00 65.41
ATOM   1799  CG  ASP B 211      -1.317  16.607 -10.198  1.00 63.92
ATOM   1800  OD1 ASP B 211      -2.130  17.201  -9.448  1.00 65.41
ATOM   1801  OD2 ASP B 211      -0.519  15.732  -9.783  1.00 62.32
ATOM   1802  C   ASP B 211      -2.976  15.955 -13.249  1.00 64.63
ATOM   1803  O   ASP B 211      -4.006  15.831 -12.557  1.00 62.03
```

FIG. 1A-30

| | | | | | | | | | |
|---|---|---|---|---|---|---|---|---|---|
| ATOM | 1804 | N | ASP | B | 212 | -2.980 | 16.288 | -14.542 | 1.00 62.54 |
| ATOM | 1806 | CA | ASP | B | 212 | -4.205 | 16.456 | -15.319 | 1.00 63.66 |
| ATOM | 1807 | CB | ASP | B | 212 | -4.879 | 15.087 | -15.519 | 1.00 66.58 |
| ATOM | 1808 | CG | ASP | B | 212 | -4.002 | 14.116 | -16.318 | 1.00 67.64 |
| ATOM | 1809 | OD1 | ASP | B | 212 | -3.257 | 13.319 | -15.687 | 1.00 68.37 |
| ATOM | 1810 | OD2 | ASP | B | 212 | -4.050 | 14.171 | -17.576 | 1.00 71.80 |
| ATOM | 1811 | C | ASP | B | 212 | -5.185 | 17.537 | -14.816 | 1.00 62.38 |
| ATOM | 1812 | O | ASP | B | 212 | -4.745 | 18.721 | -14.790 | 1.00 62.92 |
| ATOM | 1813 | OT | ASP | B | 212 | -6.358 | 17.211 | -14.485 | 1.00 52.84 |
| ATOM | 1814 | C1 | NAG | C | 301 | 16.923 | 30.271 | 27.867 | 1.00 33.78 |
| ATOM | 1816 | C2 | NAG | C | 301 | 17.430 | 30.444 | 29.270 | 1.00 40.30 |
| ATOM | 1818 | N2 | NAG | C | 301 | 17.536 | 31.848 | 29.608 | 1.00 40.33 |
| ATOM | 1820 | C7 | NAG | C | 301 | 16.554 | 32.428 | 30.292 | 1.00 44.87 |
| ATOM | 1821 | O7 | NAG | C | 301 | 15.534 | 31.811 | 30.639 | 1.00 51.00 |
| ATOM | 1822 | C8 | NAG | C | 301 | 16.722 | 33.909 | 30.612 | 1.00 45.52 |
| ATOM | 1826 | C3 | NAG | C | 301 | 18.785 | 29.744 | 29.366 | 1.00 43.88 |
| ATOM | 1828 | O3 | NAG | C | 301 | 19.206 | 29.751 | 30.728 | 1.00 43.91 |
| ATOM | 1830 | C4 | NAG | C | 301 | 18.724 | 28.278 | 28.826 | 1.00 42.54 |
| ATOM | 1832 | O4 | NAG | C | 301 | 20.046 | 27.846 | 28.418 | 1.00 42.93 |
| ATOM | 1833 | C5 | NAG | C | 301 | 17.818 | 28.111 | 27.593 | 1.00 43.86 |
| ATOM | 1835 | O5 | NAG | C | 301 | 16.620 | 28.898 | 27.689 | 1.00 42.70 |
| ATOM | 1836 | C6 | NAG | C | 301 | 17.394 | 26.677 | 27.390 | 1.00 47.22 |
| ATOM | 1839 | O6 | NAG | C | 301 | 18.497 | 25.883 | 26.973 | 1.00 56.54 |
| ATOM | 1841 | C1 | NAG | C | 302 | 20.872 | 27.221 | 29.338 | 1.00 51.88 |
| ATOM | 1843 | C2 | NAG | C | 302 | 21.925 | 26.343 | 28.619 | 1.00 55.48 |
| ATOM | 1845 | N2 | NAG | C | 302 | 21.291 | 25.427 | 27.651 | 1.00 62.19 |
| ATOM | 1847 | C7 | NAG | C | 302 | 21.954 | 24.916 | 26.593 | 1.00 64.11 |
| ATOM | 1848 | O7 | NAG | C | 302 | 23.139 | 25.194 | 26.324 | 1.00 63.99 |
| ATOM | 1849 | C8 | NAG | C | 302 | 21.158 | 23.967 | 25.691 | 1.00 55.16 |
| ATOM | 1853 | C3 | NAG | C | 302 | 22.681 | 25.554 | 29.713 | 1.00 57.76 |
| ATOM | 1855 | O3 | NAG | C | 302 | 24.068 | 25.458 | 29.393 | 1.00 58.41 |
| ATOM | 1857 | C4 | NAG | C | 302 | 22.500 | 26.196 | 31.123 | 1.00 53.65 |
| ATOM | 1859 | O4 | NAG | C | 302 | 21.324 | 25.689 | 31.750 | 1.00 50.40 |
| ATOM | 1861 | C5 | NAG | C | 302 | 22.443 | 27.746 | 31.103 | 1.00 54.25 |
| ATOM | 1863 | O5 | NAG | C | 302 | 21.535 | 28.251 | 30.088 | 1.00 53.28 |
| ATOM | 1864 | C6 | NAG | C | 302 | 23.785 | 28.423 | 30.881 | 1.00 60.24 |
| ATOM | 1867 | O6 | NAG | C | 302 | 24.580 | 28.383 | 32.063 | 1.00 70.36 |
| ATOM | 1869 | C1 | NAG | C | 311 | 4.588 | 35.300 | -13.294 | 1.00 27.98 |
| ATOM | 1871 | C2 | NAG | C | 311 | 5.834 | 35.244 | -14.184 | 1.00 33.03 |
| ATOM | 1873 | N2 | NAG | C | 311 | 6.691 | 34.136 | -13.776 | 1.00 33.03 |
| ATOM | 1875 | C7 | NAG | C | 311 | 6.715 | 32.994 | -14.467 | 1.00 33.05 |
| ATOM | 1876 | O7 | NAG | C | 311 | 6.045 | 32.808 | -15.477 | 1.00 36.84 |
| ATOM | 1877 | C8 | NAG | C | 311 | 7.629 | 31.908 | -13.935 | 1.00 39.36 |
| ATOM | 1881 | C3 | NAG | C | 311 | 6.574 | 36.590 | -14.045 | 1.00 40.37 |
| ATOM | 1883 | O3 | NAG | C | 311 | 7.608 | 36.677 | -15.020 | 1.00 36.25 |
| ATOM | 1885 | C4 | NAG | C | 311 | 5.614 | 37.787 | -14.225 | 1.00 41.10 |
| ATOM | 1887 | O4 | NAG | C | 311 | 6.207 | 38.975 | -13.681 | 1.00 47.85 |
| ATOM | 1888 | C5 | NAG | C | 311 | 4.264 | 37.627 | -13.538 | 1.00 36.96 |
| ATOM | 1890 | O5 | NAG | C | 311 | 3.719 | 36.318 | -13.779 | 1.00 32.13 |

FIG. 1A-31

| | | | | | | | | | |
|---|---|---|---|---|---|---|---|---|---|
| ATOM | 1891 | C6 | NAG | C | 311 | 3.257 | 38.659 | -14.047 | 1.00 41.85 |
| ATOM | 1894 | O6 | NAG | C | 311 | 3.401 | 38.893 | -15.447 | 1.00 46.92 |
| ATOM | 1896 | C1 | NAG | C | 312 | 6.214 | 40.068 | -14.521 | 1.00 60.62 |
| ATOM | 1898 | C2 | NAG | C | 312 | 6.445 | 41.353 | -13.713 | 1.00 66.38 |
| ATOM | 1900 | N2 | NAG | C | 312 | 5.288 | 41.609 | -12.861 | 1.00 69.07 |
| ATOM | 1902 | C7 | NAG | C | 312 | 5.225 | 41.133 | -11.614 | 1.00 70.36 |
| ATOM | 1903 | O7 | NAG | C | 312 | 6.129 | 40.465 | -11.087 | 1.00 71.39 |
| ATOM | 1904 | C8 | NAG | C | 312 | 3.953 | 41.473 | -10.852 | 1.00 70.22 |
| ATOM | 1908 | C3 | NAG | C | 312 | 6.625 | 42.528 | -14.678 | 1.00 68.09 |
| ATOM | 1910 | O3 | NAG | C | 312 | 6.998 | 43.700 | -13.961 | 1.00 72.12 |
| ATOM | 1912 | C4 | NAG | C | 312 | 7.696 | 42.222 | -15.727 | 1.00 69.27 |
| ATOM | 1914 | O4 | NAG | C | 312 | 7.711 | 43.278 | -16.684 | 1.00 70.66 |
| ATOM | 1916 | C5 | NAG | C | 312 | 7.418 | 40.865 | -16.421 | 1.00 67.71 |
| ATOM | 1918 | O5 | NAG | C | 312 | 7.277 | 39.836 | -15.435 | 1.00 66.19 |
| ATOM | 1919 | C6 | NAG | C | 312 | 8.540 | 40.378 | -17.348 | 1.00 70.59 |
| ATOM | 1922 | O6 | NAG | C | 312 | 8.540 | 38.946 | -17.463 | 1.00 73.95 |
| ATOM | 1924 | C1 | NAG | D | 401 | 19.424 | 21.202 | -16.389 | 1.00 58.37 |
| ATOM | 1926 | C2 | NAG | D | 401 | 20.931 | 21.082 | -16.734 | 1.00 60.19 |
| ATOM | 1928 | N2 | NAG | D | 401 | 21.733 | 21.107 | -15.515 | 1.00 58.57 |
| ATOM | 1930 | C7 | NAG | D | 401 | 21.996 | 19.994 | -14.835 | 1.00 58.89 |
| ATOM | 1931 | O7 | NAG | D | 401 | 21.554 | 18.877 | -15.154 | 1.00 57.55 |
| ATOM | 1932 | C8 | NAG | D | 401 | 22.856 | 20.192 | -13.586 | 1.00 60.43 |
| ATOM | 1936 | C3 | NAG | D | 401 | 21.462 | 22.219 | -17.660 | 1.00 62.26 |
| ATOM | 1938 | O3 | NAG | D | 401 | 22.422 | 21.668 | -18.570 | 1.00 54.78 |
| ATOM | 1940 | C4 | NAG | D | 401 | 20.397 | 23.044 | -18.469 | 1.00 58.90 |
| ATOM | 1942 | O4 | NAG | D | 401 | 20.743 | 24.427 | -18.413 | 1.00 59.94 |
| ATOM | 1944 | C5 | NAG | D | 401 | 18.946 | 22.912 | -17.966 | 1.00 58.84 |
| ATOM | 1946 | O5 | NAG | D | 401 | 18.668 | 21.556 | -17.560 | 1.00 61.90 |
| ATOM | 1947 | C6 | NAG | D | 401 | 17.898 | 23.315 | -19.005 | 1.00 51.47 |
| ATOM | 1950 | O6 | NAG | D | 401 | 16.605 | 22.846 | -18.651 | 1.00 37.86 |
| ATOM | 1952 | C1 | NAG | D | 411 | 16.667 | 20.959 | -21.020 | 1.00 55.23 |
| ATOM | 1954 | C2 | NAG | D | 411 | 16.643 | 22.239 | -21.877 | 1.00 56.55 |
| ATOM | 1956 | N2 | NAG | D | 411 | 15.302 | 22.496 | -22.382 | 1.00 52.41 |
| ATOM | 1958 | C7 | NAG | D | 411 | 14.459 | 23.267 | -21.681 | 1.00 47.72 |
| ATOM | 1959 | O7 | NAG | D | 411 | 14.773 | 23.799 | -20.598 | 1.00 46.55 |
| ATOM | 1960 | C8 | NAG | D | 411 | 13.075 | 23.475 | -22.283 | 1.00 36.80 |
| ATOM | 1964 | C3 | NAG | D | 411 | 17.653 | 22.099 | -23.024 | 1.00 60.99 |
| ATOM | 1966 | O3 | NAG | D | 411 | 17.682 | 23.298 | -23.800 | 1.00 59.75 |
| ATOM | 1968 | C4 | NAG | D | 411 | 19.033 | 21.831 | -22.402 | 1.00 62.75 |
| ATOM | 1970 | O4 | NAG | D | 411 | 20.049 | 21.657 | -23.436 | 1.00 64.67 |
| ATOM | 1971 | C5 | NAG | D | 411 | 18.992 | 20.604 | -21.467 | 1.00 62.44 |
| ATOM | 1973 | O5 | NAG | D | 411 | 17.970 | 20.775 | -20.454 | 1.00 57.19 |
| ATOM | 1974 | C6 | NAG | D | 411 | 20.305 | 20.392 | -20.728 | 1.00 59.46 |
| ATOM | 1977 | O6 | NAG | D | 411 | 20.080 | 20.112 | -19.353 | 1.00 57.21 |
| ATOM | 1979 | C1 | NAG | D | 412 | 21.197 | 22.467 | -23.337 | 1.00 63.53 |
| ATOM | 1981 | C2 | NAG | D | 412 | 21.633 | 22.952 | -24.762 | 1.00 62.78 |
| ATOM | 1983 | N2 | NAG | D | 412 | 22.155 | 21.832 | -25.558 | 1.00 65.19 |
| ATOM | 1985 | C7 | NAG | D | 412 | 22.196 | 21.878 | -26.901 | 1.00 64.09 |
| ATOM | 1986 | O7 | NAG | D | 412 | 21.772 | 22.841 | -27.566 | 1.00 66.87 |

FIG. 1A-32

| ATOM | 1987 | C8 | NAG D 412 | 22.775 | 20.648 | -27.599 | 1.00 | 57.31 |
| ATOM | 1991 | C3 | NAG D 412 | 22.709 | 24.061 | -24.653 | 1.00 | 66.28 |
| ATOM | 1993 | O3 | NAG D 412 | 23.042 | 24.589 | -25.942 | 1.00 | 61.78 |
| ATOM | 1995 | C4 | NAG D 412 | 22.198 | 25.187 | -23.739 | 1.00 | 70.32 |
| ATOM | 1997 | O4 | NAG D 412 | 23.184 | 26.214 | -23.619 | 1.00 | 67.53 |
| ATOM | 1999 | C5 | NAG D 412 | 21.860 | 24.610 | -22.350 | 1.00 | 72.64 |
| ATOM | 2001 | O5 | NAG D 412 | 20.850 | 23.579 | -22.472 | 1.00 | 70.03 |
| ATOM | 2002 | C6 | NAG D 412 | 21.279 | 25.690 | -21.419 | 1.00 | 74.76 |
| ATOM | 2005 | O6 | NAG D 412 | 19.906 | 25.976 | -21.721 | 1.00 | 76.09 |

FIG. 1A-33

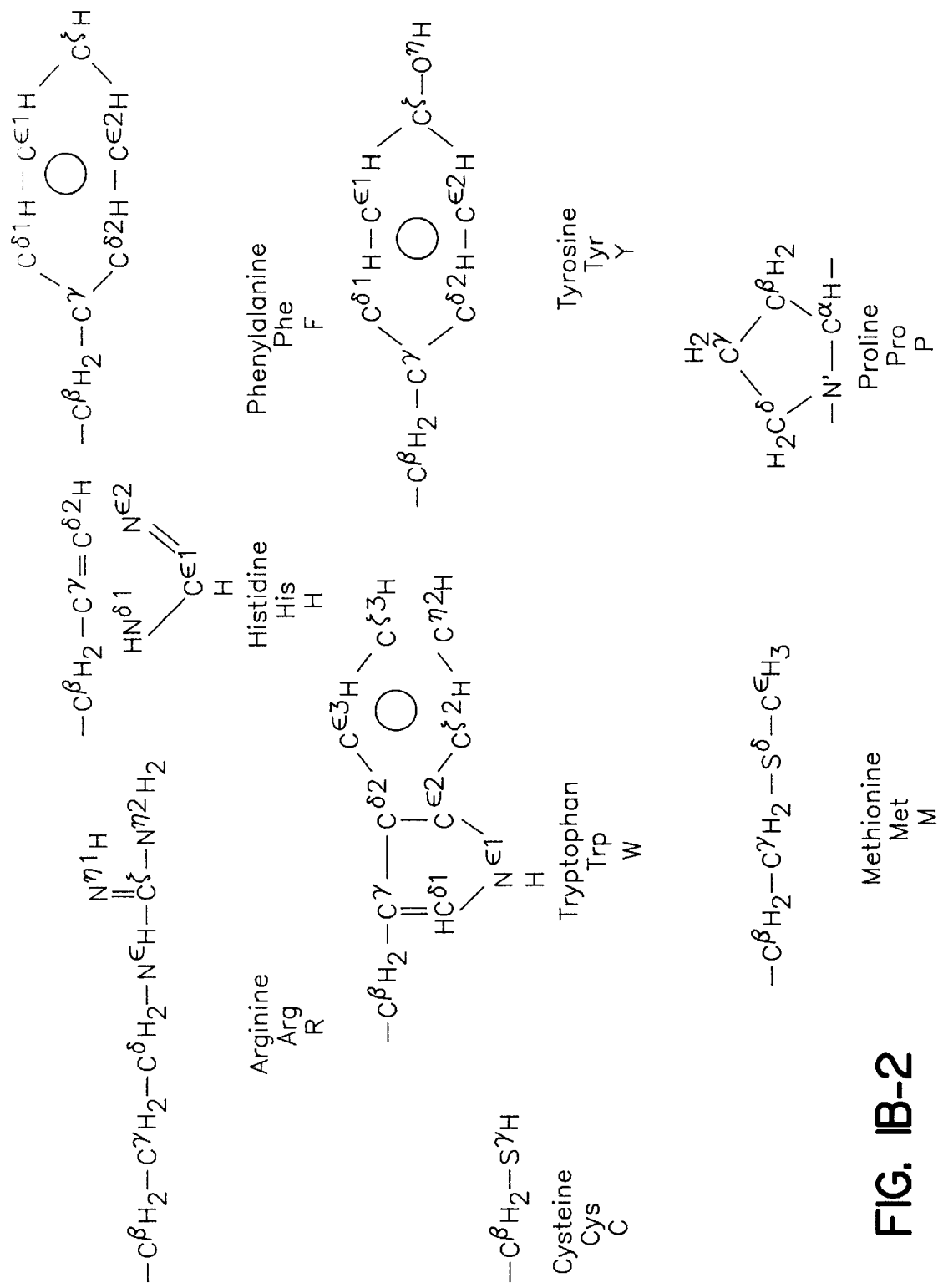
FIG. IB-2

α subunit

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| ALA | PRO | ASP | VAL | GLN | ASP | CYS | PRO | GLU | CYS | THR | LEU | GLN | GLU | ASN | PRO | PHE | PHE | SER | GLN |
| PRO | GLY | ALA | PRO | ILE | LEU | GLN | CYS | MET | GLY | CYS | CYS | PHE | SER | ARG | ALA | TYR | PRO | THR | PRO |
| LEU | ARG | SER | LYS | LYS | THR | MET | LEU | VAL | GLN | LYS | ASN | VAL | THR | SER | GLU | SER | THR | CYS | CYS |
| VAL | ALA | LYS | SER | TYR | ASN | ARG | VAL | THR | VAL | MET | GLY | GLY | PHE | LYS | VAL | GLU | ASN | HIS | THR |
| ALA | CYS | HIS | CYS | SER | THR | CYS | TYR | TYR | HIS | LYS | SER |

β subunit

SER LYS GLU PRO LEU ARG PRO ARG CYS ARG PRO ILE ASN ALA THR LEU ALA VAL GLU LYS

GLU GLY CYS PRO VAL CYS ILE THR VAL ASN THR THR ILE CYS ALA GLY TYR CYS PRO THR

MET THR ARG VAL LEU GLN GLY VAL LEU PRO ALA LEU PRO GLN VAL VAL CYS ASN TYR ARG

ASP VAL ARG PHE GLU SER ILE ARG LEU PRO GLY CYS PRO ARG GLY VAL ASN PRO VAL VAL

SER TYR ALA VAL ALA LEU SER CYS GLN CYS ALA LEU CYS ARG ARG SER THR THR ASP CYS

GLY GLY PRO LYS ASP HIS PRO LEU THR CYS ASP ASP PRO ARG PHE GLN ASP SER SER SER

SER LYS ALA PRO PRO PRO SER LEU PRO SER ARG LEU PRO GLY PRO SER ASP THR

PRO ILE LEU PRO GLN

FIG. 2

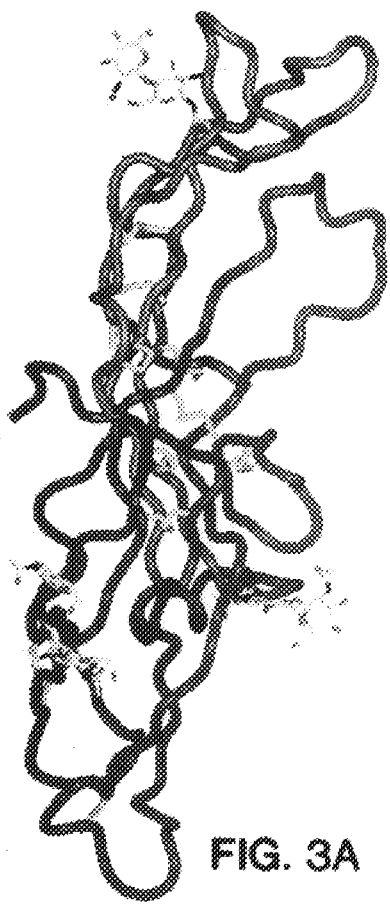
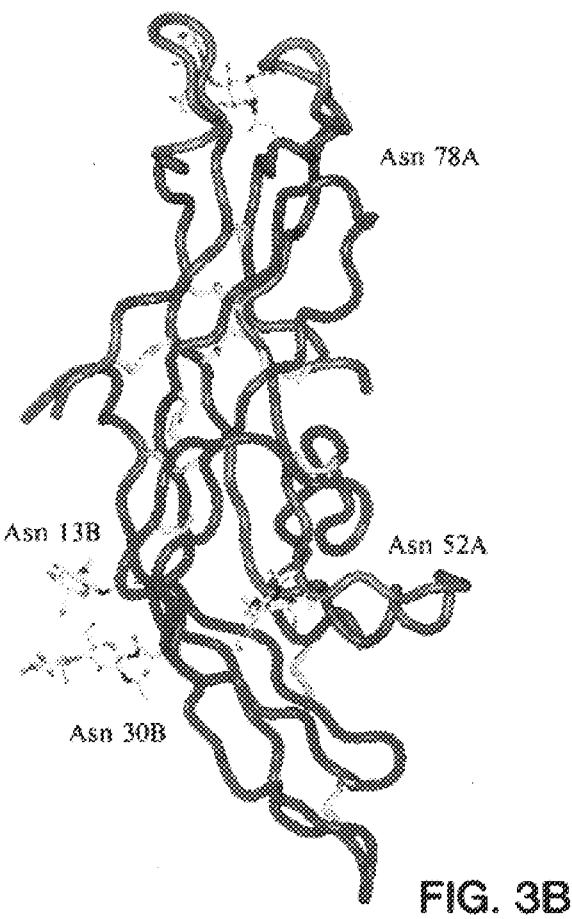
FIG. 3A
FIG. 3B disulphides 7-31
10-60*
28-82*
32-84*
59-87* disulphides 9-57*
23-72
26-110
34-88
38-90*
93-100

THREE DIMENSIONAL GLYCOPROTEIN HORMONE STRUCTURE REPRESENTATION USING A COMPUTER

TECHNICAL FIELD

The present invention relates to the three-dimensional structure of certain glycoprotein hormones having α and β subunits, such as human chorionic gonadotropin (hCG), and parts thereof having biological activity; and also to protein molecules whose three-dimensional structure approximates the hormone structure or part thereof (such as an agonist or antagonist) or is complementary thereto (such as an inhibitor).

Furthermore the invention relates to the computer assisted design of new analogues of glycoprotein hormones, such as hCG, follicle stimulating hormone (FSH) and luteinizing hormone (LH), having the same or modified biological activity; and relates also to the analogues designed in this manner and selected for chemical synthesis and screening.

BACKGROUND OF THE INVENTION

Human chorionic gonadotropin (hCG) is a member of the glycoprotein hormone family which includes follicle stimulating hormone (FSH), luteinizing hormone (LH) and thyroid stimulating hormone (TSH). These hormones are each composed of two subunits, α and β, which are noncovalently associated, forming a heterodimer. Within a given species the α subunit is identical whilst the β subunits are different (but homologous) for the different hormones. While the heterodimer is required for receptor binding, it is the β-subunit that confers the specific biological activity to each hormone. The glycoprotein hormones are all heavily glycosylated with N-linked complex carbohydrates, which are a source of natural heterogeneity within a given hormone. hCG is the most heavily glycosylated as it contains an additional four O-linked carbohydrates on the serine rich C-terminal extension of the β-subunit. In human glycoprotein hormones, the common α-subunit contains 92 amino acids with 10 half-cysteine residues, which form five intramolecular disulphide linkages. The β-subunit polypeptide varies in size from 114 residues in LH, to 145 in CG. The β-subunits contain 12 half cysteines which form six conserved disulphide bridges. Within the first 114 amino acids there is a high degree of sequence homology between hCG and the other hormones (LH 85%; FSH 36%; TSH 46%). The high sequence homology between hCG and LH reflects their common biological function in that both proteins elicit their biological action via the same receptor, whilst FSH and TSH bind to structurally similar, but distinct receptors.

Three-dimensional structure information is useful in being able to display in visual form on a computer screen, the shape of a molecule. The shape may be inspected from different angles by rotation thereof. It may also form the basis for methods of rational drug design. U.S. Pat. No. 5,331,573 discloses a method of rational drug design involving computer simulation of a polypeptide leading to prediction of three-dimensional structure changes which may result from postulated operator-selected changes in peptide chemical structure. U.S. Pat. Nos. 4,704,692 and 4,881,175 disclose computer based systems and methods for converting two naturally aggregated but chemically separate polypeptide chains into a single chain having a similar three-dimensional structure by selecting suitable linker sequences which maintain the original three-dimensional structura.

SUMMARY OF THE INVENTION

One aspect of the present invention provides a protein having a three-dimensional structure substantially according to FIG. 1 or a pharmacologically effective part thereof. Deletions, additions or substitutions in the amino acid sequence of the protein may be made provided that the three-dimensional structure is substantially maintained. In fact the amino acid sequence may be quite different from that of hCG provided that the overall three-dimensional structure is retained. The exerted biological activity is critically dependent upon the particular three-dimensional folding of the protein. The protein (possibly as a glycoprotein) may have utility in medicine, for example as a glycoprotein hormone agonist or antagonist.

In particular, the protein may be a conformational analog of hCG having a binding affinity for an hCG receptor, the analog having a three-dimensional structure substantially according to FIG. 1 or an effective part thereof having such binding affinity.

A further aspect of the invention provides a protein having a three-dimensional structure substantially according to the α-subunit of the structure according to FIG. 1 or effective part thereof; which may have utility as an agonist or antagonist of glycoprotein hormones including hCG, FSH, LH and TSH.

A further aspect of the invention provides a protein having a three-dimensional structure substantially according to the β-subunit of the structure according to FIG. 1 or a medicinally effective part thereof; which may have utility as an agonist or antagonist of hCG.

The invention also relates to the use of the proteins as growth factors in mammals, particularly domestic or agricultural animals; or in humans. Thus, the hormone like activity of the glycoprotein structures of the present invention may find particular use in the improved success of in vitro fertilisation techniques, and also techniques for treatment in vivo to enhance fertility. It may be unnecessary to employ the entire protein molecule. In particular, parts thereof which include receptor binding regions (e.g. β93–100, β35–58 and α88–92 as described in detail hereafter) may be employed.

Another aspect of the invention relates to a complementary protein having a structure substantially complementary to the three-dimensional structure according to FIG. 1; or to a medicinally effective part thereof, particularly a receptor binding region. A complementary protein is one whose three-dimensional structure is substantially complementary to the FIG. 1 structure or a part thereof, such that the complementary structure may bind thereto and may form a complex. The lifetime of the complex may be short in the case of a labile complex, or long in the case of an inhibiting complementary protein. Of course, binding will also require an appropriate choice of amino acid sequence. Such complementary protein may act as an inhibitor of the hormone. Such inhibitors may be used in vivo or in vitro to modify the activity of a hormone, particularly as growth factor or in fertility treatments as mentioned above.

A further aspect of the invention relates to the use of a protein having a structure substantially according to FIG. 1 or a part thereof (or a complementary protein or part thereof) for screening a compound for possible medicinal activity. In the pharmaceutical industry, new or known compounds are routinely screened for new uses employing a variety of known in vitro or in vivo screens. Often such screens involve complex natural substances and are correspondingly expensive to carry out, and the result may be difficult to interpret. The knowledge of the three-dimensional protein structure according to the invention allows a preliminary screening to be carried out on the basis of the three-dimensional structure of a reegion thereof, and the structural similarity of a molecule which is being screened. This is usually carried out in conjunction with a knowledge of the amino sequence of the region. Such screening can conveniently be carried out using computer modelling techniques, which match the three-dimensional structure of the protein or part thereof (or complementary protein or part thereof) with the structure of the molecule being screened. Potential agonist or inhibitor activity may be predicted. This screening test system is applicable to the whole family of gonadotrophins.

Chemical changes can be made in the structure of the glycoprotein in order to evaluate their effect on the overall three-dimensional shape. By "chemical change" we mean a change in the molecular make-up of the glycoprotein molecule, e.g. by changes in amino acid sequence or glycosylation.

A still further aspect of the invention relates to antibodies (including monoclonal antibodies) directed to the protein or complementary protein, for the detection thereof or for the modulation of its medicinal activity.

Thus, the three-dimensional structure of human chorionic gonadotropin has been determined by X-ray crystallography at 3.0 A resolution. The topology of both the alpha and beta subunits is similar. Three disulphide bonds in each form a cystine-knot which maintains a structure consisting of a double stranded, irregular, β-sheet on one side of the cystine-knot and two twisted and distorted β-hairpin folds lying somewhat parallel to each other on the other side of the central knot. The heterodimer is formed by an overlaying of the two subunits and is stabilised by the formation of a short β-barrel involving β-strands from both subunits. Furthermore a loop of the β-subunit between Cys 100 and Cys 110 is wrapped around the outside of the α-subunit and acts as a 'seat belt' in maintaining the heterodimer.

The invention also relates to use of the three-dimensional structure of a glycoprotein hormone, such as hCG, for designing new proteins or compounds for screening for improved or altered agonistic or antagonistic biological activities. As a result, the production efficiency, bioavailability, immunogenicity, stability, etc. may be favourably changed in such proteins or compounds with respect to their therapeutic application.

One aspect is that glycosylation sites can be altered e.g. introduced in or deleted from the protein by genetic engineering techniques. A requirement for N-glycosylation is the availability of the following consensus amino acid sequence: Asn-X-Ser/Thr in which X can be any amino acid with the exception of Pro. However, there are numerous positions where in principle an additional consensus sequence in the structure can be introduced by genetic engineering techniques. For example: in the beta subunit of hCG there are 4 Asn residues of which two are already glycosylated, one is N-terminal to a Pro residue leaving one candidate for glycosylation, Asn 58, by mutating Arg 60 into a Ser or Thr residue. For Ser and Thr the situation becomes more complicated. There are 23 occurrences of these amino acids in the beta subunit of hCG. About 15 of them could in principle be part of the consensus sequence (an Asn could be introduced by single point mutation). The other 8 Ser or Thr residues are already glycosylated or not appropriate for other reasons. It is clear that when one starts to consider two point mutations, the number of possibilities would increase enormously. By evaluating the three-dimensional structure, favourable sites located at the protein surface that do or do not interfere with the regions of the hormone associated with receptor binding and/or signal transduction can be located. Many possible glycosylation sites can be ruled out because the site is not located at the protein surface or interferes with the dimer contacts, etc. Thus, the 3D-structure can be used as a screen to facilitate selection of the most favourable candidates for mutation.

It will be clear also that two or three single point mutations can be provided in a single glycoprotein hormone analogue. Also by combining mutations on various sites of the glycoprotein many variations are possible.

In order to assist the selection of locations on the protein surface where additional glycosylation sites can be introduced, the following considerations are important; all of which are determined by the three-dimensional structure of the glycoprotein hormone. First, one should generally ensure that the potential glycosylation site is positioned at the protein surface and not in the interior of the protein. Second, one should avoid interference with putative receptor binding sites, other glycosylation sites and inter-domain interactions. This can be done by visual inspection of the three-dimensional structure or by calculation and analysis of the corresponding distances directly from the coordinates. Third, the residues that are candidates for site specific mutation should be sterically accessible and the side chain of the amino acids should preferably be oriented towards the surrounding liquid solution in order to enhance the probability of becoming fully glycosylated. Finally, in order to affect the overall structure and folding of the glycoprotein hormone to a minimal extent, conservative mutations are preferred. Thus, single point mutations are most attractive, followed by double mutations.

Another aspect of the invention provides that functional regions such as e.g. receptor binding and signal transduction regions of the glycoprotein hormones, are connected via (oligo)peptide linkers, or other chemical entities. There are numerous possibilities for introducing connections or links. These functional regions need not be located on the same subunit; only the 3D configuration and spatial arrangement (e.g. loops) needs to be preserved. In the resultant protein regions that are not essential for the receptor binding and/or signal transduction may be deleted or short-cut. The three-dimensional structure again provides structural selection criteria for doing this.

The effect of these mutations can be assessed with the aid of computer technology, so that promising candidates for synthesis and screening for biological activity can be selected. Thus a principle aspect of the present invention provides a method of representing and selecting an analogue structure of a glycoprotein hormone which mimics the three-dimensional structure of said glycoprotein hormone; which comprises (i) inputting the three dimensional coordinates of atoms of the glycoprotein hormone molecule into a computer and storing said inputted three-dimensional co-ordinate data in memory means; the computer having a data input means, a visual display means, and said memory means loaded with three-dimensional molecular simulation software; the simulation software being operable to retrieve said co-ordinate data from said memory means and to display a three-dimensional representation of the glycoprotein molecule on said visual display means and being operable to produce a modified three-dimensional analogue representation responsive to operator-selected changes to the chemical structure of said glycoprotein hormone and to display the three-dimensional representation of the modified analogue;

(ii) displaying the three-dimensional representation of said glycoprotein hormone molecule on said visual display means;

(iii) inputting into the data input means of said computer operator-selected changes in chemical structure of said glycoprotein hormone molecule, to produce an analogue structure of said glycoprotein hormone;

(iv) executing said molecular simulation software, the software producing a modified three-dimensional molecular representation of said analogue structure;

(v) displaying the three-dimensional representation of said analogue on said visual display means, whereby changes in three-dimensional structure of the glycoprotein molecule consequent on changes in chemical structure may be visually monitored; and (vi) selecting an analogue structure represented by a three-dimensional representation wherein the three-dimensional configuration and spatial arrangement of regions involved in receptor binding and/or signal transduction of said glycoprotein hormone remain substantially preserved.

The following description includes a typical protocol for carrying out the invention. First the atomic coordinates of the glycoprotein hormone (which may or may not include the coordinates of the H atoms) are read into a computer loaded with a molecular simulation and/or visualization software package and stored in the computer memory. Such software packages are commercially available or have been developed and programmed by academic institutions and/or individual persons. Examples of such packages are Quanta/CHARMm, Sybyl, Insight/Discover, Chem-X, Cerius-2, MidasPlus, etc. Such software packages allow the display, manipulation, analysis, and simulation of (glyco)proteins and other molecules of biological interest. See e.g. N. C. Cohen et al., in J. Med. Chem. 33:883–894 (1990), D. B. Boyd, in Rev. Comput. Chem. 3:223–247 (1992). The various features of the molecule under study can be highlighted, coloured and displayed, employing various display styles. By running the software on a fast, high-performance graphics workstation, such as those available from Silicon Graphics, Hewlett Packard, Evans and Sutherland, real-time manipulation and visualization of complex molecular systems is possible. In addition distances, angles, and dihedral angles of atom selections can be obtained.

The software package typically also provides so-called fragment libraries. These are databases in which are stored distances between atoms in proteins for which the crystal structure is known. Such fragment libraries may be used to find fragments from proteins that have the right conformation and number of amino acid residues necessary to connect two given residues at a given distance and orientation in the protein under study. See e.g. T. A. Jones et al., in EMBO J. 5: 819 (1986). This tool may be useful for determining the minimal or optimal number of residues to connect functional alpha and beta subunits. The required number of amino acids is dependent on the choice of the "anchor-points" in each subunit. If these anchor-points are spatially close, in principle short oligosaccharides will be able to connect the two anchor-points. When the anchor-points are spatially further away, in general longer sequences will be needed. Again the 3D-structure is an absolute necessity in order to carry out these calculations.

Another requirement for such connection peptides and/or other engineered peptides or protein fragments may be the preferred secondary structure. It is common knowledge that particular sequences of amino acids prefer or induce well-defined secondary structural motifs, e.g. beta-hairpins, and alpha helices; This is discussed for example in J. S. Richardson et al., Prediction of Protein Structure and the Principles of Protein Conformation (G. D. Fasman, Ed.), pp 1–98, Plenum Press, New York (1989). Thus when one wants to shorten a certain beta-hairpin loop in a gonadotropin, one should delete a number of amino acids from that loop while simultaneously creating a number of beta hairpin inducing amino acid residues by single point mutations.

The effect of the suggested alterations can be evaluated by carrying out so-called energy calculations. See e.g. Vasquez et al., in Chem. Rev. 94: 2183–3329 (1994). The modelling packages described above all offer the possibility to do energy calculations, in particular force field-based energy minizations, molecular dynamics, etc. The input for such calculations consists of the coordinates of the three-dimensional structure of the altered protein, a force field in which the chemical and physical parameters of the amino acids and/or other constituents of the altered glycoprotein hormone are described, and particular parameters that specify the exact form of the potential energy equation. The following general form is mostly used:

$$E = E_{bonded} + E_{nonbonded}$$

in which $$E_{bonded} = \sum_{bonds} k_b (b - b_e)^2 + \sum_{angles} k_\theta (\theta - \theta_e)^2 + \sum_{dihedral} k_\phi [I + \cos(n\phi - \delta)]$$

and $$E_{nonbonded} = \sum_{\substack{nonbonded \\ i,j\ pairs}} 4\,\delta_f \left[ \left( \frac{\sigma_{ij}}{r} \right)^{12} - \left( \frac{\sigma_{ij}}{r} \right)^{6} \right] + \sum_{\substack{charged \\ i,j\ pairs}} \frac{q_i q_j}{\delta f}$$

The three terms of the $E_{bonded}$ formula describe the bonded contributions to the energy (bond lengths, bond angles, dihedral engles) while two terms of the $E_{nonbonded}$ formula describe the nonbonded contributions (van der Waals and electrostatic interactions). The symbols k,b,$\phi$, $\delta$, $\epsilon$, $\sigma$, $\theta$, q, etc. have known conventional meanings and are given for all relevant combinations of atoms in the force field. The modelling software usually has computer algorithms (Newton-Raphson, steepest descent, conjugate gradient) that allow the optimization of the structure while minimizing the total potential energy.

The assumption is that structures at a minimum potential energy, will only show minimal conformational changes while distorted molecules will typically change drastically.

Important for the design of new glycoprotein hormones are the previously published structure-activity relationships of the glycoprotein hormone family. These data provide information on areas of the gonadotropin which are essential for dimer formation, receptor binding, signal transduction, etc. In addition, the 3D-structure also gives information on which disulfide bonds are formed between the various cysteine residues.

As the glycoprotein hormone, follicle stimulating hormone (FSH), luteinizing hormone (LH) and thyroid stimulating hormone (TSH) all are expected to have a similar three dimensional structure to hCG (they all possess the same alpha subunit). Therefore, based on the three dimensional structure of hCG homology built models of FSH, LH and TSH can also be constructed. Thus, using the same methods, similar analogues as described for hCG can also be prepared for FSH, LH and TSH.

Peptidomimetic compounds which have been designed by the invention and selected for further testing may be synthesized chemically. However, since sugar chains are known to be important for in vivo biological activity, production by way of recombinant DNA technology is to be preferred. By selection of a proper host cell line glycosylated proteins will be secreted in the culture medium. A variety of cell lines can be used such as insect cells, yeast cells and mammalian cells. CHO cells are an obvious choice since it is known that these cells are able to produce biologically active recombinant glycoprotein hormones. A recombinant hormone analogue according to the invention can be produced by transfection of host cells with mutagenized subunit genes the transcription of which is brought under control of strong promoters. The nucleotide sequences of the glycoprotein subunit genes and deduced amino acid sequences have been described in literature. They have been isolated by several groups to be used for expression in host cell lines. Using standard molecular biology techniques, mutations i.e. insertions, substitutions or deletions can easily be introduced. Point mutations can be introduced e.g. by site directed mutagenesis. As an alternative, overlapping PCR can be performed using the "natural" genes as amplification templates. The latter technology is also suitable to insert or delete larger DNA regions, for instance, DNA regions coding for peptides which connect different functional parts of the molecule.

The expression and purification of the analogues should lead to quantities that are suited for use in receptor binding and in vitro and in vivo biological activity assays. If needed, based on the outcome of such biological studies, remodelling can be performed.

Assays to determine affinity towards a receptor and to determine biological activity are already in use in the preparation of natural FSH batches and are known to those skilled in the art, and may be employed to assess the biological activity of analogues selected according to the present invention.

DESCRIPTION OF THE DRAWINGS

Embodiments of the present invention will now be described by way of example only, and with reference to the attached Figures wherein:

FIG. 1a (-1-24) is a listing of the three-dimensional co-ordinates of the atoms of the α and β subunits of hCG.

FIG. 2 is the known amino acid sequence of hCG (the α subunit is SEQ ID NO:1, and the β subunit is SEQ ID NO:2);

FIGS. 3a and 3b are views at right angles of the three-dimensional structure of hCG (the terms "A" and "B" that follow amino acid residue numbers refer to the α and β subunits, respectively);

DETAILED DESCRIPTION OF PREFERRED EMBODIMENTS

Figures 1, 1B:
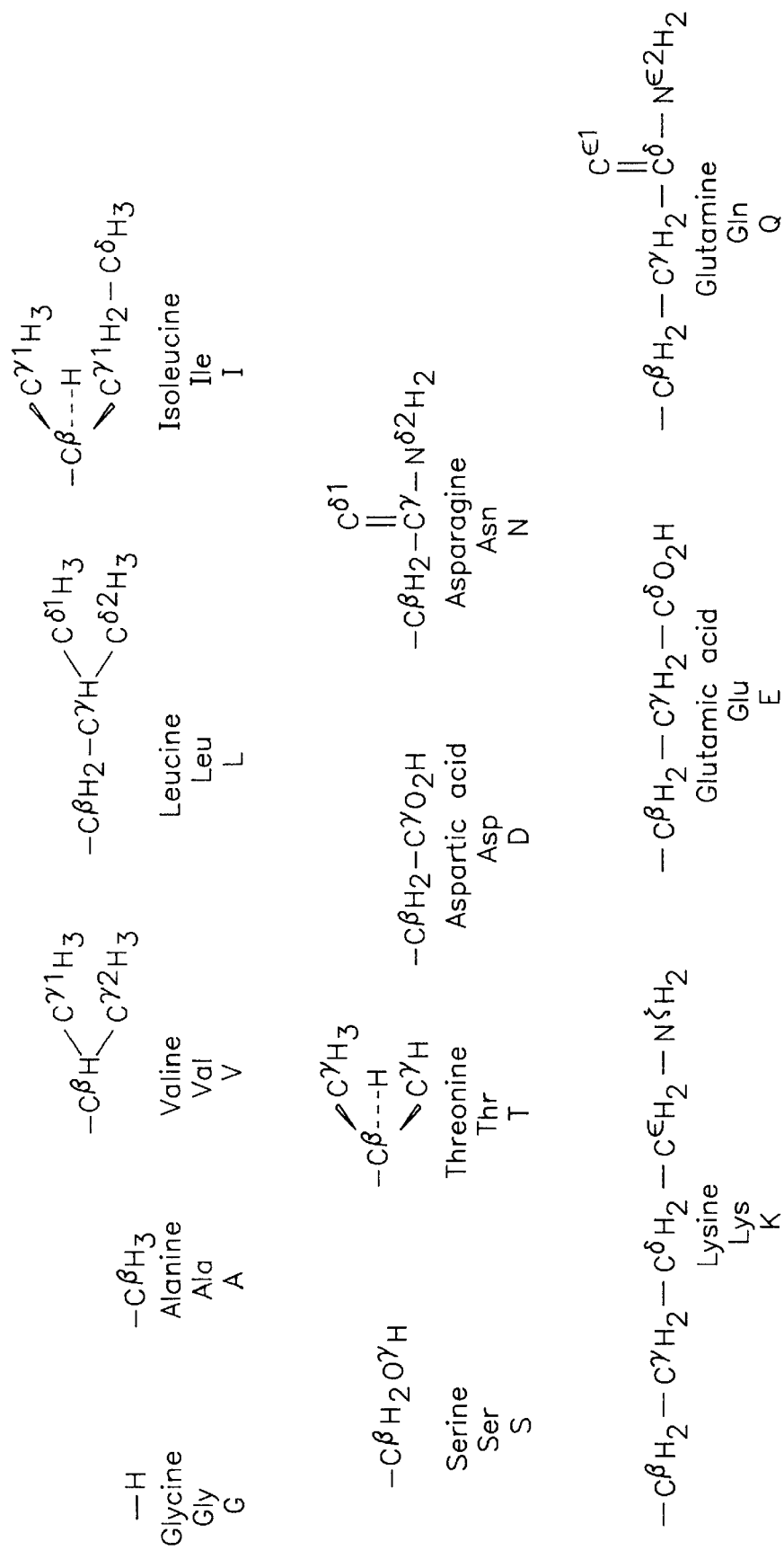
FIG. 1b shows labelling of atoms in the amino acids as employed in the listing.

FIG. 1a is a listing of the three-dimensional co-ordinators of the atoms of the α and β subunits of hCG.

The atom listing is preceded by a CRYST1 card which gives the dimensions (in Å) of the crystallographic unit cell. The next three cards define a matrix which converts co-ordinates from orthogonal Angstrom to fractions of the unit cell. Each atom card gives the (arbitrary) atom number, the atom label as per the attached sheet (the atoms of each amino acid main chain are labelled N. CA, C, O; the atom type is inferred from the first letter of the label and the atom position α, β, δ, ε, ζ, η, is given as A,B,G,D,E,Z,H respectively), the amino acid residue type, the protein chain label (A for α; B for β) and the amino acid sequence numbers (for the β-subunit, 100 has been added to each number). The first three numbers give the orthogonal X, Y, Z co-ordinates of the atom in Å. The next number is an occupancy number and would be less than 1.0 if the atom could be seen in more than one position i.e. the amino acid could be seen in more than one orientation. The final number is a temperature factor which relates to the thermal amplitude of vibration of the atom. The atom numbering is arbitrary and the calculated coordinates of H atoms are omitted.

At the end of the listing are carbohydrate residues labelled NAG (for N-acetylglucosamine). These are attached to the protein at four positions (Asn 52 and 78 on α, Asn 13 and 30 on β).

STRUCTURE DETERMINATION AND REFINEMENT

Conditions for crystallising HF treated hCG (HF-hCG) have been reported (Harris at al., 1989) and it is these crystals which have been used in the structure determination reported here.

HF treated hCG crystallises from ammonium sulphate solutions (Harris et al., 1989) as hexagonal bipyramids with the space group $P6_{522}$ and cell dimensions a=88.68, c=177.24 Å. The crystals diffract to 3.5 Å resolution on a laboratory X-ray source and to 2.5 Å with synchrotron radiation, though they are extremely sensitive to radiation damage in the synchrotron beam. The structure has been determined to 3.0 Å resolution by multiple isomorphous replacement (MIR) with relatively poor heavy atom derivatives. Solvent flattening made a marked improvement to the phasing, but not sufficient to allow an unambiguous tracing of the electron density map, or a determination of the boundary between the α/β subunits. Using the program Mice rounds of maximum entropy (ME) solvent flattening were performed with one round to phase permutation. Further rounds of ME solvent flattening, in combination with partial structure phase combination, produced significant improvement in the phasing.

The final electron density map allows a tracing of the α-subunit from residues 5 to 89 and the β-subunit from 3 to 112. The residue β-112 is open to a large solvent cavity and we assume that the remaining C-terminal 33 residues adopt a random conformation and are thus not visible in the map.

The initial model was refined using the program XPLOR. Five rounds of refinement and model building gave a final structure. No solvent molecules but six N-acetylglucosamine molecules positioned in good density have been included. A geometric analysis of the refined structure with the program PROCHECK gave values better than expected for structures determined at this resolution.

1a) THE DISULPHIDE BRIDGES

Central to the successful map interpretation and thus the three-dimensional structure elucidation was the recognition of the disulphide bridges and their correct assignment to positions in the amino acid sequence for each subunit. This assignment is different from the one generally accepted in the literature. There are five disulphide bonds in the α-subunit and six in the β-subunit. The chemical assignment of the disulphide pairings has been the topic of many studies (for review see Ryan et al., 1987), with no complete agreement having been reached. However, it has been accepted that the following assignments are correct: α7–31, α10–32, β93–100, β26–110 and perhaps β23–72. From the ME phased map some electron density could be interpreted as possible disulphide connections, but the close proximity of these regions prevented any unambiguous interpretation. However, some continuous lengths of density could be fitted with a polyalanine chain. In one of these, the separation between the positions of possible disulphide links positioned Cys 23, Cys 26 and Cys 34 of the β-subunit. Assuming the S—S linkages given by prior workers (23–72, 26–110, 34–88) enabled a sequence to be fitted from β3 to β38, β60 to β89 and β93 to β112 with the disulphide bridge β93–100 formed. With this partial sequence fitted, it became apparent that the remaining S—S bridges could not be formed as expected (i.e. 38–57, 9–90). The map could be interpreted only if the remaining linkages were formed from 9 to 57 and 38 to 90. This combination produces an unusual knot of three disulphide bridges. Once density had been assigned to the β-subunit, the remaining density contained a feature which could be recognised as a similar knot of cystines, but in order to fit the amino acid sequence to the density, disulphide linkages (10–60, 28–82, 32–84) different to those previously assumed were necessary. From this core, the remainder of the α-subunit could be traced.

This cystine-knot motif involves three disulphide bridges arranged such that two disulphides link adjacent anti-parallel strands of the peptide chain and form a ring through which the third disulphide penetrates. As well as a common arrangement in the sequence order of half cystines, two amino acid sequence motifs are associated with the cystine knot. Both of these sequence patterns are found in the subunits of hCG; α28–32(CMGCC), α82–84(CHC), β34–38(CAGYC) and β88–90(CQC). The disulphide pairings are given in Table 2. Of the linkages not predicted in any previous study, (α10–60, 28–82, 32–84, 59–87; β9–57, 38–90) all but one are involved in the cystine knots.

There is an unusual bend at Asn 15 of the α-subunit, where the sidechain of Asn forms hydrogen bonds to the main chain NH of residues 17 and 18 resulting in Pro 16. Phe 17 and Phe 18 bulging away from the antiparallel strand and forming a prominent feature on the surface of the molecule.

1b THE STRUCTURE OF THE PROTEIN SUBUNITS

Figure 6A:
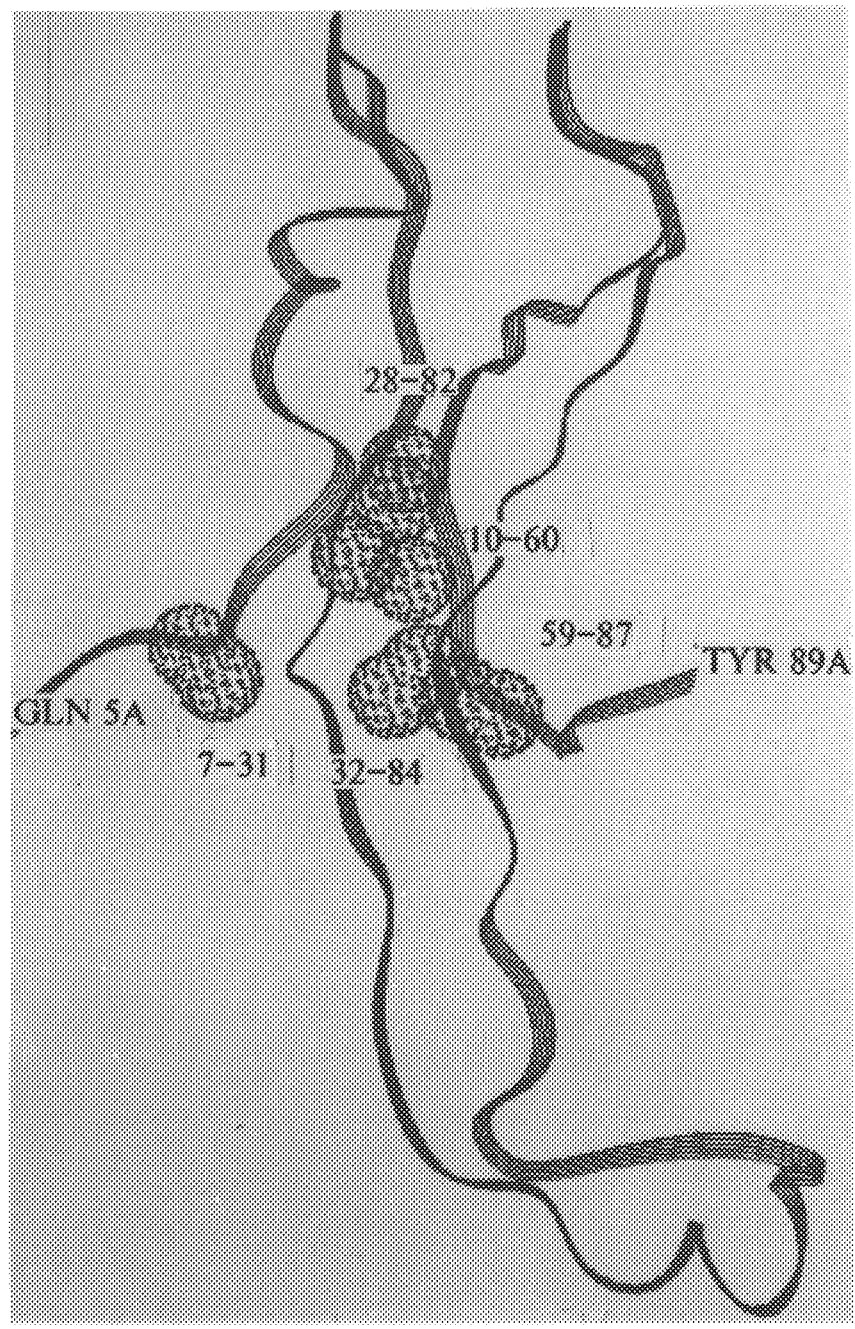
FIGS. 6a, 6b and 6c are views of the α-subunit, the β-subunit and the assembled heterodimer structure respectively of hCG showing the positions of disulphide bridges (the terms "A" and "B" that follow amino acid residue numbers refer to the α and β subunits, respectively)
Figure 6B:
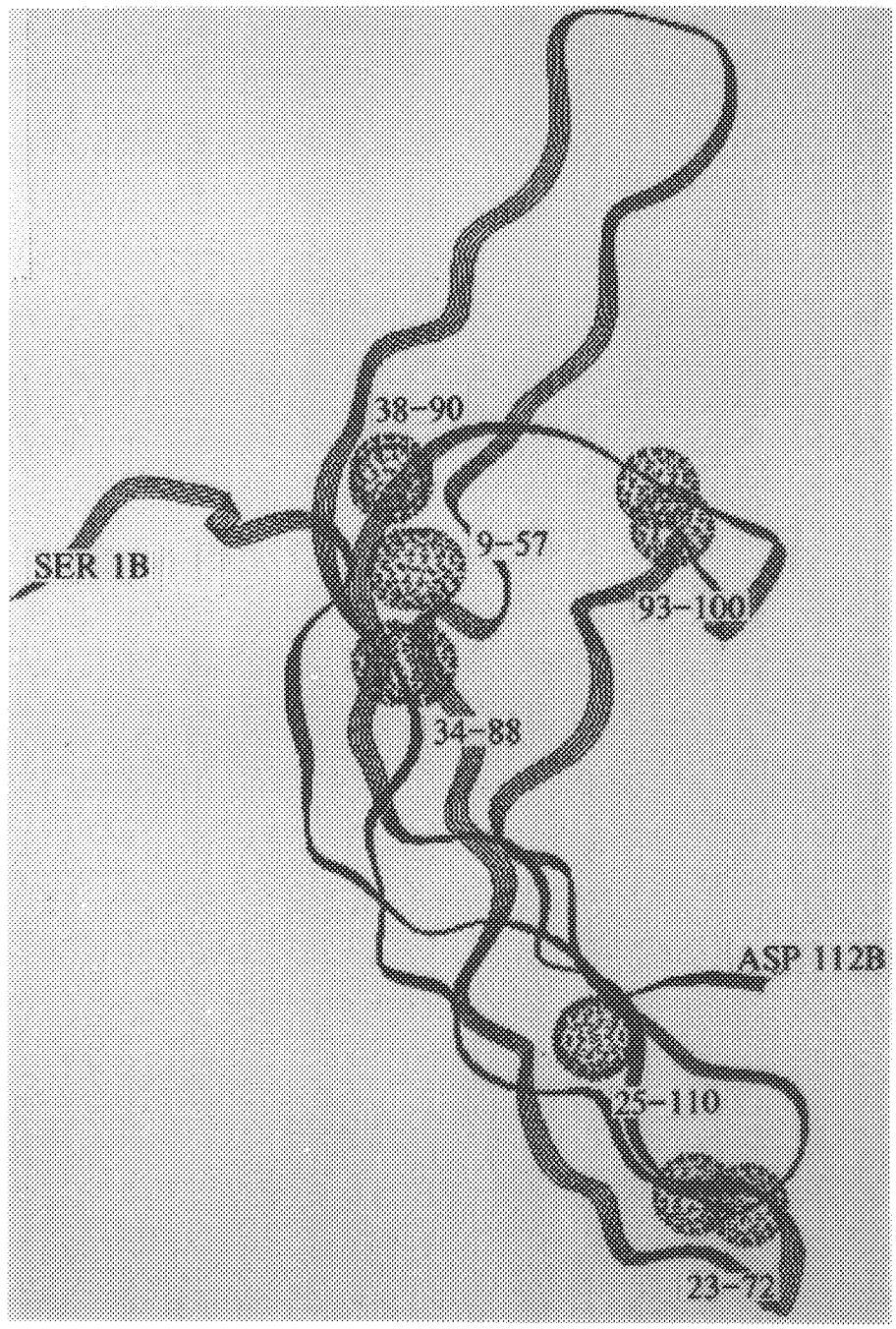

The subunits each have a similar fold which is determined largely by the central cystine knot. On one side of the knot, there is a loop of double-stranded β-sheet like structure, while on the other side there are two hairpin loops lying in almost parallel plates. In the β-subunit, these hairpins are linked by the Cys23–72 disulphide bond. FIGS. 6a and 6b show the fold of each subunit and indicate the positions of the disulphide bridges in each. The hairpin structure of each subunit is stabilised by a hydrophobic core extending between the two loops. The α-subunit core consists of Phe α17, Phe α18, Ile α25, Val α68, Val α70, Met α71, Phe α74 and Val α76, with the three phenylalanines clustered together and partially exposed to the surface. The β-subunit core includes the residues Leu β16, Val β18, Ile β27, Val β29, Ile β67, Leu β69, Val β80 and Tyr β82 which buries the disulpuhide bridge β23–72 to some extent.

In the C-terminal hairpin loops of each subunit there is a pair of β-bulges occurring at adjacent positions in each strand. In the β-subunit, both of these bulges have a 'classical' hydrogen-bonding pattern. In the α-subunit the hydrogen bond formation is less complete. The structures of all growth factors containing a cystine-knot have a β-bulge which is always located immediately before Cys(V) in the cystine knot, suggesting that it exists because of the arrangement of the cystine knot. Without the bulge, the normal right-handed twist always found in extended loops would lead to a steric clash between side chains on the inner side of the loop and the Cys(II)–Cys(V) disulphide in the cystine knot. The other hairpin loop has no equivalent feature as here the twist of the strands takes the side chain away from the disulphide.

In the isolated subunits the disulphides within the cystine knots show varying degrees of solvent accessibility. The disulphide Cys(I)–(IV) is buried in the knot, Cys(II)–Cys(V) is buried due to the contribution of three flanking residues (in a Leu 12, Ala 62 and His 79; in β Tyr 59, Ala 85 and Pro 111) but Cys(III)–Cys(VI) is left exposed to the solvent as are the retaining disulphide bridges.

In the α-subunit, the loop on the other side of the cystine knot consists of a stretch of anti-parallel β-sheet made up from residues 35 to 39 and 52 to 56. The three residues Pro 38- Thr 39- Pro 40, which are conserved in all 18 α-sequences determined, break the β-sheet and lead into two turns of a $3_{10}$-helix involving residues 40 to 46. This is the only helical structure in either subunit. The combination of a Pro-Thr-Pro sequence followed by a helix results in the end loop bending away from the β-sheet at an angle of about 100° to form a quite rigid structural element which is further stabilised by a H-bond between the Thr 39 side-chain and the main-chain on the anti-parallel strand. This conformation places Asn 52 on a bend which directs the N-linked carbohydrate on this residue away from the α-chain. At the extreme end of this loop are two conserved hydrophobic residues. Leu 48 and Val 49, which are both fully exposed to the solvent.

In contrast, the corresponding region of the β-subunit is less constrained and forms a very open loop. Away from the cystine knot region, there are no main chain H-bonds between the anti-parallel strands. Instead, the loop is stabilised by two side chain to main chain interactions. The side chain of Arg 43 is H-bonded to main chain carbonyls of Pro 50 and N of Leu 52 and the side chain of Gln 54 is H-bonded to the main chain N of Met 41. One side of the loop comprising residues 38 to 45, is held by association with the α-subunit. Residues 46 to 49 at the top of the loop are poorly defined in the electron-density map. In the crystal a two-fold axis of symmetry causes residues 48–50 to pack against the same residues from a neighbouring molecule.

Figure 7:
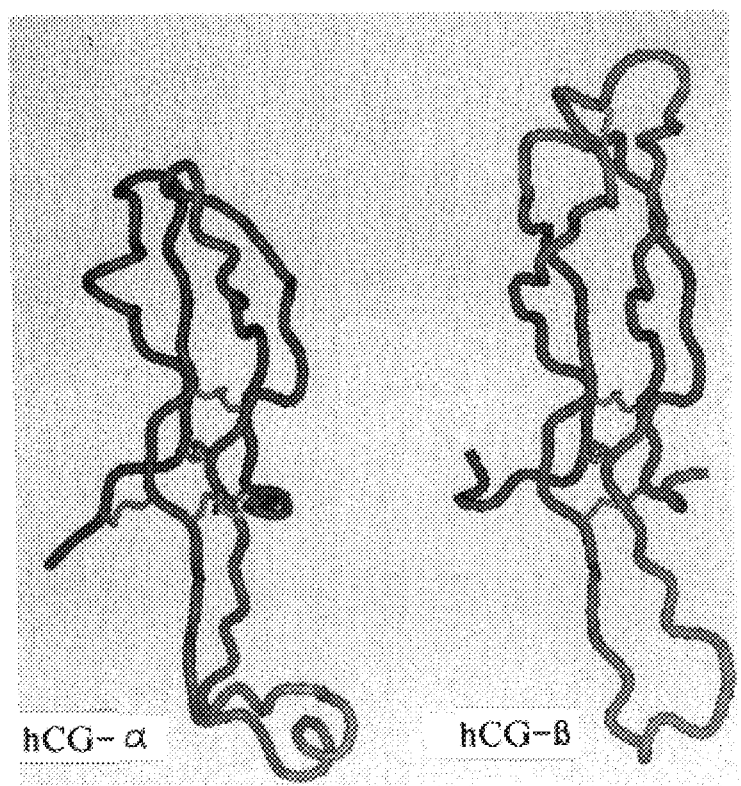
FIG. 7 compares a central cystine knot structure of hCG α and β subunits.

With the exception of the cystine-knot motif no sequence homology has been detected between the two subunits, but when residues forming the cystine knot in each protein are superimposed, a remarkable similarity in structure is apparent (FIG. 7). The Cα positions of 49 residues can be superimposed with a rms difference of 1.9 Å. The two structures have a common core structure and differ mainly in the extent of the loop regions. In the β-subunit the pair of hairpin loops are extended in size, while the double stranded loop on the other side of the cystine knot is longer in the α-subunit.

1c) THE FORMATION OF HETERODIMER

Figure 5A:
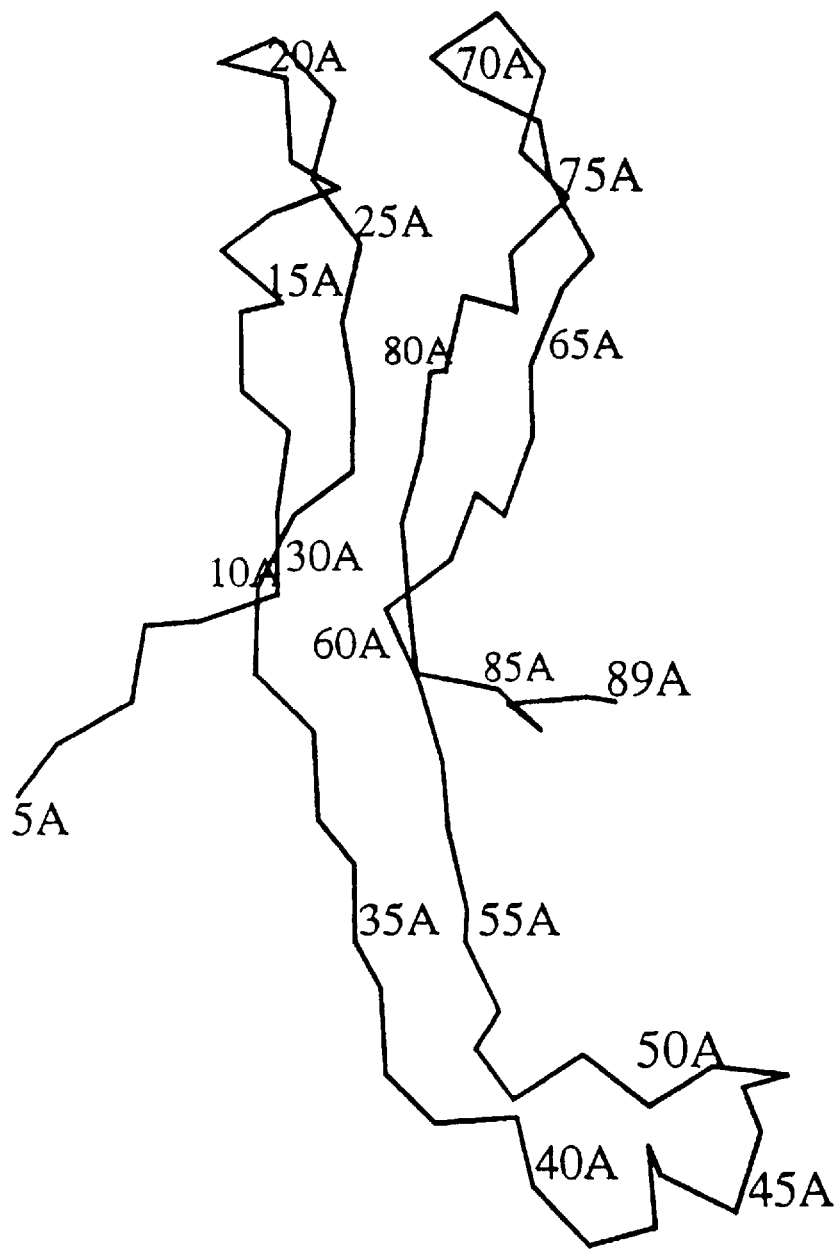
FIGS. 5a, 5b and 5c are views of the α-subunit, the β-subunit, and the assembled structure respectively of hCG (the terms "A" and "B" that follow amino acid residue numbers refer to the α and β subunits, respectively)
Figure 5B:
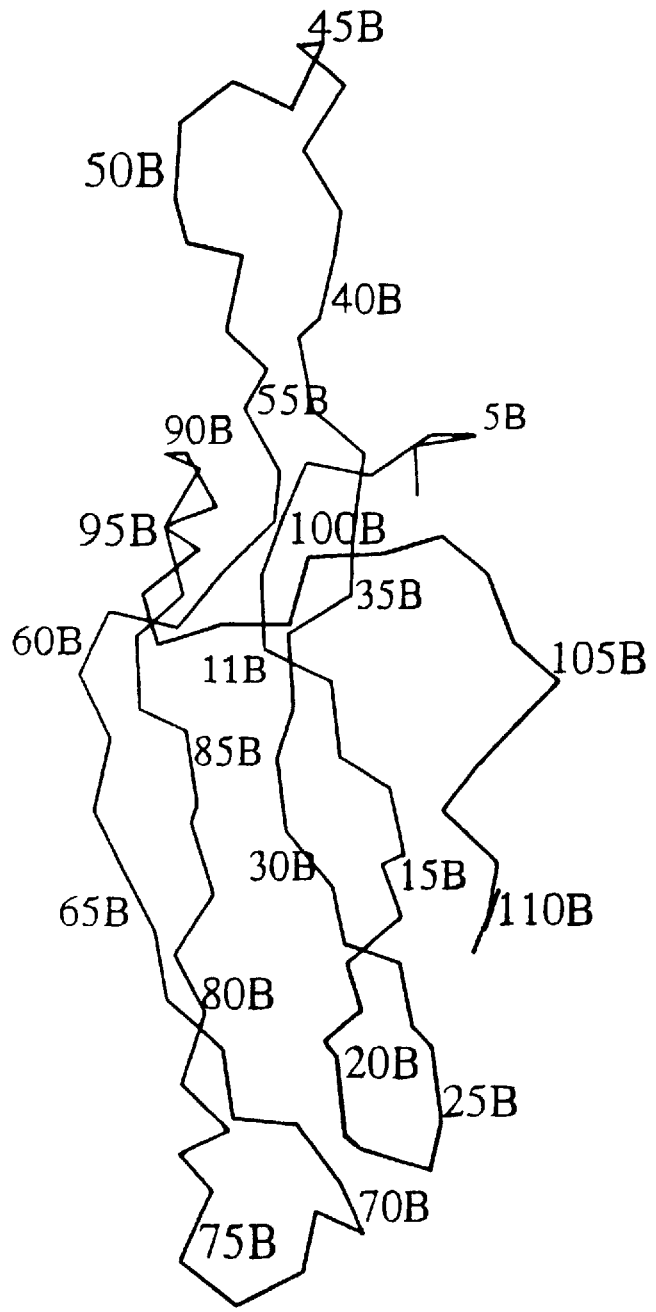
Figure 5C:
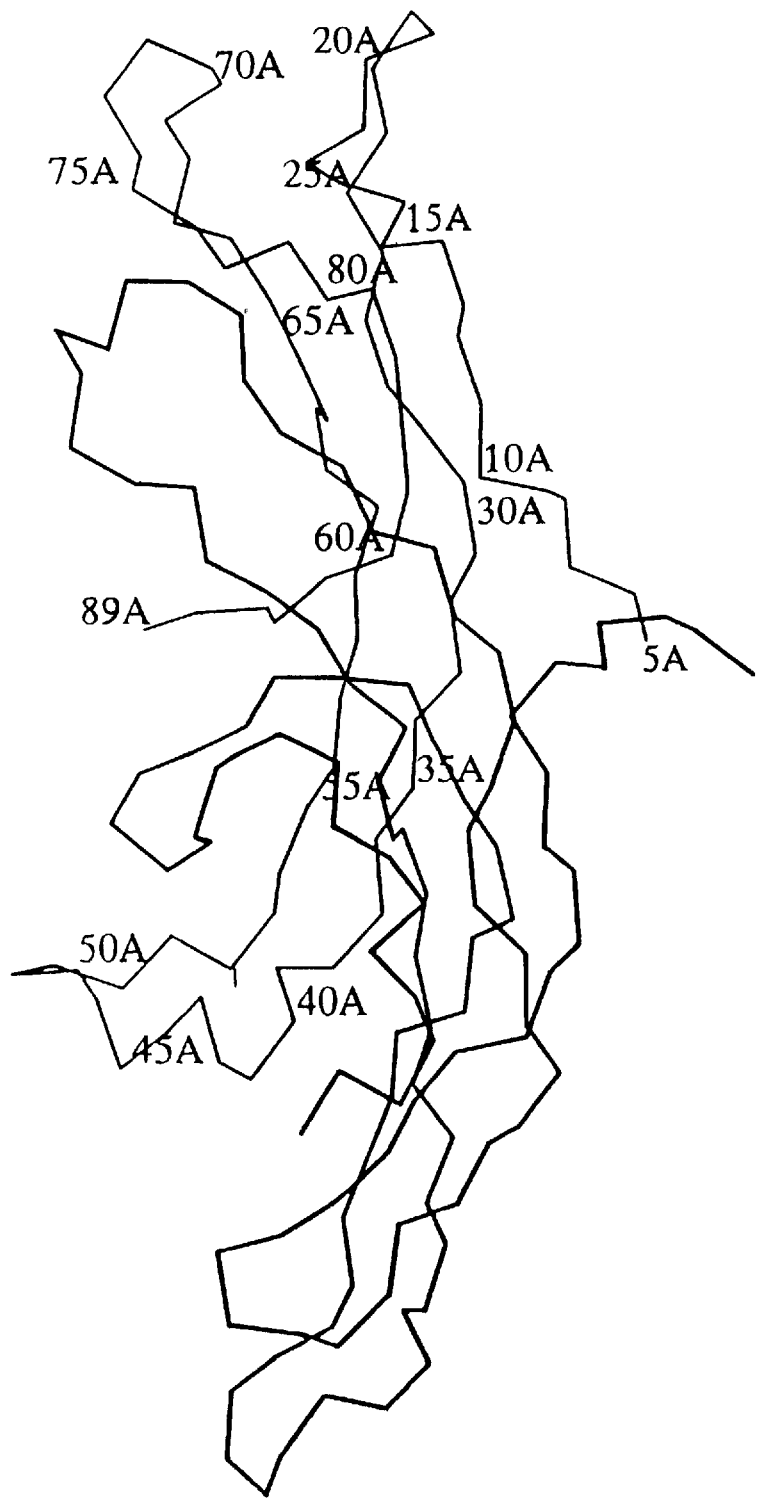
Figure 6C:
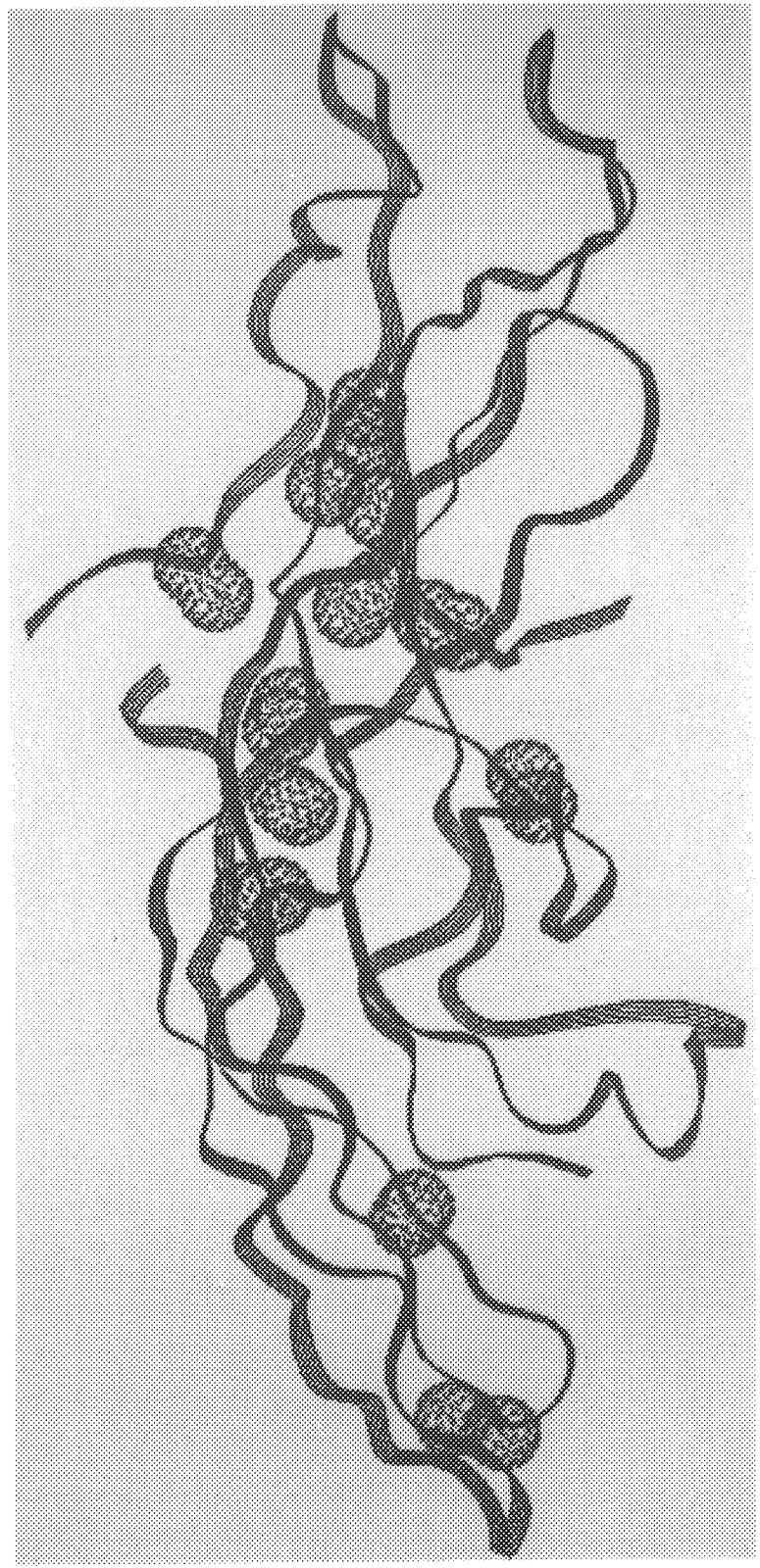

FIGS. 5c and 6c show the arrangement of the heterodimer. The two subunits are arranged with an approximate two-fold symmetry relating one subunit to the other. The segments of well defined β-sheet structure near the cystine knot in each subunit are brought together to form a short seven-stranded β-barrel. One face of this barrel consists of a short strand from the β-subunit (97–101) forming a parallel β-sheet with (52–60) which is part of a four stranded anti-parallel β-sheet consisting of α(52–60), α(37–29), β(33–40) and β(12-9). (The order of the sequence numbers indicates the direction of the strand). The central anti-parallel strands formed between the subunits includes the β34–36 (CAGY sequence) which has long been implicated in the formation of the dimer. The other face of the barrel is made up of two anti-parallel strands (84–90, 63–54) of the β-subunit. This complete association buries a surface area between the subunits. Away from this central region, there are hydrophobic contacts between Val 44 and Leu 45 of β and the triplet of Phe residues (17,18,74) in the α hairpin loop.

An unexpected feature of the dimer association is the role played by the loop between Cys 93 and Cys 110 in the β-subunit. This loop is an integral part of the β-subunit structure as disulphide bridges are formed between Cys 93–100 and Cys 26–110. (FIG. 6b). However, in the heterodimer this loop is wrapped over the α-subunit while remaining covalently bonded to the β-subunit through the disulphide linkages, giving the loop the appearance of a seat belt. There is close association between the inner surface of the belt and the α-subunit. A short strand of parallel β-sheet between β(97–101) and α(53–57) forms part of the central β-barrel. The side chains of the α-subunit residues covered by the belt point towards the belt and interact with either main chain or side chain atoms. The side chain of α35 Arg is H-bonded to the side chain of β106 His and to the main chain carbonyl of β104 Lys. Non-bonded interactions are formed between α37 Tyr, β107 Pro and β108 Leu and between α54 Thr and β99 Asp. The side chain of α56 Glu is H-bonded to the main chain of β104 Lys. There are no contacts which are specific to the hCG molecule which would prevent this seat-belt arrangement existing in all of the glycoprotein hormones.

The presence of CAV at Asn52 on the α-subunit would make it impossible for the α-subunit to slide under the β belt in the formation of the heterodimer and the most likely mechanism is one where the β26–110 disulphide bond is not fully formed until the dimer association is complete. Experiments performed by prior workers have shown that the formation of this disulphide is not completed until after the α/β association has occurred.

1d) CARBOHYDRATE STRUCTURE

In its native form hCG is heavily glycoslylated with carbohydrate making up approximately 34% by weight of the protein. There are two N-linked carbohydrates occuring at Asn 52 and Asn 78 on the α-subunit and two at Asn 13 and Asn 30 on the β-subunit. In addition the β-subunit has four O-linked carbohydrates at Ser 121, 127, 132 and 138. Treatment of the protein with anhydrous HF removes much of the carbohydrate. The HF treatment appears to leave the O-linked carbohydrate largely intact and will truncate the Asn linked carbohydrate on the α-subunit to Asn-(GlcNAc)$_2$(Man)$_3$.

There is clear electron density for some of the N-linked complex carbohydrates of both subunits. The O-linked residues are not seen.

In α, the carbohydrates are found at differing extremities of the molecule. Asn 52 is associated with the double stranded loop and Asn 78 is near the end of the twisted β-hairpins. The carbohydrate makes few hydrogen bonds to the protein but the first GlucNAc sugars is in close nonbonded contact with the protein and therefore could be expected to have an influence of the protein conformation.

In the β-subunit carbohydrates both N-linked are located together with the Cα's of Asn 13 and Asn 30 only 7 Å apart. This may explain why a number of glycoprotein hormones can have one or other of these Asn residues substituted without loss of function. In the hormones with both glycosylation sites, we would expect significant interactions between both carbohydrate chains. The sugars in the β-subunit, in contrast to those on the α-subunit, are exposed on the outward facing β strand of the first β-hairpin and form neither hydrogen bonds nor significant nonbonded contacts to the protein.

The overall distribution of the carbohydrate in the heterodimer is in two regions, the first (Asn 78) is between the twisted β-hairpins of α, while the second is a central band formed from the other N-linked carbohydrate, which spreads over both faces of the β-subunit (FIG. 3). The only carbohydrate which makes interactions at the subunit interface is at α52 Asn which makes contacts to the β-subunit residues, Tyr 59, Val 62, Phe 64, and Ala 83 as well as Thr 97, from the determinant loop.

1e) THE C-TERMINAL PEPTIDE hCG differs from hLH and the other glycoprotein hormones in having an extended amino acid sequence at the C-terminal end. This 31 residue C-terminal peptide has an unusual amino acid sequence, containing nine Pro and eight Ser residues, four of which are glycosylated. Although there is space in the crystal lattice to accommodate this peptide, the electron density after Asp 112 is very weak and it has not been possible to model any further residues for this portion of the structure. The most likely explanation is that the peptide does not adopt an ordered conformation and is thus highly mobile in the solvent cavity. It is also conceivable that the chain is lost due to acid catalysed cleavage of the peptide within the crystal but the observation that crystals of asialo-hCG are isomorphous with HF-hCG suggests the peptide is disordered in the crystal.

2) RECEPTOR BINDING

A number of residues important for the activity of hCG have been identified through chemical modification of the whole protein or subunits, or through the use of synthetic peptides in competitive inhibition studies. Also with the availability of recombinant hCG site-directed mutagenenis has been used. The present model further rationalises these findings and in particular the three-dimensional structure may be used in a test system for drug discovery.

Figure 4:
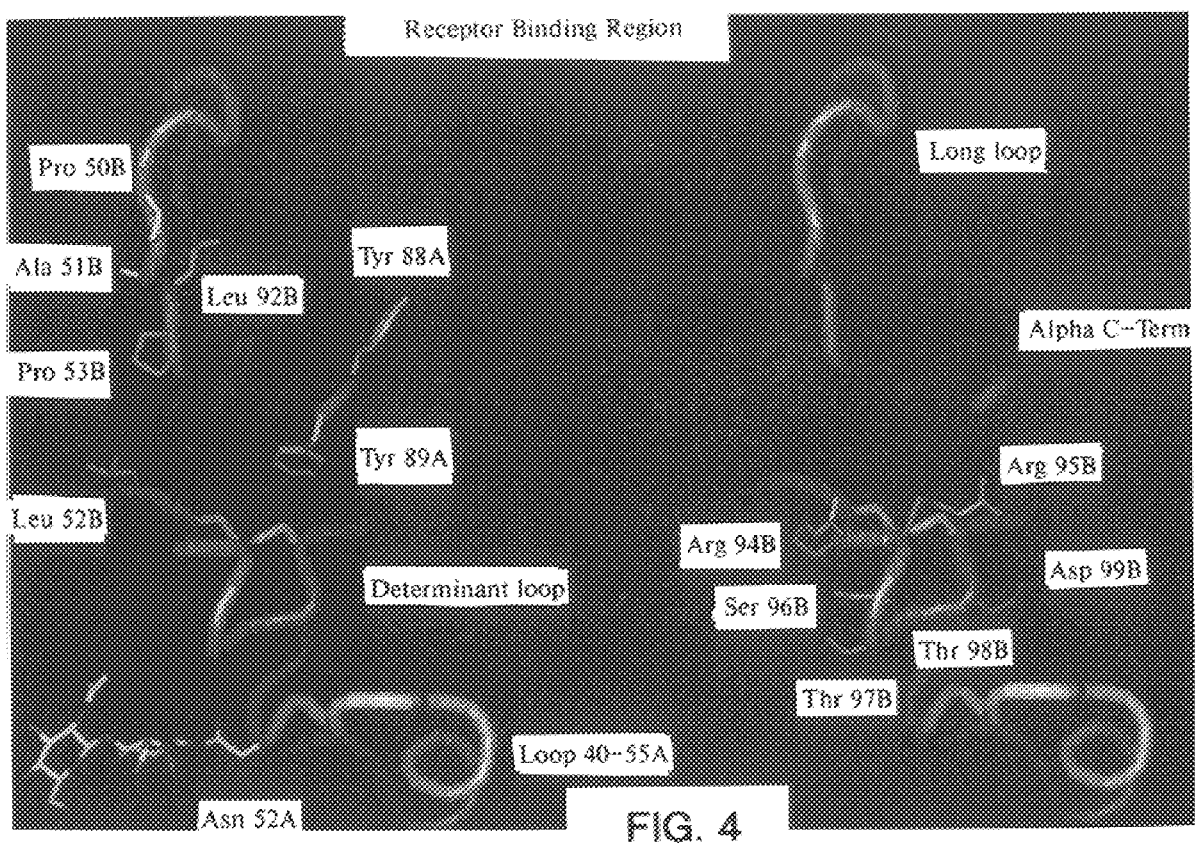
FIG. 4 shows receptor binding regions of hCG in detail (the terms "A" and "B" that follow amino acid residue numbers refer to the α and β subunits, respectively)

The combined results from all these approaches has been to locate a number of regions in both the α and β-subunits which contribute to receptor binding, (See FIG. 4).

1) The (β93–100) 'determinant loop' sequence

The importance of the sequence β93–100 was recognised by previous workers who proposed that the variability in charge in this loop would act as a determinnant of specificity, with positive charge for LH/hCG as opposed to the negative charge found for FSH and TSH. The disulphide 93–100 which forms this loop has been shown to be important for activity.

The structure reveals that the determinant loop is surface oriented and held in place by a short stretch of parallel β-sheet between α53–56 and β97–102. β98 Thr is buried at the interface with α, and its importance in subunit association has been implicated from mutagenesis studies. Residues implicated in receptor binding from site-directed mutagenesis (Arg 94, Arg 95, Ber 96 and Asp 99) are surface accessible in the dimer. Thr 97, which is generally insensitive to mutagenesis, is also surface accessible but does not contribute to the same surface as the other receptor binding residues. However, mutagenesis of this residue to Asp destroys receptor binding indicating that a negative charge in this region is not tolerated.

2) The (β35–58) 'long loop' sequence

Much attention has been focused on the longest intercysteine loop β35–58 which has been shown to stimulate steroidogenesis in rat Leydig cells and inhibit binding of whole hCG half-maximally at concentrations of $10^{-5}$M.

The crystal structure reveals an unusual loop with the N-terminal residues involved in the heterodimer formation. The conserved residue Val 44 is entirely buried at the α/β interface, and Thr 40, Met 41, Thr 42, Leu 45 and Gln 46 also make significant contributions to the buried surface at the diner interface. β35–45 adopts a β strand conformation and forms a short stretch of anti-parallel β-sheets with α27–31. There is a poorly defined section between β46 and 50. Pro 50 forms a turn and the section β50–57 forms an almost linear structure. Val 55 and 56 pass between Cys 90 and Cys 93 and are partially buried. The side chain of the conserved residue Gln 54 is buried and forms hydrogen bonds to the mainchain of β41 and α87. The hydrophobic residues 50–53 are all exposed to solvent, as are residues 47–50.

Mutagenesis of Arg 43 to Leu(as in FSH) in the whole hCG, or replacement of it by Ala or Asp in synthetic (38–57) peptides either significantly diminishes binding or eliminates it in the case of the peptides. Retention of partial activity is yet more evident for multiple binding sites over the hormone surface. From the orientation of Arg 43 in the structure a possible role in receptor binding is to stabilise the conformation of Pro 50 and the long loop region.

3) The (α88–92) C-terminus

The C-terminus of the α-subunit has been highly conserved throughout evolution, the five amino acid residues of the carboxy-terminus, Tyr-Tyr-His-Lys-Ser-COOH are identical in 13 of the 19 available amino acid sequences and His 90 and Lys 91 are invariant. It has been shown that carboxypeptidase digestion of both hCGα and LHα, while not detrimental to subunit assembly, essentially eliminates receptor binding of the diner. Des-(89–92)hCGα has been shown to form an active heterodimer with the β-subunit but with reduction of both receptor binding and initiation of steroidogenesis.

The C-terminus of the α subunit is located in close proximity to both the 'long loop' and the 'determinant loop' of the β subunit, which would imply a single major receptor binding site. Although residues 88 and 89 are poorly defined and final three residues are not seen in the structure, it can be deduced that they extend out beside the 'determinant loop' as shown in FIG. 4 and it seems likely that the invariant His 90 and Lys 91 are involved in receptor binding.

3) BIOLOGICAL ACTIVITY

Appropriate glycosylation of gonadotropins has been shown to be essential for full expression of their biological activity. Chemically deolycosylated hCG (HF-hCG) binds to receptors with slightly increased affinity but the potency in activating adenylate cyclase and steroidogenesis is either greatly reduced or abolished.

The structure provides an explanation why the carbohydrate at α52 Asn is critical to the biological activity of the hormone. The carbohydrate is positioned at the dimer interface and is about 4 Å away from the determinant loop and the observation that removal of carbohydrate increases receptor binding can be explained by the close proximity of this carbohydrate chain to the potential receptor binding site of the hormone. It can be envisaged that its position, size and flexibility could be antagonistic to a completely peptide based receptor binding.

Site-directed mutagenesis studies have shown that removal of both β-subunit N-glycosylation sites does not cause drastic loss of activity, but this mutant is not able to produce the same maximal steroidogenic activity in mouse Leydig tumor cells (MA-10 cells). The two Asn residues are very close to each other and located 20 Å from α52 Asn which would seem to indicate a different site of action, but modelling with the complete complex carbohydrate shows that in fact the carbohydrates would be quite close to each other and form a band of carbohydrate around the molecule.

COMPUTER ASSISTED hCG ANALOGUE DESIGN

Figure 8:
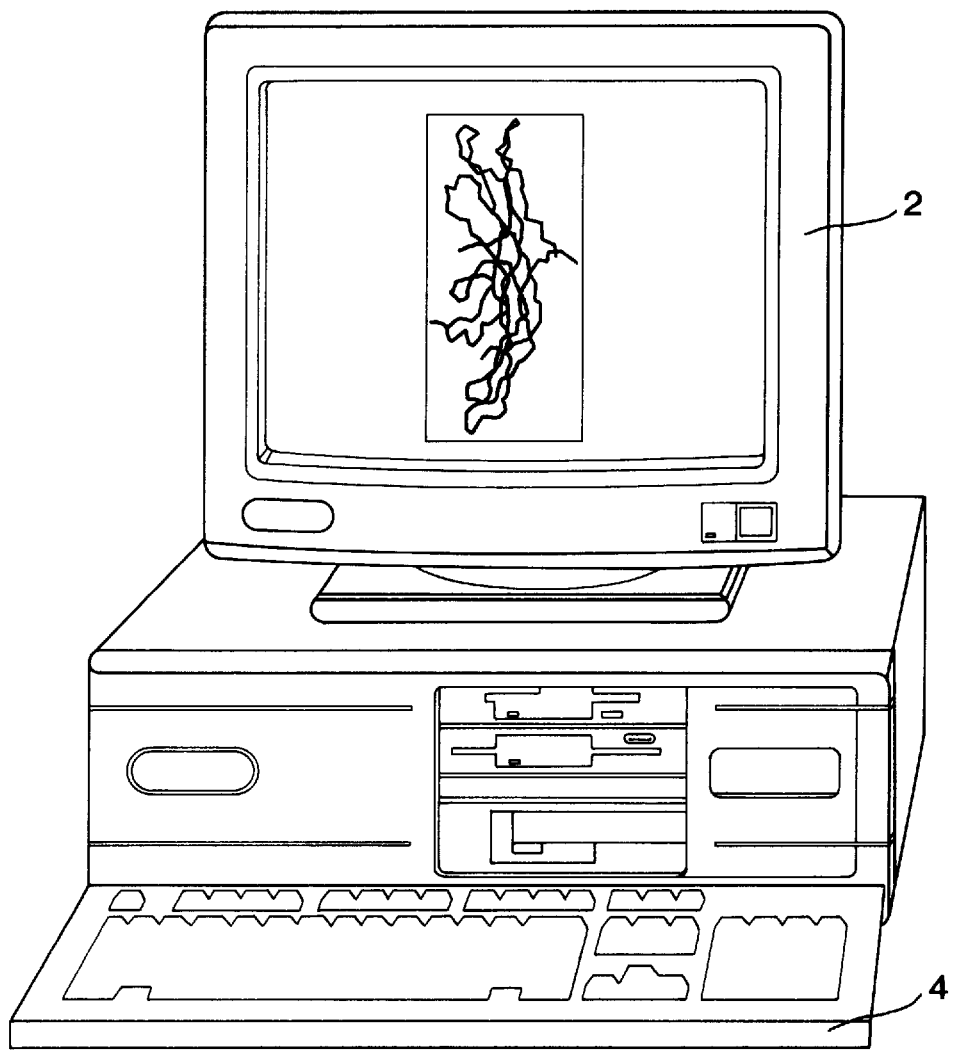
FIG. 8 is an elevation of a computer keyboard (4) and screen (2) displaying an hCG three-dimensional structure.
Figure 9:
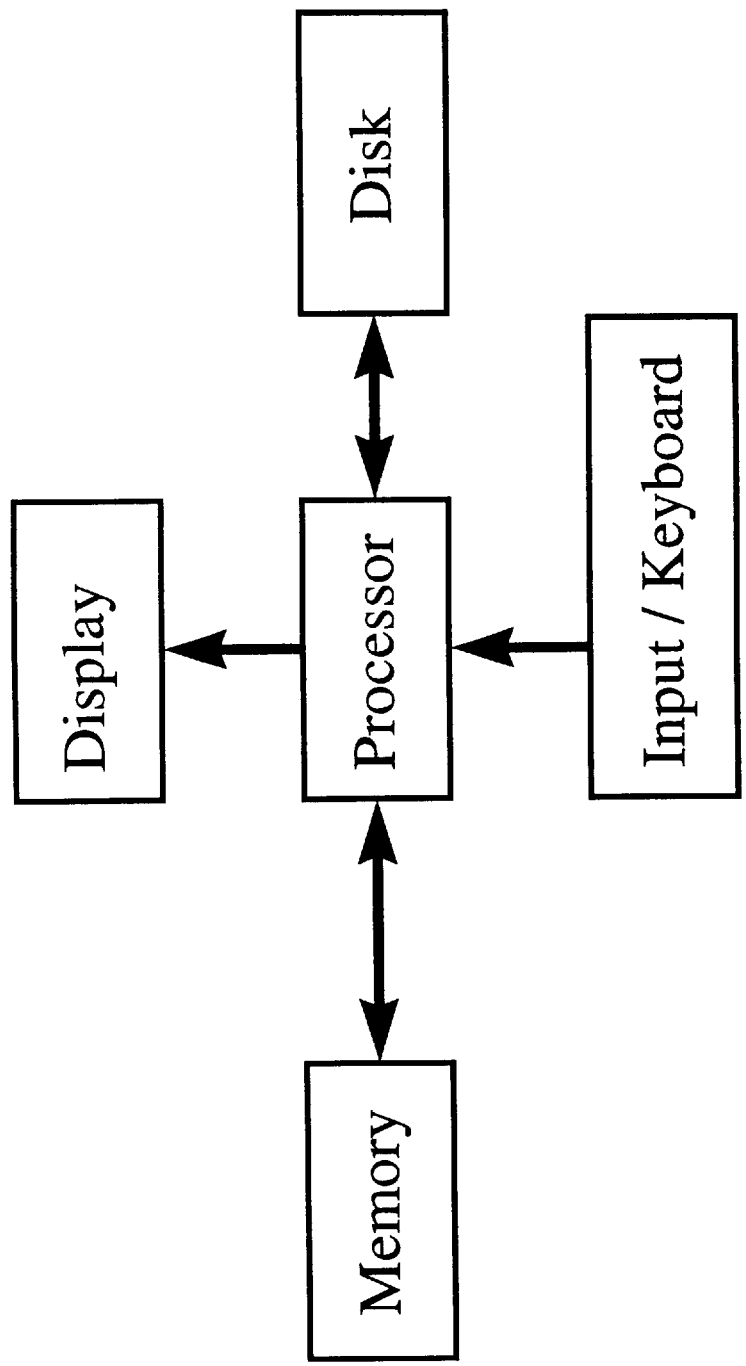
FIG. 9 is a block diagram of the components of the computer.
Figure 10:
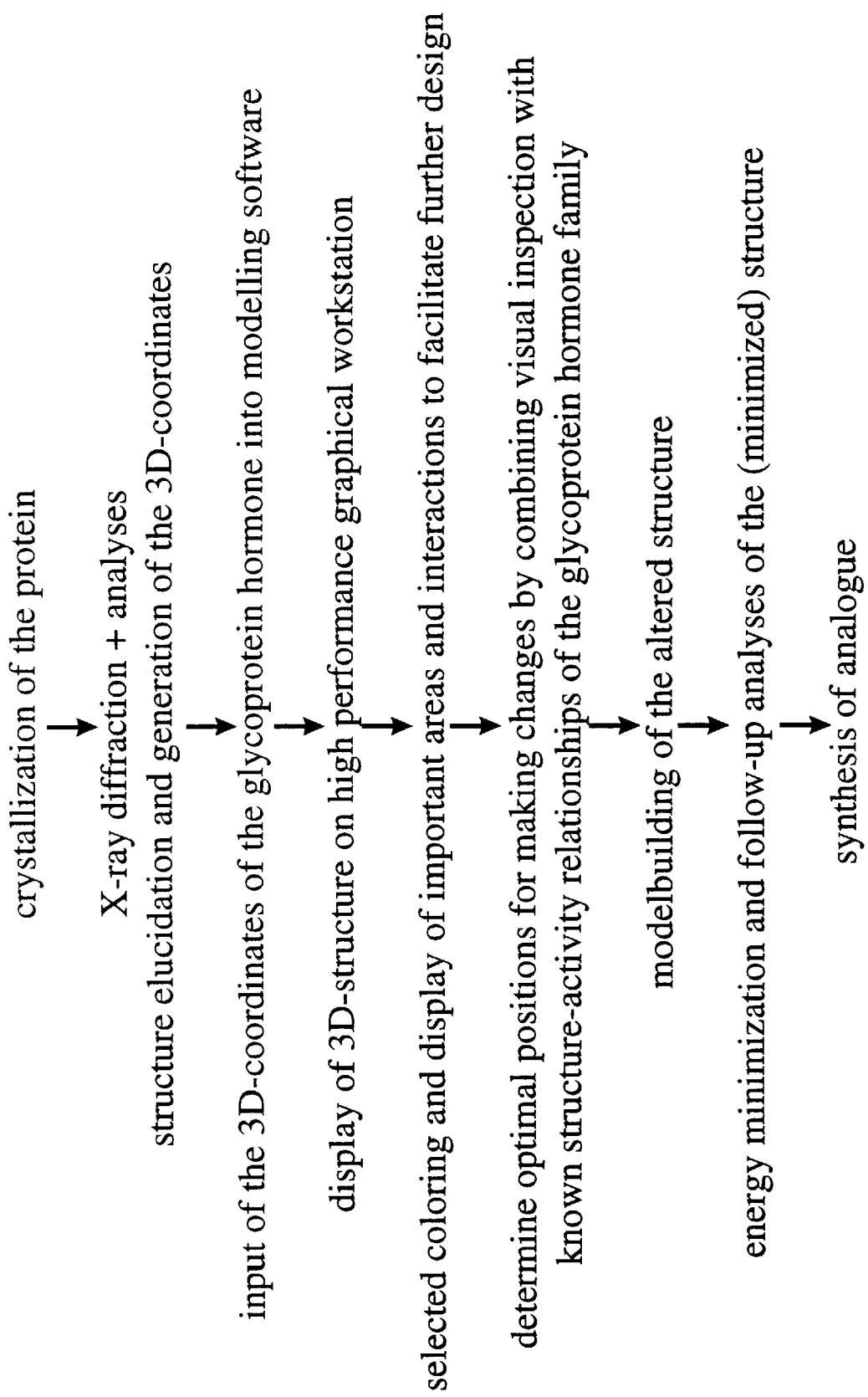
FIG. 10 is a general schematic protocol for carrying out an embodiment of the invention.
Figure 11:
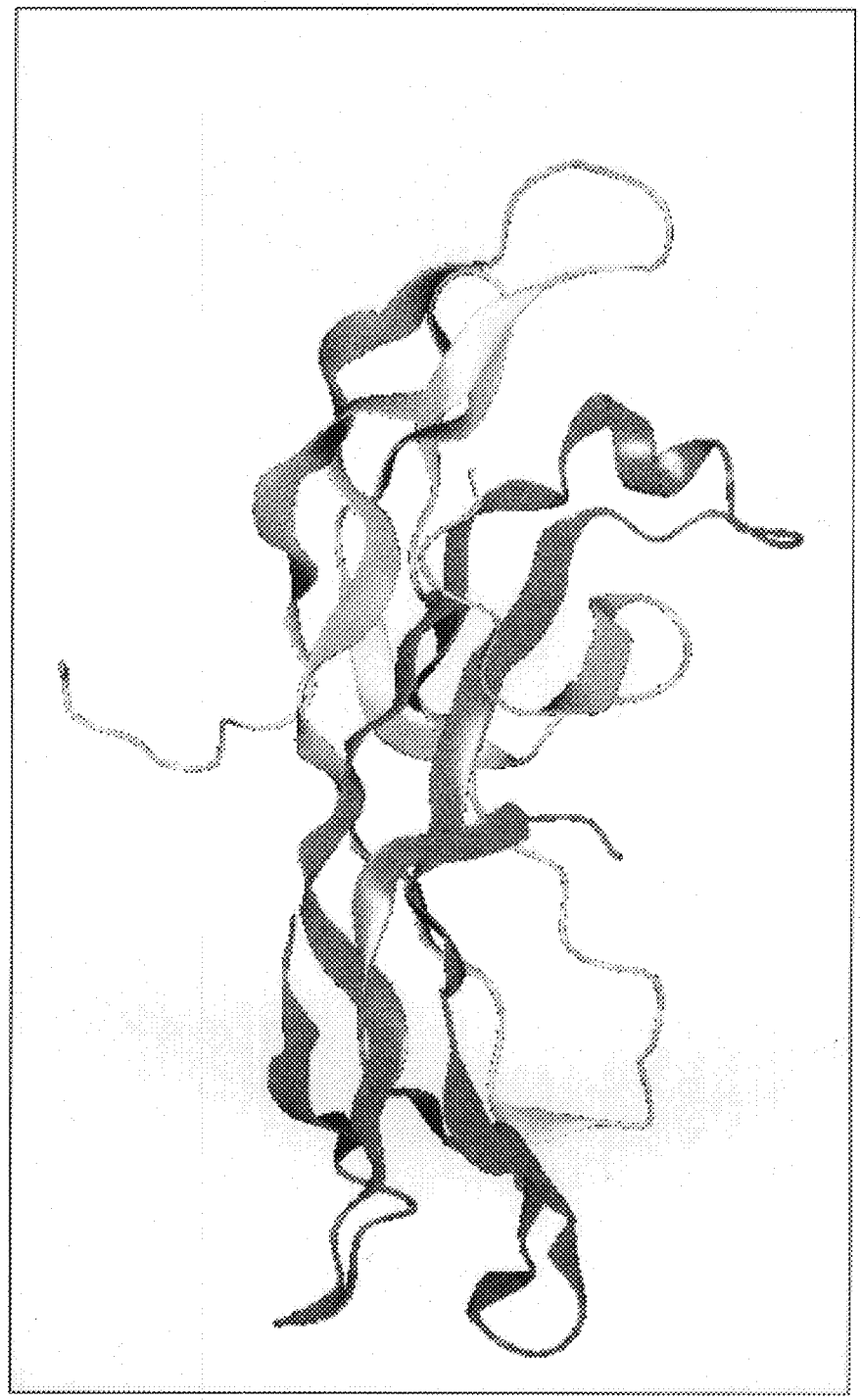
FIG. 11 is a three-dimensional representation of modified hCG analogue produced according to Example 2.

FIG. 8 shows a computer visual display means in the form of a computer monitor 2 connected to a computer (not shown) and a keyboard 4 also connected to the computer. The computer is loaded with a commercially-available software package comprising a plurality of programs operating together to provide a three-dimensional simulated model of the hCG molecule and to simulate the affect any chemical changes made to the structure thereof may have on the three-dimensional shape thereof. On the monitor is displayed the three-dimensional shape of hCG according to FIG. 5*c*.

FIG. 9 is a block diagram of the computer used to store and execute the three-dimensional molecular simulation software, which comprises a memory which may typically include a random access memory and optionally a read only memory. A hard disc memory is also provided onto which the software is loaded and stored, and into which the input coordinates data and inputted changes in chemical structure may be stored. The three-dimensional representations of the original hormone and hormone analogue may also be stored on the disc. Data processing operations are carried out in the processor which receives information from the memory and the disc, and also receives input information from the input means such as a keyboard. The processor also generates three-dimensional representions of the molecules and displays these on the visual display means e.g. computer monitor.

A general protocol for applying the invention is schematically depicted in FIG. 10.

EXAMPLES

Example 1

Glycoprotein Hormones With Additional Glycosylation Sites

By inspection of the 3D-structure of hCG it is possible to indicate optimal positions where the consensus sequence for N-glycosylation (Asn-X-Ser/Thr, X not Pro) can be introduced. The selection criteria have been described in the text above. Based on the 3D-structure of hCG homology built models of FSH and LH may also be constructed; thus allowing optimal positions in these gonadotropins to be determined. By one single point mutation extra glycosylation sites are created in [1]–[8] as follows:

[1] hCG:alpha[68]:Val→Ser or Thr
[2] hCG:alpha[17]:Phe→Asn
[3] hCG:alpha[67]:Arg→Asn
[4] hCG:beta[64]:Phe→Asn
[5] hCG:beta[79]:Val→Asn
[6] FSH:beta[64]:Tyr→Asn
[7] FSH:beta[79]:Leu→Asn
[8] LH:beta[64]:Phe→Asn Example 2

Beta-hairpin Modification of hCG

In order to further reduce the size of the glycoprotein hormone family, non-essential hairpins are deleted. Inspection of the 3D-structure and knowledge of the structure-activity relationships indicates that in particular the beta strand formed by residues 57 to 90 of the beta subunit is an attractive candidate for a truncation. Apart from specifying which residues can be deleted also several additional residues are needed to join the separated regions and to form the new hairpin loop. For this purpose amino acids that are known to frequently occur in hairpins are used. For several types of beta turns, preference exists for the amino acid composition at the 3 and 4 positions in the loop. Thus, taking all of this into account, the following structure is produced: [9] beta[1–59]-Asp-Ser-Asn-beta[86–108] combined with alpha.

The modified hCG analogue produced by the computer software to incorporate these chemical changes and the three-dimensional structure displayed on the computer monitor is shown in FIG. 11.

REFERENCES

1. Manjunath, P. & Sairam, M. R. J. Biol, Chem. 257, 7109–7115(1982).

2. Harris, D. C., Machin, K. J., Evin, G. M., Morgan, F. J. & Isaacs, N. W. J. Biol. Chem 264, 6705–6706(1989).

3. Lustbader, J. W., Birken, S., Pileggi, N. F., Kolks, M. A. G., Pollack, S., Cuff, M. E., Yang, W., Hendrickson, W. A. & Canfield, R. E. Biochemistry 28, 9239–9234(1989).

4. Tyan, R. J., Keutmann, H. T., Charlesworth, M. C., McCormick, D. J., Milius, R. P., Calvo, F. O. & Vutyavanich, T. Rec. Prog. in Hormone Res. 43,383–429 (1987).

5. Murray-Rust, J., McDonald, M. Q., Blundell, T. L., Hosang, M., Oefner, C., Winkler, F. & Bradshaw, R. S., Structure 1, 153–159(1993).

6. McDonald, N. W. & Hendrickson, W. A. Cell 73, 421–424(1993).

7. McDonald, N. W., Lapatto, R., Murray-Rust, J., Gunning, J., Wlodawer, A. & Blundell, T. L. Nature 354, 411–414(1991).

8. Schlunegger, M. P. & Grutter, M. G. J. Mol., Biol. 231, (1993).

9. Oefner, C., D'Arcy, A., Winkler, F. K., Eggiman, B & Hosang, M. EMBO J. 11, 3932–3926 (1992).

We claim:

1. A method for determining whether an analogue of human chorionic gonadotropin (hCG) will have an altered three-dimensional structure as compared to said hCG, which comprises (i) determining the three-dimensional coordinates of atoms of a hCg molecule;

(ii) providing a computer having a memory means, a data input means, a visual display means, said memory means containing three-dimensional molecular simulation software operable to retrieve co-ordinate data from said memory means and to display a three-dimensional representation of a molecule on said visual display means and being operable to produce a three-dimensional representation of an analogue of said molecule responsive to operator-selected changes to the chemical structure of said molecule and to display the three-dimensional representation of the analogue;

(iii) inputting three-dimensional coordinate data of the atoms of the hCG molecule into the computer and storing said data in the memory means;

(iv) displaying a three-dimensional representation of said hCG molecule on said visual display means;

(v) inputting into the data input means of said computer at least one operator-selected change in chemical structure of said hCG molecule;

(vi) executing said molecular simulation software to produce a modified three-dimensional molecular representation of said analogue structure; and (vii) displaying the three-dimensional representation of said analogue on said visual display means, whereby changes in three-dimensional structure of the hCG molecule consequent on changes in chemical structure can be visually determined.

2. The method according to claim 1, wherein the changes in chemical structure inputted into the data input means introduce a new N-glycosylation site having the amino acid sequence Asn-X-Ser/Thr where X can be any amino acid with the exception of Pro; the new N-glycosylation site being located at the molecular surface of the hCG analogue produced.

3. The method according to claim 2, where in the new N-glycosylation site is introduced by a single point mutation at a specified position selected from the group consisting of:

(i) in hCG at alpha (68), change Val to Ser or Thr;

(ii) in hCG at alpha (17), change Phe to Asn;

(iii) in hCG at alpha (67), change Arg to Asn;

(iv) in hCG at beta (64), change Phe to Asn;

(v) in hCG at beta (79), change Val to Asn;

where the positions refer to amino acid positions on the alpha or beta subunit of hCG.

4. The method according to claim 1 wherein the changes in chemical structure inputted into the data input means effect deletion of a hairpin loop in the beta subunit of the human chorionic gonadotrophin (hCG) glycoprotein to produce a structure:

beta [1–59]-Asp-Ser-Asn-beta [86–108]

where amino acid residues 60 to 85 have been deleted and replaced by an Asp-Ser-Asn link, and the alpha subunit is unchanged.

5. The method according to claim 6, wherein the selection of the analogue structure comprises displaying on said visual display means the three-dimensional structure of both the original hCG hormone and the hCG analogue, visually comparing the configuration and spatial arrangement of the regions involved in receptor binding and/or signal transduction, and selecting an analogue structure wherein said regions are substantially the same.

6. A method for screening hCG analogues that mimic the three-dimensional structure of said hCG; which comprises producing a multiplicity of analogue structures of the hCG by the method of claim 1, and selecting an analogue structure represented by a three-dimensional representation wherein the three-dimensional configuration and spatial arrangement of regions involved in receptor binding and/or signal transduction of said hCG remain substantially preserved.

7. A method for producing an analogue of a hCG that mimics the three-dimensional structure of said hCG, which comprises (i) determining the three-dimensional coordinates of atoms of an hCG molecule;

(ii) providing a computer having a memory means, a data input means, a visual display means, said memory means containing three-dimensional molecular simulation software operable to retrieve co-ordinate data from said memory means and to display a three-dimensional representation of a molecule on said visual display means and being operable to produce a modified three-dimensional analogue representation responsive to operator-selected changes to the chemical structure of said molecule and to display the three-dimensional representation of the modified analogue;

(iii) inputting three-dimensional co-ordinate data of atoms of the hCG molecule into the computer and storing said data in the memory means;

(iv) inputting into the data input means of said computer at least one operator-selected change in chemical structure of said hCG molecule;

(v) executing said molecular simulation software to produce a modified three-dimensional molecular representation of said analogue structure;

(vi) displaying the three-dimensional representation of said analogue on said visual display means, whereby changes in three-dimensional structure of the hCG consequent on changes in chemical structure can be visually monitored;

(vii) repeating steps (iv) through (vi) to produce a multiplicity of analogues;

(viii) selecting an analogue structure represented by a three-dimensional representation wherein the three-dimensional configuration and spatial arrangement of regions involved in receptor binding and/or signal transduction of said hCG remain substantially preserved;

(ix) synthesizing said selected analogue by means of recombinant DNA technology; and (x) determining the hCG activity of said synthesized hCG analogue, whereby an analogue having said activity is a mimic of the three-dimensional structure of hCG.

8. A method for producing an analogue structure of the alpha subunit of FSH, TSH or LH that mimics the three-dimensional structure of said alpha subunit of FSH, TSH or LH, respectively, which comprises (i) applying the results obtained for hCG from the method of claim 1 to construct analogous analogues of the alpha subunits of FSH, TSH or LH; and (ii) determining the FSH, TSH, or LH activity of the FSH, TSH and LH analogues, respectively, whereby an analogue having said activity is a mimic of the three-dimensional structure of FSH, TSH or LH, respectively.

9. The method according to claim 8, wherein said analogue has a new N-glycosylation site having the amino acid sequence Asn-X-Ser/Thr where X can be any amino acid with the exception of Pro, the new N-glycosylation site being located at the molecular surface of the analogue produced.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 92 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( v i ) ORIGINAL SOURCE:
( A ) ORGANISM: Homo sapiens
( B ) STRAIN: ALPHA-SUBUNIT HUMAN CHORIONIC GONADOTROPIN ( x i ) SEQUENCE DESCRIPTION: SEQ ID NO: 1:

```
Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60
```

```
Tyr Asn Arg Val Thr Val Met Gly Gly Phe Lys Val Glu Asn His Thr
65              70              75                   80

Ala Cys His Cys Ser Thr Cys Tyr Tyr His Lys Ser
                85              90
```

(2) INFORMATION FOR SEQ ID NO: 2:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Homo sapiens
        (B) STRAIN: BETA-SUBUNIT HUMAN CHORIONIC GONADOTROPIN (xi) SEQUENCE DESCRIPTION: SEQ ID NO: 2:

```
Ser Lys Glu Pro Leu Arg Pro Arg Cys Arg Pro Ile Asn Ala Thr Leu
1               5               10              15

Ala Val Glu Lys Glu Gly Cys Pro Val Cys Ile Thr Val Asn Thr Thr
            20              25              30

Ile Cys Ala Gly Tyr Cys Pro Thr Met Thr Arg Val Leu Gln Gly Val
        35              40              45

Leu Pro Ala Leu Pro Gln Val Val Cys Asn Tyr Arg Asp Val Arg Phe
    50              55              60

Glu Ser Ile Arg Leu Pro Gly Cys Pro Arg Gly Val Asn Pro Val Val
65              70              75              80

Ser Tyr Ala Val Ala Leu Ser Cys Gln Cys Ala Leu Cys Arg Arg Ser
                85              90              95

Thr Thr Asp Cys Gly Gly Pro Lys Asp His Pro Leu Thr Cys Asp Asp
            100             105             110

Pro Arg Phe Gln Asp Ser Ser Ser Ser Lys Ala Pro Pro Pro Ser Leu
        115             120             125

Pro Ser Pro Ser Arg Leu Pro Gly Pro Ser Asp Thr Pro Ile Leu Pro
    130             135             140

Gln
145
```